(12) United States Patent
Tikhomirov et al.

(10) Patent No.: US 12,084,510 B2
(45) Date of Patent: Sep. 10, 2024

(54) ANTIBODIES SELECTIVE FOR CELLS PRESENTING EGFR AT HIGH DENSITY

(71) Applicants: GILEAD SCIENCES, INC., Foster City, CA (US); NATIONAL RESEARCH COUNCIL OF CANADA, Ottawa (CA)

(72) Inventors: Ilia Alexandre Tikhomirov, Toronto (CA); Maria L. Jaramillo, Beaconsfield (CA); Maureen D. O'Connor-McCourt, Beaconsfield (CA); Traian Sulea, Kirkland (CA); Renald Gilbert, Montreal (CA); Bruno Gaillet, Sainte Julienne (CA); Jason Baardsnes, Montreal (CA); Myriam Banville, Laval (CA); Suzanne Grothe, Montreal (CA)

(73) Assignees: Gilead Sciences, Inc., Foster City, CA (US); National Research Council of Canada, Ottawa (CA)

( * ) Notice: Subject to any disclaimer, the term of this patent is extended or adjusted under 35 U.S.C. 154(b) by 538 days.

(21) Appl. No.: 16/797,364

(22) Filed: Feb. 21, 2020

(65) Prior Publication Data

US 2020/0325243 A1    Oct. 15, 2020

Related U.S. Application Data

(63) Continuation of application No. 13/821,832, filed as application No. PCT/CA2012/050034 on Jan. 20, 2012, now Pat. No. 10,570,211.

(60) Provisional application No. 61/435,510, filed on Jan. 24, 2011.

(51) Int. Cl.
*C07K 16/30* (2006.01)
*C07K 16/28* (2006.01)

(52) U.S. Cl.
CPC .......... *C07K 16/30* (2013.01); *C07K 16/2863* (2013.01); *C07K 2317/56* (2013.01); *C07K 2317/565* (2013.01); *C07K 2317/567* (2013.01)

(58) Field of Classification Search
CPC ............ C07K 16/2863; C07K 2317/56; C07K 2317/565; C07K 16/30; C07K 2317/567
See application file for complete search history.

(56) References Cited

U.S. PATENT DOCUMENTS

| | | | |
|---|---|---|---|
| 3,773,919 A | 11/1973 | Boswell et al. | |
| 5,208,020 A | 5/1993 | Chari et al. | |
| 5,595,756 A * | 1/1997 | Bally | A61K 9/1272 264/4.1 |
| 5,869,046 A | 2/1999 | Presta et al. | |
| 6,121,022 A | 9/2000 | Presta et al. | |
| 6,194,551 B1 | 2/2001 | Idusogie et al. | |
| 6,235,883 B1 | 5/2001 | Jokobovits et al. | |
| 6,441,163 B1 | 8/2002 | Chari et al. | |
| 7,125,689 B2 | 10/2006 | Carr et al. | |
| 7,589,180 B2 | 9/2009 | Old et al. | |
| 7,628,986 B2 | 12/2009 | Weber et al. | |
| 7,807,798 B2 | 10/2010 | Jakobovits et al. | |
| 7,887,805 B2 | 2/2011 | Pedersen et al. | |
| 8,088,387 B2 | 1/2012 | Steeves et al. | |
| 8,790,649 B2 | 7/2014 | Setiady et al. | |
| 9,125,896 B2 | 9/2015 | Setiady et al. | |
| 9,233,171 B2 | 1/2016 | Setiady et al. | |

FOREIGN PATENT DOCUMENTS

| | | |
|---|---|---|
| WO | 1994029351 | 12/1994 |
| WO | 1996040210 | 12/1996 |
| WO | 2001000244 | 1/2001 |
| WO | 2004032960 | 4/2004 |
| WO | 2006009694 | 1/2006 |
| WO | 2008104183 | 9/2008 |
| WO | 2012075581 | 6/2012 |
| WO | 2012100346 | 8/2012 |
| WO | 2013078271 | 5/2013 |
| WO | 2014143765 | 9/2014 |
| WO | 2015000062 | 1/2015 |

OTHER PUBLICATIONS

Paul, Fundamental Immunology, 3 Edition, 1993, pp. 292-295 (Year: 1993).*
MacCallum et al. Antibody-antigen Interactions: Contact Analysis and Binding Site Topography. J. Mol. Biol. (1996) 262:732-745 (Year: 1996).*
Casset et al. A peptide mimetic of an anti-CD4 monoclonal antibody by rational design. (2003) BBRC 307, 198-205 (Year: 2003).*
Brown et al. Tolerance to Single, but Not Multiple, Amino Acid Replacements in Antibody VH CDR2. Journal of Immunology. May 1996; 156(9):3285-91 (Year: 1996).*
Rudikoff et al. Single amino acid substitution altering antigen-binding specificity. Proc. Natl. Acad. Sci. USA, 79(6):1979-1983, Mar. 1982 (Year: 1982).*
Jonker et al. New England Journal of Medicine. 2007; 357:2040-8 (Year: 2007).*
Vermorken et al. New England Journal of Medicine. 359:1116-27 (Year: 2007).*
Heppner et al. (Cancer Metastasis Review 2:5-23; 1983 (Year: 1983).*
Sporn et al. Chemoprevention of Cancer, Carcinogenesis, vol. 21 (2000), 525-530 (Year: 2000).*
Auerbach et al. Cancer and Metastasis Reviews, 2000, 19: 167-172 (Year: 2000).*

(Continued)

*Primary Examiner* — Vanessa L. Ford
*Assistant Examiner* — Sandra Dillahunt
(74) *Attorney, Agent, or Firm* — Fitch, Even, Tabin & Flannery LLP

(57) ABSTRACT

Herein described are antibodies to epidermal growth factor receptor (EGER) having an EGER binding affinity that is sufficient to kill disease cells presenting EGFR at high density, but is insufficient for binding to normal cells. A therapeutic effect is thus achieved while avoiding adverse events that result from unintended binding to normal cells.

25 Claims, 7 Drawing Sheets

Figures 1, 1A:
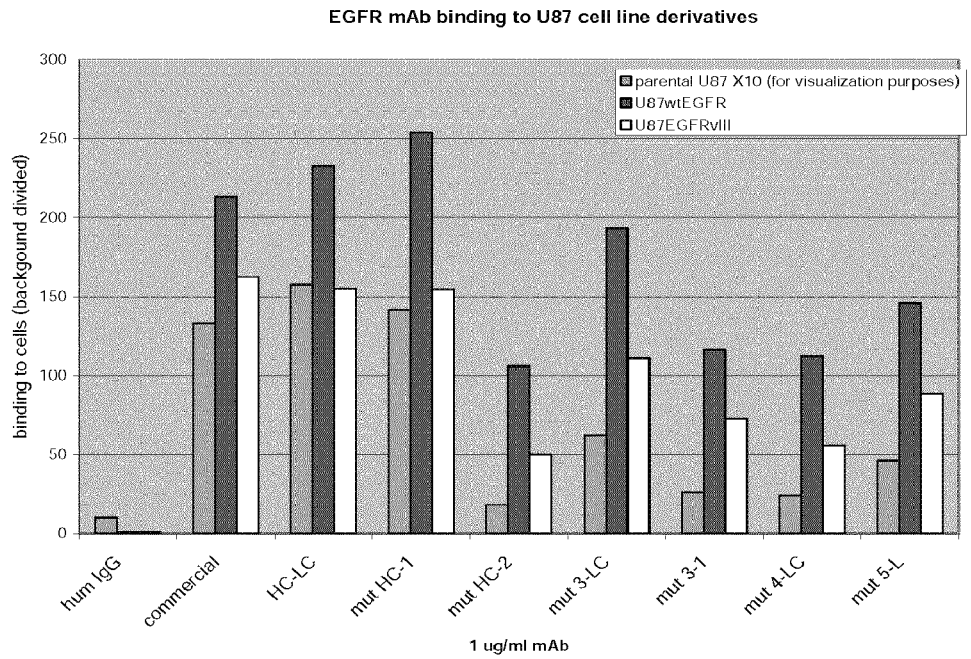
Figures 1, 1B:
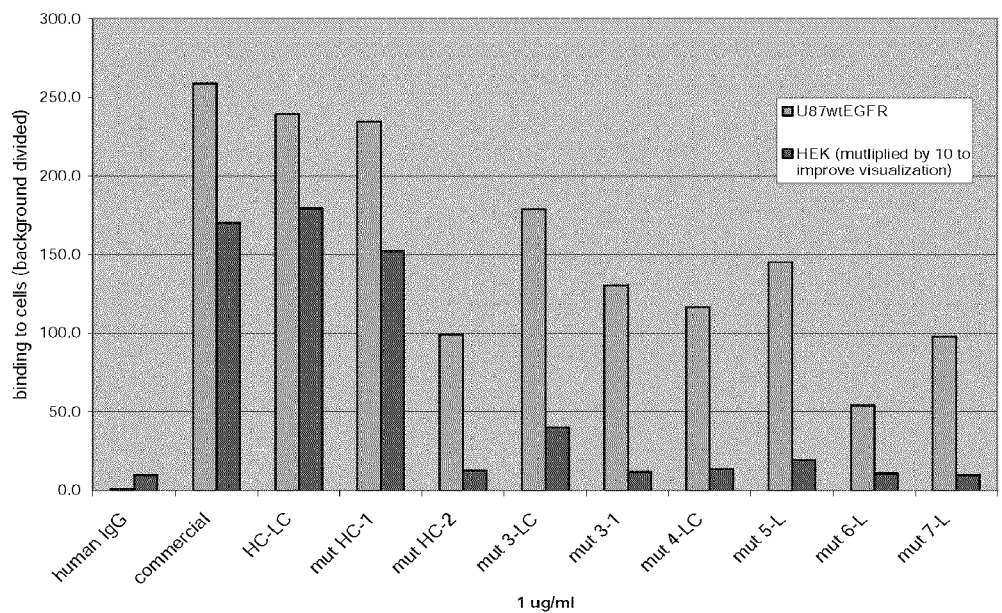

Specification includes a Sequence Listing.

(56) References Cited

OTHER PUBLICATIONS

Gura T. Science, 1997, 278(5340): 1041-1042 (Year: 1997).*
Jain RK. Scientific American, Jul. 1994,58-65 (Year: 1994).*
Hait. Nature Reviews/Drug Discovery, 2010, 9, pp. 253-254 (Year: 2010).*
Gravanis et al. Chin Clin Oncol, 2014, 3, pp. 1-5) (Year: 2014).*
Beans. PNAS 2018; 115(50): 12539-12543 (Year: 2018).*
European Search Report issued by the European Patent Office for European Patent Application 14819422.8 dated Feb. 2, 2018, 7 pages.
Setiady et al. Abstract 5463: Development of a novel antibody-maytansinoid conjugate, IMGN289, for the treatment of EGFR-expressing solid tumors. Cancer Research, Apr. 15, 2013. Retrieved from the Internet URL:http://ancerres.aacrjournals.org/content/73/8 Supplement 5463, 5 pages.
PCT International Search Report and Written Opinion issued by the International Searching Authority for Application PCT/CA2014/000543, dated Aug. 11, 2014, 12 pages.
Office Action issued in U.S. Appl. No. 14/903,037 on Feb. 8, 2018, 7 pages.
Office Action issued in U.S. Appl. No. 14/903,037 on Nov. 29, 2017, 7 pages.
Dechant et al. Complement-dependent tumor cells lysis triggered by combinations of epidermal growth factor receptor antibodies. Cancer Research 2008, 68(13) 4998-5003.
International Search Report for PCT/CA2015/000557 dated Mar. 7, 2016, 8 pages.
Perera et al. Treatment of human tumor xenografts with monoclonal antibody 806 in combination with a prototypical epidermal growth factor receptor-specific antibody generates enhanced antitumor activity. Clinical Cancer Research, 2005, 11(17), 6390-6399.
Spangler et al. Combination antibody treatment down-regulates epidermal growth factor receptor by inhibiting endosomal recycling. Proceedigns of the National Academy of Sciences, 2010, 107(30), 13252-13257.
Brown et al. Tolerance to Single, but not Multiple, Amino Acid Replacements in Antibody, V CDR2. Journal of Immunology. May 1996, 156(9):3285-91.
Rudikoff et al. Single amino acid substitution altering antigen-binding specificity. Proc. Natl. Acad. Sci. USA, 79 (6):1979-1983, Mar. 1982.
Colman. Effects of amino acid sequence changes on antibody-antigen interactions. Research in Immunology, 145:33-36, 1994.
Cooper et al. Variable domain identical antibodies exhibit IgG subclass related differences in affinity and kinetic constants as determined by surface pasmon resonance. Molecular Immunology, 1994; 31 (8):577-584.
Jonker et al. Cetuximab for the treatment of colorectal cancer. New England Journal of Medicine. 2007; 357:2040-8.
Vermorken et al. Platinum based chemotherapy plus cetuximab in head and neck cancer. New England Journal of Medicine. 359:1116-27.
Heppner et al. Tumor heterogeneity: biological implications and therapeutic consequences. Cancer Metastasis Review 2:5-23, 1983.
Boland, W. et al. The Emerging Role of Nimotuzumab in the Treatment of Non-Small Cell Lung Cancer. Biologics, vol. 4, 2010, pp. 289-298.
Carter, P. et al. Identification and validation of cell surface antigens for antibody targeting in oncology. Endocrine-Related Cancer, vol. 11, 2004, pp. 659-687.
Crombet, T. et al. Use of the Humanized Anti-Epidermal Growth Factor Receptor Monoclonal Antibody h-R3 in combination with Radiotherapy in the Treatment of Locally Advanced Head and Neck Cancer Patients. Journal of Clinical Oncology, vol. 22, No. 9, May 1, 2004, pp. 1646-1654.
Donaldson, J.M., et al. Design and Development of Masked Therapeutic Antibodies to Limit Off-Target Effects: Application to Anti-EGFR Antibodies. Cancer Biol. Ther., vol. 8, 2007, pp. 200-209.
Gaillet, B. et al. High Level Recombinant Protein Production in CHO Cells Using an Adenoviral Vector and the Cumate Gene-Switch. Biotechnol. Prog., vol. 23, 2007, pp. 200-209.
Gerstner, R.B., et al. Sequence Plasticity in the Antigen-binding Site of a Therapeutic Anti-HJER2 Antibody. J. Mol. Biol., vol. 321, 2002, pp. 851-862.
Kelley, R.F. et al. Thermodynamic Analysis of an Antibody Functional Epitope. Biochemistry, vol. 32, 1993, pp. 6828-6835.
Lee C.V. Bivalent antibody phage display mimics natural immunoglobulin. Journal of Immunological Mehtods. vol. 284, 2004, pp. 119-132.
Li, S. et al. Structural basis for inhibition of the epidermal growth factor receptor by cetuximab. Cancer Cell, vol. 7, 2005, pp. 301-311.
Li, Z. et al. Monte Carlo-minimization approach to the multiple-minima problem in protein folding. Proc. Natl. Acad. Sci. U.S.A., vol. 84, Oct. 1987, pp. 6611-6615.
Mullick, A., et al. The cumate gene-switch: a system for regulated expression in mammalian cells. BMC Biotechnol., vol. 6, 2006, p. 43.
Naim, M., et al. Solvated Interaction Energy (SIE) for Scoring Protein-Ligand Binding Affinities. J. Chem. Inf. Model, vol. 47, 2007, pp. 122-133.
Selzer, T. et al. Rational design of faster associating and tighter binding protein complexes. Nat. Struct. Biol., vol. 7, No. 7, Jul. 2000, pp. 537-541.
Watkins, J.D., et al. Discovery of Human Antibodies to Cell Surface Antigens by Capture Life Screening of Phage-Expressed Antibody Libraries. Analytical Biochemistry, vol. 256, Article No. AB972523, 1998, pp. 169-177.
International Search Report, dated May 14, 2012, in connection with corresponding International Application No. PCT/CA2012/050034.
Supplementary European Search Report issued in Application No. EP12738907 and completed on Jun. 25, 2015.
Tikhomirov, et al. Bivalent Binding Properties of Epidermal Growth Factor Receptor (EGFR) Targeted Monoclonal Antibodies: Factors Contributing to Differences in Observed Clinical Profiles (A36), AACR Cancer Clinical Trials and Personalized Medicine, 2008.
Ramakrishanan et al. Nimotuzamab, a promising therapeutic monoclonal for treatment of tumors of epithelial origin. MAGS, 2009, pp. 41-48.
Talavera et al. Nimotuzumab, an antitumor antibody that targets the epidermal growth factor receptor blocks ligand binding while permitting the active receptro conformation. Cancer Research, vol. 69, No. 14, 2009, pp. 5851-5859.
Miqueli et al. Biological Activity in Vitro of Anti-Epidermal Growth Factor Receptor Monoclonal Antibodies with Different Affinities. Hybridoma, vol. 26, No. 6, 2007, pp. 423-432.
Crombet, et al. Use of the Humanized Anti-Epidermal Growth Factor Receptor Monoclonal Antibody h-R3 in Combination with Advanced Head and Neck Cancer Patients. Journal of Clinical Oncology, vol. 22, No. 9, 2004, pp. 1646-1654.
Rudnick et al. Affinity and Avidity in Antibody-Based Tumor Targeting. Cancer Biotherapy & Radiopharmaceuticals, vol. 24, No. 2, 2009, pp. 155-161.
Oda et al. Reevaluation of Stoichiometry and affinity/avidity in interactions between anti-hapten antibodies and mono-or-multivalent antigens. Molecular Immunology, vol. 37, No. 18, 2000, pp. 1111-1112.
Garrido, et al. Bivalent binding by 1-15 intermediate affinity of nimotuzumab: A contribution to explain antibody clinical profile. Cancer Biology & Therapy. Vol. 11, No. 4, 2011, pp. 373-382.
MacCallum et al. Antibody-antigen interactions: contact analysis and binding site topography. J. Mol. Biol. 262:732-745, 1996.

* cited by examiner

A)
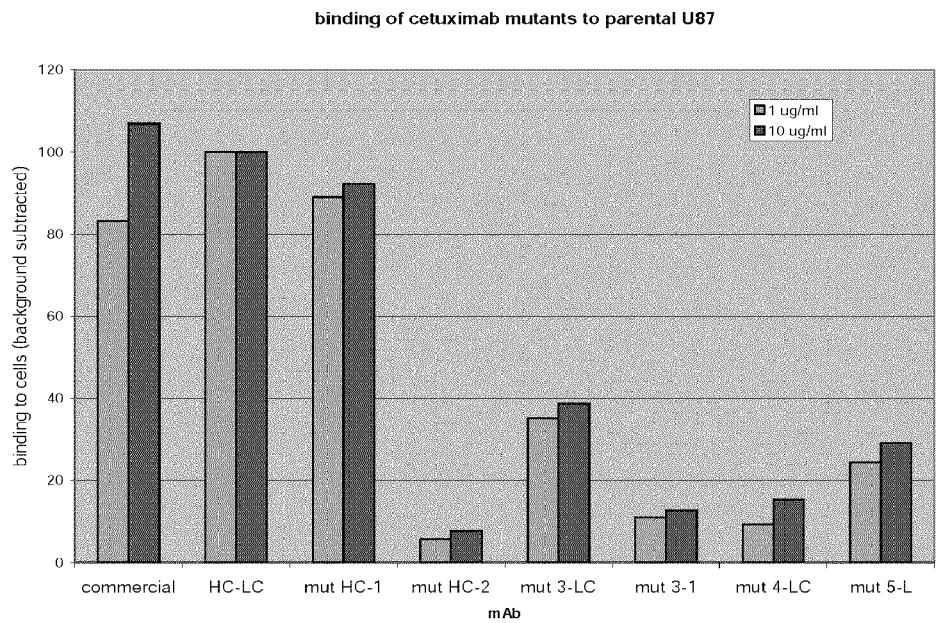
B)
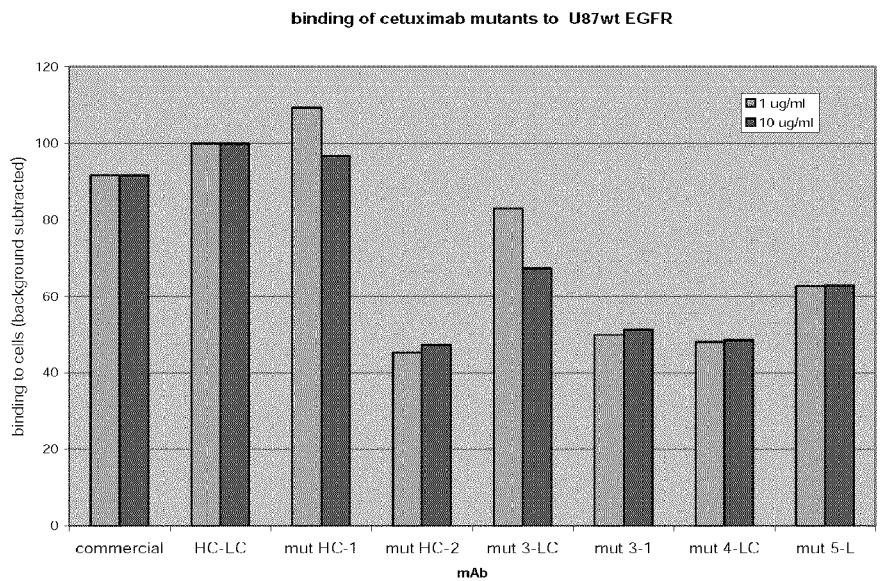
Figure 1 (A&B)

C)
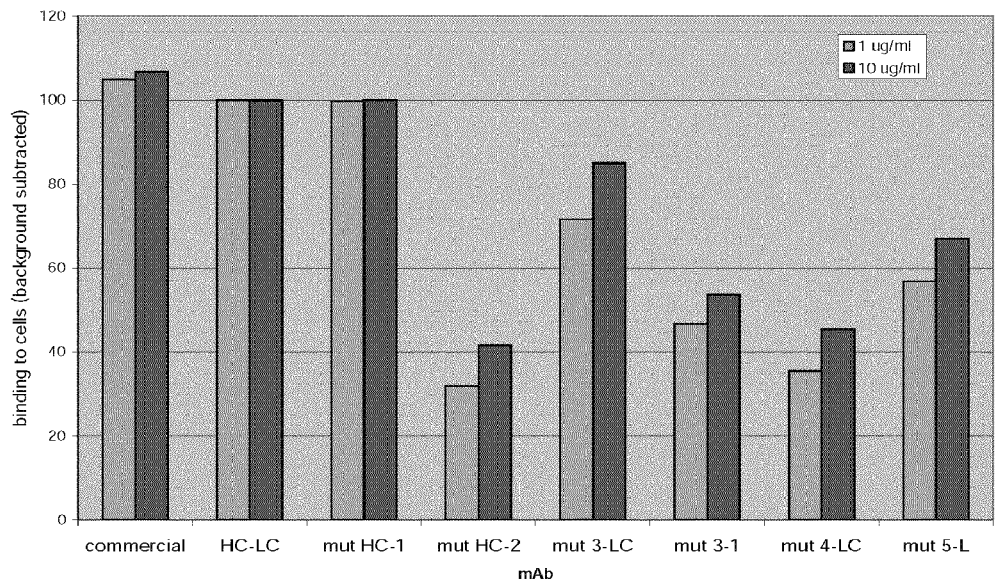
D)
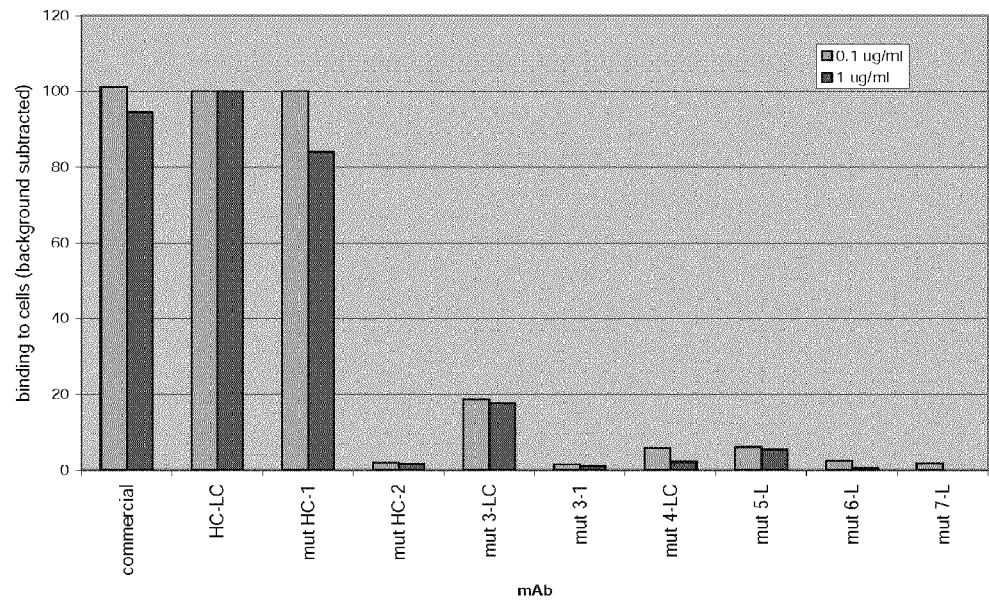
Figure 1(C&D)

ANTIBODIES SELECTIVE FOR CELLS PRESENTING EGFR AT HIGH DENSITY

CROSS-REFERENCE TO RELATED APPLICATIONS

This application is a continuation of U.S. patent application Ser. No. 13/821,832, filed Jun. 10, 2013, which is a U.S. National Stage Application under 35 U.S.C. § 371 of International Application No. PCT/CA2012/050034, filed Jan. 20, 2012, which claims the benefit of priority to U.S. Provisional Application No. 61/435,510, filed Jan. 24, 2011, the disclosures of each of which are hereby incorporated by reference in their entireties for all purposes.

DESCRIPTION OF THE TEXT FILE SUBMITTED ELECTRONICALLY HEREWITH

The contents of the text file submitted electronically herewith are incorporated herein by reference in their entirety: A computer readable format copy of the Sequence Listing (filename: FOBI_001_02US_SeqList.txt, date recorded: May 16, 2018, file size 59 kilobytes).

FIELD OF THE INVENTION

This invention relates to antibodies having therapeutic and diagnostic utility. More particularly, the present invention relates to antibodies that bind selectively to cells that present EGFR (epidermal growth factor receptor) at abnormally high density. The antibodies are useful therapeutically and diagnostically in the fields of oncology and other diseases.

BACKGROUND TO THE INVENTION

Drugs for the treatment of cancer and other diseases have a so-called "therapeutic window". In the case of cancer, the therapeutic window defines the drug dosage that can kill cancer cells preferentially to normal cells, thereby establishing a safety range for the use of the drug. The therapeutic window for conventional chemotherapeutics is narrow with, in many cases, significant adverse effects coinciding with marginal slowing of tumour growth. Targeted treatments that spare normal cells are urgently needed. Therapeutic antibodies form a newer class of cancer therapies that specifically target an antigen presented on the surface of cancer cells. When the target surface protein is unique to the cancer cell, adverse antibody effects on normal cells can be avoided. However, for the majority of antigens, target expression is not restricted completely to tumour cells, with some normal cells also expressing the antigen. In these cases, the antibody may have an effect on normal cells as well as tumor cells, leading to "on-target, off-tissue" adverse events. In the case of the EGFR antigen, because of its ubiquitous presence on the surface of normal cells such as keratinocytes as well as on cancer cells, the clinical use of EGFR-targeting therapeutics is associated with adverse events that include severe rash.

Considering the efficacy of anti-EGFR therapies in treating patients that overexpress EGFR, the risk associated with severe skin reaction is currently considered acceptable when managed properly. The risk of anti-EGFR therapy-associated toxicity can be reduced by prior administration of anti-histamine, or by administering anti-EGFR antibody at a reduced and less effective dose.

Efforts to improve upon EGFR antibodies are aimed at generating antibodies having even greater affinity for the target antigen. In WO 2006/009694 published 26 Jan. 2006, Kussie et al describe the crystal structure of the interaction between EGFR and cetuximab Fab fragment, and identify residues that may be modified to improve the effectiveness of cetuximab as an EGFR antagonist.

It would be desirable to provide an EGFR antibody that is useful to treat subjects presenting with EGFR over-expressing disease cells, while avoiding significant interaction with tissues including skin and particularly keratinocytes and other cells that also present the EGFR antigen at normal levels.

It is an object of the present invention to provide therapeutic antibodies, and fragments and conjugates thereof that bind effectively to a given target only when that target is presented at a relatively higher density characteristic of a disease state.

It is a further object of the present invention to provide such antibodies, fragments and conjugates in pharmaceutical compositions, particularly for therapeutic and diagnostic use.

It is a further object of the present invention to provide a method useful, in a subject in need thereof, to control the growth of disease cells that present EGFR at a density greater than normal EGFR density, while avoiding or minimizing adverse effects on normal cells.

SUMMARY OF THE INVENTION

In one aspect, the present invention provides an isolated, EGFR antibody or bivalent fragment thereof that binds preferentially to target cells that present EGFR at a density above a normal EGFR density. Cells that present EGFR at a density greater than normal EGFR density are disease cells, including cancer cells such as colorectal and other cancer cells, that over-express the her-1 gene, and manifest on their surface a greater number of EGFR proteins than cells that express the her-1 gene at normal levels.

The antibodies of the present invention, and their bivalent fragments, display a preference for binding to disease cells having the higher EGFR density, and show reduced and desirably minimal or negligible, i.e., insignificant, binding to normal cells having a normal EGFR density. The present antibodies and their bivalent binding fragments thus are well suited for use in reducing or eradicating high density EGFR disease cells while minimizing or avoiding effects on normal cells, thereby reducing the number or severity of adverse events in subjects receiving EGFR antibody therapy.

In one aspect, the EGFR antibody comprises a heavy chain and a light chain, each chain having a constant region and a variable region, each variable region comprising framework regions and complementarity determining regions (CDRs), wherein the CDRs have an amino acid sequence set forth below:

```
For the heavy chain:
CDR1
                                    (SEQ ID No. 1)
NYGVH CDR2
                                    (SEQ ID No. 2)
VIWSGGNTD^58YNTPFTS
```

-continued

CDR3 (SEQ ID No. 3)

ALTY$^{101}$Y$^{102}$D$^{103}$YE$^{105}$FAY

For the light chain:
CDR1 (SEQ ID No. 4)

RASQSIGTNIH

CDR2 (SEQ ID No. 5)

ASE$^{53}$SIS

CDR3 (SEQ ID No. 6)

QQNNNW$^{94}$PTT wherein at least one of E$^{53}$, D$^{58}$, W$^{94}$, Y$^{101}$, Y$^{102}$, D$^{103}$, and E$^{105}$ is replaced by a substituting amino acid that reduces the EGFR binding affinity of said antibody. In embodiments, the substituting amino acid(s) are selected to confer on the antibody a binding affinity (Kd) for EGFR that is about 10 fold or more weaker than the EGFR binding affinity of cetuximab.

In embodiments, the present invention provides an EGFR antibody comprising a heavy chain and a light chain, each chain having a constant region and a variable region, wherein the heavy chain variable region comprises the sequence of SEQ ID No. 8 and the light chain variable region comprises the sequence of SEQ ID No. 7, wherein at least one of E$^{53}$, D$^{58}$, W$^{94}$, Y$^{101}$, Y$^{102}$, D$^{103}$, and E$^{105}$ is replaced by a substituting amino acid that reduces the EGFR binding affinity of said antibody.

In other embodiments, the substituting amino acid is selected to reduce EGFR binding affinity of the antibody or bivalent fragment to a level that substantially eliminates binding to cells presenting EGFR at a normal EGFR density, and retains effective binding at targeted disease cells that present EGFR at a greater density relative to normal cell EGFR density.

In still other embodiments, the antibody or bivalent fragment is a variant of cetuximab having one or more substitutions at the residues identified herein. In particular embodiments, the substitutions are non-conservative amino acid substitutions.

In another of its aspects, the present invention provides conjugates, i.e., immunoconjugates, comprising an antibody or bivalent fragment thereof according to the present invention and, conjugated therewith, an agent useful to treat or detect cells presenting EGFR at a density characteristic of disease cells.

In a further aspect, the present invention provides medically useful compositions comprising an antibody, bivalent fragment thereof or immunoconjugate thereof according to the present invention, in combination with a medically acceptable carrier, such as a pharmaceutically acceptable carrier or a diagnostically useful carrier.

In a related aspect, the present invention provides a method for treating a subject having disease cells that present EGFR at a density greater than the EGFR density on normal cells, comprising the step of administering to the subject an effective amount of an antibody, bivalent fragment thereof, or an immunoconjugate of the present invention.

Subjects so treated will manifest adverse events that are fewer in number and/or severity given the reduced affinity of the present antibodies for normal cells and tissue.

These and other aspects of the present invention are now described in greater detail with reference to the accompanying drawings, in which:

REFERENCE TO THE FIGURES

FIG. 1 is a graph showing binding of antibodies to cell surface EGFR present on the surface of (A) parental U87MG cells, (B) U87MGwtEGFR, U87 cells engineered to overexpress wt EGFR, (C) U87MG-EGFRvIII, U87 cells engineered to overexpress EGFR vIII and (D) primary human epidermal keratinocytes (HEK), at 1 and 10 µg/ml mAb (A-C) or 0.1 and 1 µg/ml mAb (D). These can be compared to wt mAb (HC/LC) which was set arbitrarily to 100%. Similarly, FIG. 1-1 (A-B) shows results from these same experiments plus additional experiments, but using a different data presentation approach, i.e. all binding is divided by background binding, (that is, is expressed as a fold change over background binding) rather than background binding being subtracted from all binding values (as was done in FIG. 1). These results demonstrate a greater reduction in binding of some anti-EGFR mAb variants to cells expressing lower EGFR levels (parental U87 or HEK cells) as compared to the reduction observed on U87 cells overexpressing EGFR.

Figure 2:
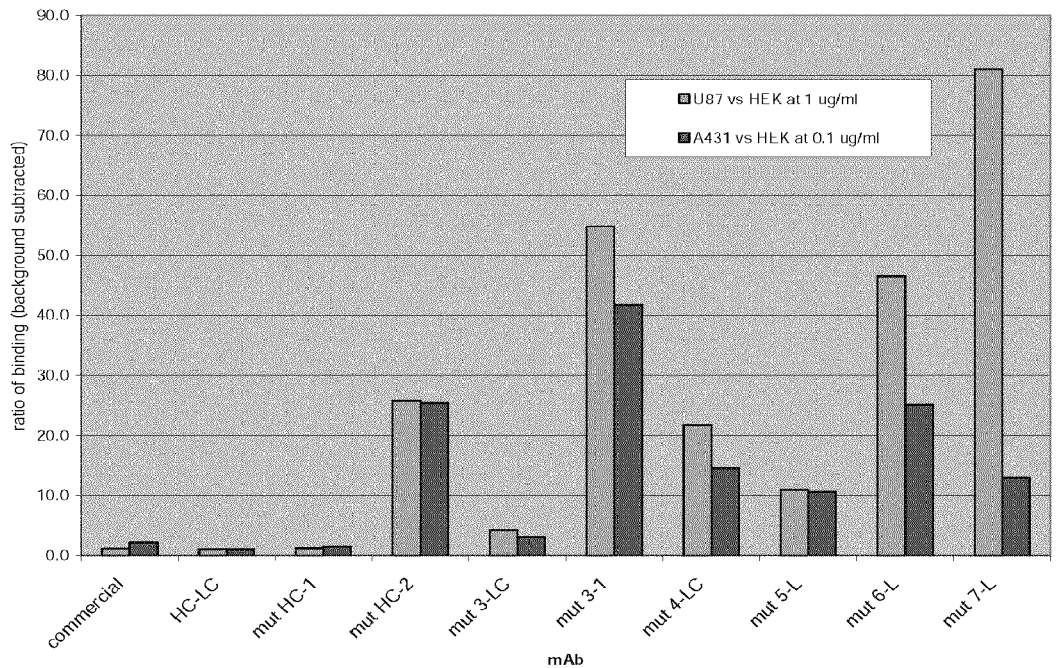
Figures 1, 2:
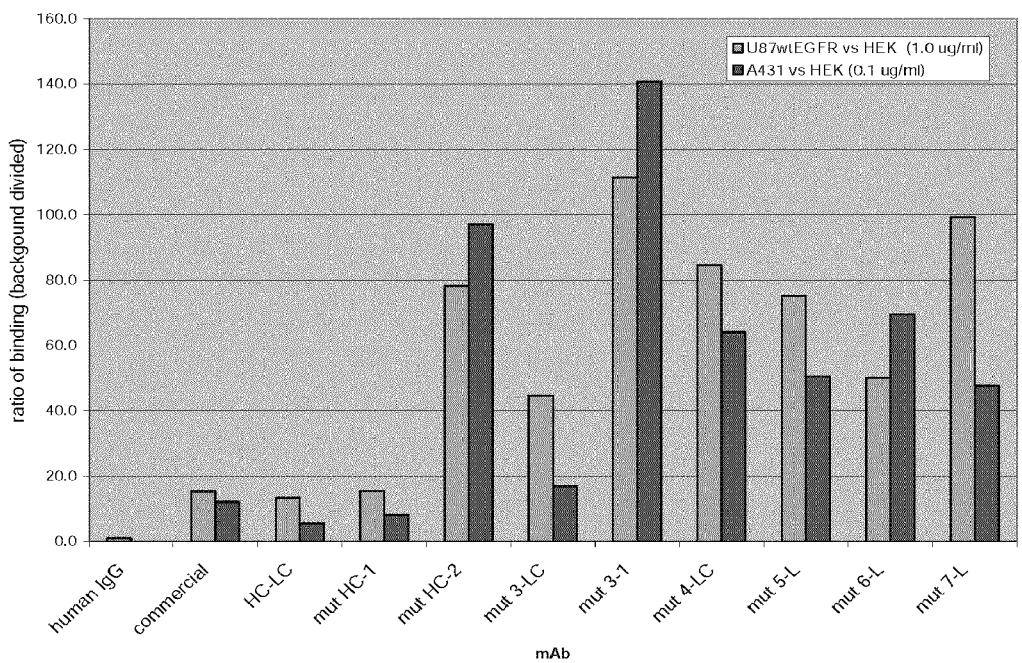

FIG. 2 is a graph representing binding selectivity of antibodies. The ratio of antibody binding (with background subtracted) to EGFR overexpressing cells [U87MGwtEGFR or A431 cells (which naturally overexpress wt EGFR)] relative to antibody binding to normal HEK cells was calculated and compared to that seen with wild type antibody (ratio set arbitrarily to 1 for wt antibody). In FIG. 2-1, the same results as in FIG. 2 are shown using a different data presentation approach, i.e. all binding is divided by background. Note—all additional figures present data analysed in this manner. These results clearly show that some of the EGFR mAbs exhibit better binding to tumor cells that overexpress EGFR relative to normal HEK cells (e.g. mutant HC-2 exhibits a 20-fold (FIG. 2) or 6-fold (FIG. 2-1) better ratio of binding, and mutant 3-1 exhibits a 40-fold (FIG. 2) or 9-fold (FIG. 2-1) better ratio of binding to tumor than normal cells). The pattern of binding specificity was similar amongst the tumor cell lines analyzed (U87MGwt EGFR and A431) suggesting that the selectivity of binding is universally high for tumor cells overexpressing EGFR (~2 million receptors per cell or more).

Figure 3A:
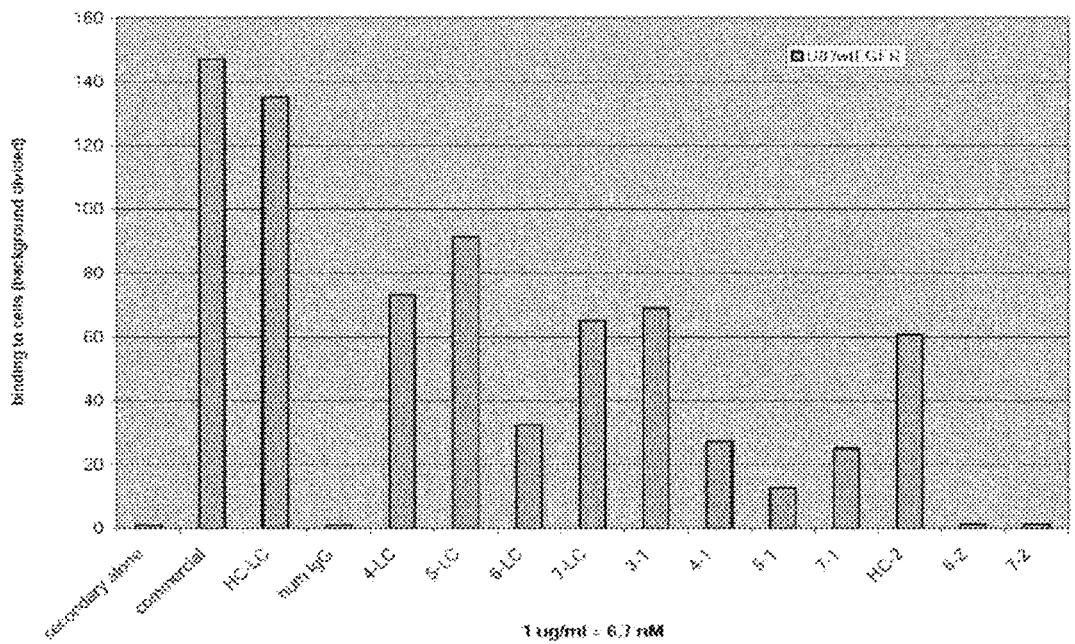
Figure 3B:
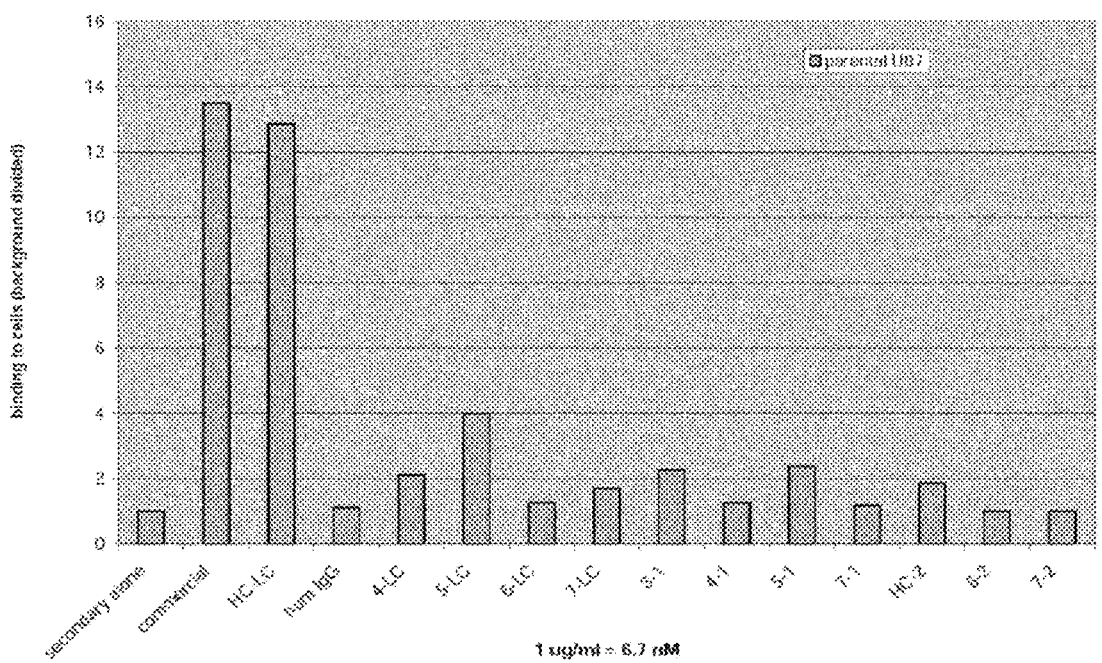
Figure 4:
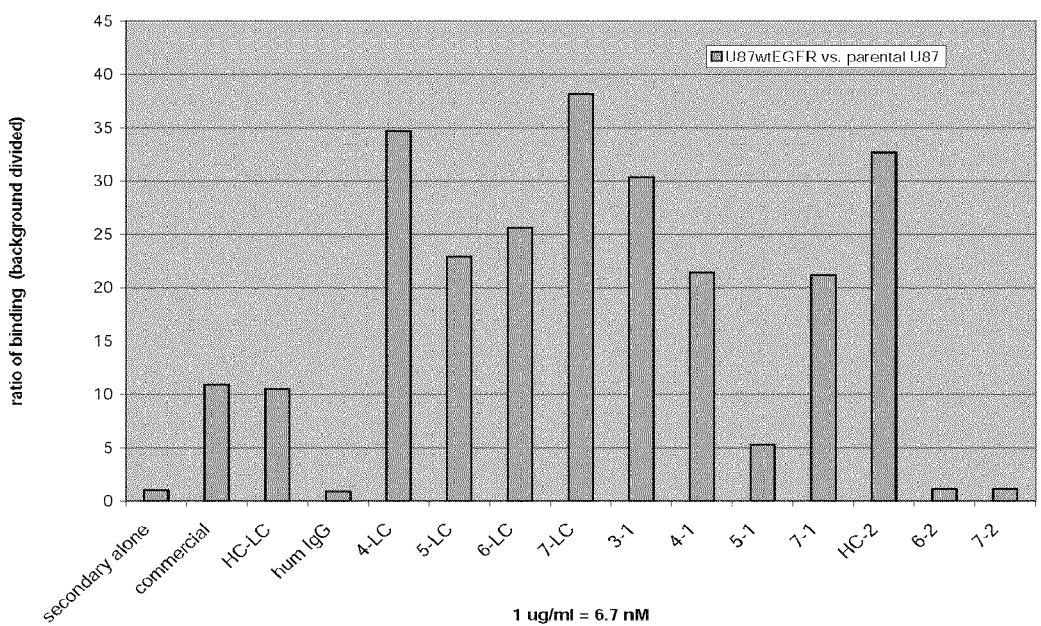

FIG. 3 depicts graphs showing binding of mutated antibodies at 1 ug/ml (6.7 nM) to (A) U87MGwtEGFR, U87 cells overexpressing wt EGFR, (B) parental U87MG cells;

FIG. 4 is a graph illustrating the binding selectivity of antibodies, based on data from FIG. 3. The ratio of antibody binding to EGFR overexpressing cells (U87MGwtEGFR) relative to antibody binding to parental U87MG cells was calculated. This results in a ratio of 11 for wild type antibody binding to U87MGwtEGFR cells versus parental cells; and in ratios of up to 35 for certain mutated antibodies, e.g. mutant 7-LC and 4-LC. In other words, these mutant antibodies show a 3-4 fold better ratio (selectivity) of binding.

Figure 5A:
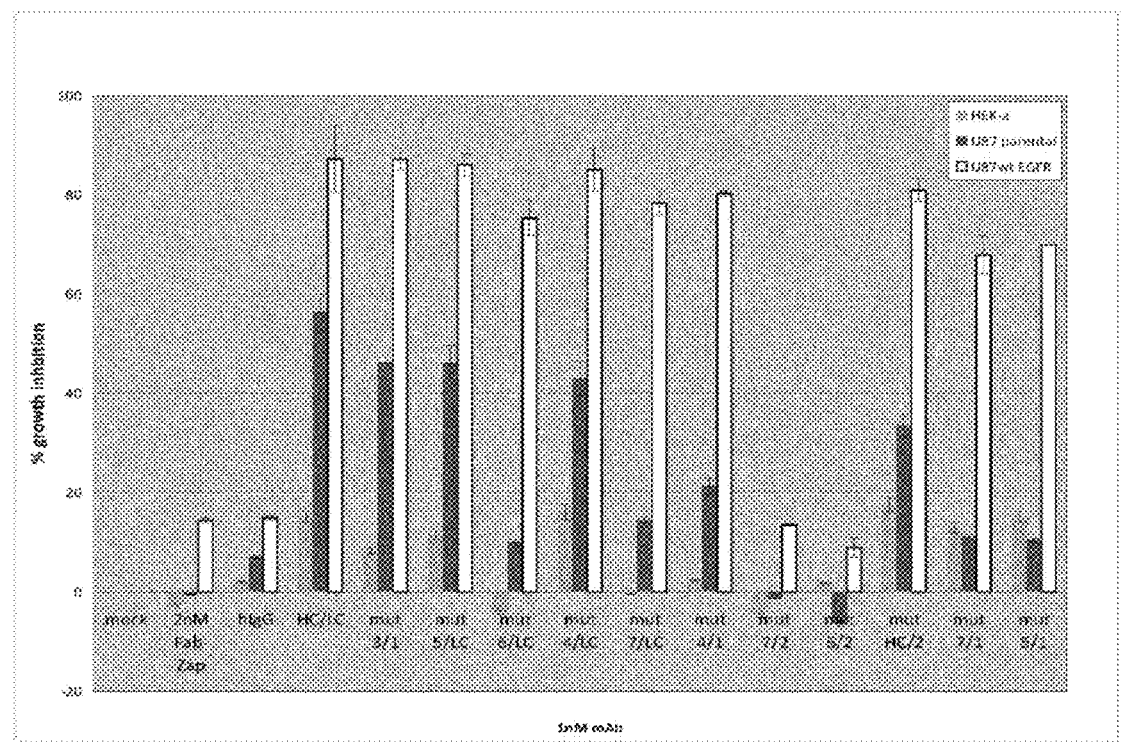
Figure 5B:
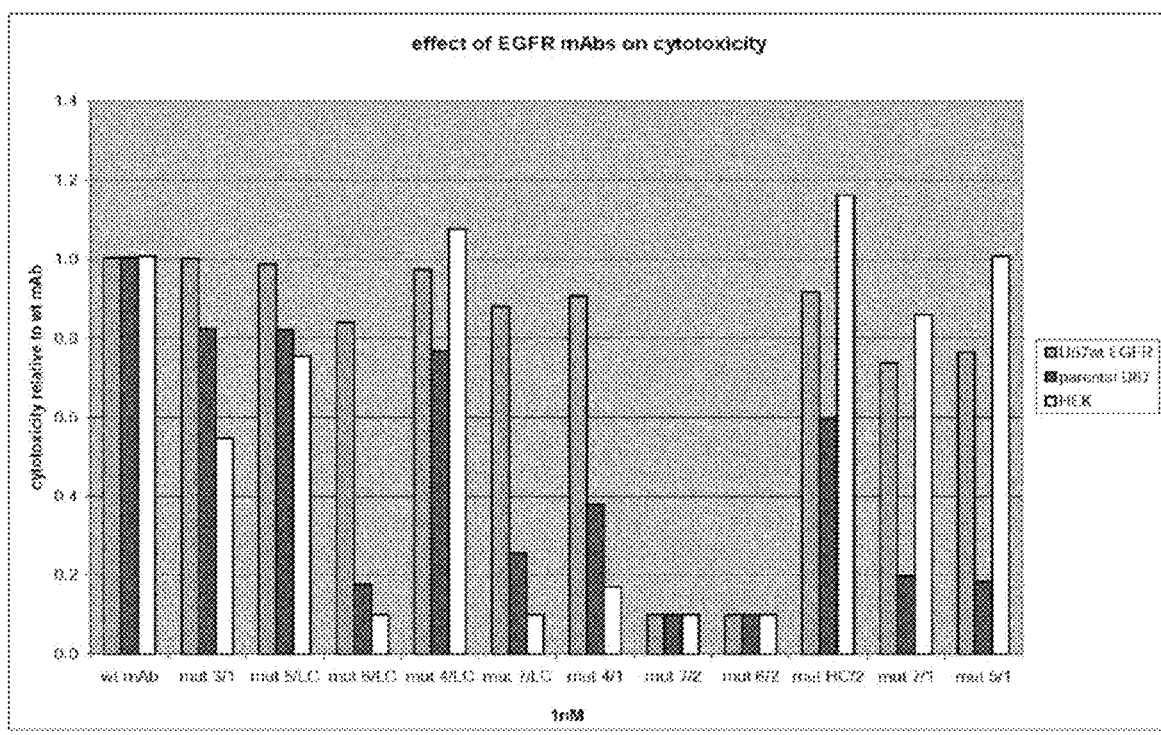

FIG. 5A-B illustrates the ability of the EGFR mAbs to bind cells and deliver a protein toxin, saporin. Specifically, 1 nM EGFR mAbs were incubated with 2 nM anti-human secondary antibody that was chemically conjugated with saporin toxin (Advanced Targeting Systems, San Diego, CA), a ribosome inactivating enzyme that needs to be internalized to cause cell death. The antibody complex was then added to the cell types indicated (plated in triplicate) and their effects on cell viability were measured after 72 hr incubation at 37° C. EGFR directed cytotoxicity can be quantitated following evaluation with controls for non-specific cytotoxicity (no primary or an irrelevant primary antibody (control human IgG) were used).

DETAILED DESCRIPTION OF THE INVENTION AND PREFERRED EMBODIMENTS

As used herein, the term "EGFR" refers to any protein that comprises the expressed and processed product of the her-1 gene, wherein the protein is designated as UniProtKB/Swiss-Prot P04626-1, including antibody-binding variants thereof.

The present invention relates to EGFR antibodies and bivalent fragments thereof that display a preference for binding to disease cells presenting EGFR at a density greater than normal cells. On cells that present EGFR, the normal density of EGFR is generally less than about 10,000 EGFR molecules per cell, and is usually less than about 1,000 EGFR molecules per cell. EGFR-presenting disease cells, on the other hand, present EGFR at a density generally greater than 10,000 EGFR molecules per cell, and usually greater than about 100,000 EGFR molecules per cell. Generally, the EGFR density is thus about $10^3$ or less on normal cells, and about $10^5$ or more on disease cells. The actual number of EGFR molecules on any given cell can be determined by established methods, including the antibody based radiolabeled binding or flow cytometry binding to live cells herein exemplified. The binding avidity of the present antibodies is greater for the higher EGFR density disease cells than for the lower EGFR density normal cells. This greater avidity is revealed conveniently using techniques established for determining affinity constants for antibody-target interactions, also as exemplified herein.

In embodiments, the present EGFR antibodies having a binding affinity for EGFR that is about 10 fold or more weaker than the EGFR binding affinity of cetuximab. Desirably, the binding affinity of the antibody for EGFR is about 15-fold, 20-fold, 25-fold, and preferably 30-fold or more weaker than the EGFR binding affinity of cetuximab. In absolute terms, and given an EGFR binding affinity of about 0.3 nM for cetuximab, the present antibodies incorporate amino acid substitution(s) that reduce their EGFR binding affinity (Kd) to about 1.0 nM and weaker, more desirably about 10 nM and weaker, e.g., to an EGFR binding affinity that is in the range from 1 nM to 1 μM, more desirably 2 nM to 500 nM, such as 10 nM to 500 nM or 10 nM to 100 nM.

In embodiments, the antibody is an intact antibody comprising features common to all natural antibodies, and thus comprises a heavy chain and a light chain, each chain having a constant region and a variable region, each variable region comprising framework regions (FRs) and complementarity determining regions (CDRs). In the alternative, the antibody is provided as a bivalent fragment, i.e., an antibody fragment comprising both "arms" of an intact antibody, joined through a linker that can be represented by the hinge region of the antibody or any equivalent. Such bivalent fragments include F(ab)₂ fragments and any other bivalent fragment that retains preference for high density EGFR. In particular embodiments, the bivalent fragment is a F(ab')₂ fragment, generated for instance by papain-based digestion of the parent antibody using standard procedures for digestion and subsequent fragment isolation. In the alternative, the bivalent fragment can be a so-called single chain Fv (scFv), consisting of the variable light and variable heavy antibody domains joined by an amino acid linker, or a bivalent form of a so-called diabody prepared using a 5 amino acid linker such as SGGGG between the light and heavy chain variable domains and a C-terminal cysteine modification to GGC to give a final diabody product as VL-SGGG-VH-GGC. Still other bivalent fragments can be prepared by coupling the light and heavy chain variable domains through thioether linkages such as bis-maleimidomethyl ether (BMME), N,N'-p-phenylene dimaleimide (PDM and N,N'-bismaleimidohexane BMH), to stabilize the F(ab')₂ fragments.

In the intact antibody or bivalent fragment, the CDRs comprise or consist of the following amino acid sequences:

For the heavy chain:

```
For the heavy chain:
CDR1
                                       (SEQ ID No. 1)
NYGVH CDR2
                                       (SEQ ID No. 2)
VIWSGGNTD⁵⁸YNTPFTS CDR3
                                       (SEQ ID No. 3)
ALTY¹⁰¹Y¹⁰²D¹⁰³YE¹⁰⁵FAY For the light chain:
CDR1
                                       (SEQ ID No. 4)
RASQSIGTNIH CDR2
                                       (SEQ ID No. 5)
ASE⁵³SIS CDR3
                                       (SEQ ID No. 6)
QQNNNW⁹⁴PTT
``` wherein at least one of $E^{53}$, $D^{58}$, $W^{94}$, $Y^{101}$, $Y^{102}$, $D^{103}$, and $E^{105}$ is replaced by a substituting amino acid that reduces the EGFR binding affinity of said antibody or bivalent fragment.

The substituting amino acids are most suitably genetically encoded amino acids that are selected desirably, but not essentially, from an amino acid class that is different from the amino acid class to which the parent amino acid belongs. For instance, in the case of $Y^{101}$ and $Y^{102}$, suitable substituting amino acids are those that are not polar/neutral/large amino acids. The selection process can be conducted by applying computer aided tools that couple saturation virtual mutagenesis engines with algorithms for in silico scoring of binding affinities and/or association rates. Amino acid selections can also be made based on the following Table 1:

| Amino Acid | 3 letter | 1 letter | Polarity (side chain) | Charge (pH 7.4) | Size* |
|---|---|---|---|---|---|
| Alanine | Ala | A | nonpolar | neutral | tiny |
| Arginine | Arg | R | polar | positive | large |
| Asparagine | Asn | N | polar | neutral | small |
| Aspartic acid | Asp | D | polar | negative | small |
| Cysteine | Cys | C | nonpolar | neutral | small |
| Glutamic acid | Glu | E | polar | negative | small |
| Glutamine | Gln | Q | polar | neutral | small |
| Glycine | Gly | G | nonpolar | neutral | tiny |
| Histidine | His | H | polar | neutral (90%) | large |
| Isoleucine | Ile | I | nonpolar | neutral | large |
| Leucine | Leu | L | nonpolar | neutral | large |
| Lysine | Lys | K | polar | positive | large |
| Methionine | Met | M | nonpolar | neutral | large |
| Phenylalanine | Phe | F | nonpolar | neutral | large |
| Proline | Pro | P | non-polar | neutral | small |
| Serine | Ser | S | polar | neutral | tiny |

-continued

| Amino Acid | 3 letter | 1 letter | Polarity (side chain) | Charge (pH 7.4) | Size* |
|---|---|---|---|---|---|
| Threonine | Thr | T | polar | neutral | small |
| Tryptophan | Trp | W | nonpolar | neutral | bulky |
| Tyrosine | Tyr | Y | polar | neutral | large |
| Valine | Val | V | nonpolar | neutral | small |

*based on volume in $A^3$, where 50-100 is tiny, 100-150 is small, 150-200 is large and >200 is bulky It will be appreciated that the conservative amino acid families include (i) G, A, V, L and I; (ii) D and E; (iii) A, S and T; (iv) H, K and R; (v) N and Q; and (vi) F, Y and W.

In embodiments, the heavy chain variable region of the antibody or bivalent fragment incorporates at least one substitution at $D^{58}$ $Y^{101}$, $Y^{102}$, $D^{103}$, or $E^{105}$. In other embodiments, the heavy chain variable region incorporates substitutions at least two such residues, such as at $D^{58}$ and $D^{103}$ or three such residues, such as at $D^{58}$ $D^{103}$ and $E^{105}$ In an alternative embodiment, the heavy chain variable region is wild type and incorporates no such substitutions, provided there is at least one substitution in the light chain variable region.

In embodiments, in the heavy chain CDRs, $Y^{101}$ and/or $Y^{102}$, independently, is replaced by a substituting amino acid having a side chain that is nonpolar and/or a side chain that is non-neutral and/or a side chain that is not large. Desirably, $Y^{101}$ and/or $Y^{102}$ is replaced by an amino acid selected independently from A, C, G, I, L, M, F, W and V; preferably from A, G, I, L and V; and more preferably from A, V, I and L. In a specific embodiment, the tyrosine occurring at one or both of positions 101 and 102 is replaced by alanine, thus yielding the substitutions designated $Y^{101}$ and $Y^{102}A$.

In other embodiments, $D^{58}$ in the heavy chain CDR2 and/or D103 in the heavy chain CDR3 is replaced, independently, by a substituting amino acid having a side chain that is nonpolar and/or is charge neutral or positive and/or is not small. Desirably, $D^{58}$ and/or $D^{103}$ is replaced by an amino acid having a side chain that is charge neutral or positive, as well as polar, as well as small, and is selected desirably from N and Q. In a specific embodiment, $D^{58}$ is replaced by $N^{58}$, thus yielding the substitution designated $D^{58}N$. In another specific embodiment $D^{103}$ is replaced by $N^{103}$, thus yielding the substitution designated $D^{103}N$.

In other embodiments, $E^{105}$ in the heavy chain CDR3 is replaced by a substituting amino acid having a side chain that is nonpolar and/or is charge neutral or positive and/or is not small. Desirably, $E^{105}$ is replaced by an amino acid having a side chain that is charge neutral or positive, as well as polar, as well as small, and is selected desirably from N and Q. In a specific embodiment, $E^{105}$ is replaced by $Q^{105}$, thus yielding the substitution designated $E^{105}Q$.

In embodiments, the light chain variable region of the antibody or bivalent fragment incorporates at least one substitution at $E^{53}$ or at $W^{94}$. In a specific embodiment, the light chain variable region comprises substitutions at both $E^{53}$ or at $W^{94}$. In another specific embodiment, the light chain variable region incorporates substitution only at $E^{53}$, or only at $W^{94}$. In an alternative embodiment, the light chain variable region is wild type and incorporates no such substitutions, provided there is at least one substitution in the heavy chain variable region.

When substituted, $E^{53}$ is replaced by a substituting amino acid having a side chain that is either nonpolar and/or is neutral or positive in charge and/or may not be small. In embodiments, $E^{53}$ is substituted by an amino acid selected from R, D, E, H, or K. In a preferred embodiment, $E^{53}$ is substituted by K, yielding the substitution designated $E^{53}K$.

When substituted, $W^{94}$ is replaced by a substituting amino acid having a side chain that is either polar and/or is charge positive or negative and/or is not bulky. In embodiments, $W^{94}$ is replaced by R, N, D, E, Q, H, K, A, S, T or Y. In particular embodiments, $W^{94}$ is replaced by N, Q, H, S, T, A or Y. In a preferred embodiment, $W^{94}$ is replaced by A, yielding the substitution designated $W^{94}A$.

The antibody or bivalent fragment thereof comprises at least one substitution at a location noted above. The at least one substitution can occur in either the light chain variable region or the heavy chain variable region. In specific embodiments, antibodies comprising single site substitutions include:

An antibody comprising an $E^{53}K$ substitution in CDR2 of the light chain, wherein the CDRs are otherwise the wild type versions specified above; or wherein the light chain is otherwise the wild type version as set out in SEQ ID No. 7, or wherein the antibody is otherwise cetuximab, i.e. [$E^{53}K$]cetuximab.

An antibody comprising a $W^{94}A$ substitution in CDR3 of the light chain, wherein the CDRs are otherwise the wild type versions specified above; or wherein the light chain is otherwise the wild type version as set out in SEQ ID No. 7, or wherein the antibody is otherwise cetuximab, i.e., [$W^{94}A$]cetuximab.

An antibody comprising a $D^{58}N$ substitution in CDR2 of the heavy chain, wherein the CDRs are otherwise the wild type versions specified above; or wherein the heavy chain is otherwise the wild type version as set out in SEQ ID No. 8, or wherein the antibody is otherwise cetuximab, i.e., [$D^{58}N$]cetuximab.

An antibody comprising a $Y^{101}A$ substitution in CDR3 of the heavy chain, wherein the CDRs are otherwise the wild type versions specified above; or wherein the heavy chain is otherwise the wild type version as set out in SEQ ID No. 8, or wherein the antibody is otherwise cetuximab, i.e., [$Y^{101}A$] cetuximab.

An antibody comprising a $Y^{102}A$ substitution in CDR3 of the heavy chain, wherein the CDRs are otherwise the wild type versions specified above; or wherein the heavy chain is otherwise the wild type version as set out in SEQ ID No. 8, or wherein the antibody is otherwise cetuximab, i.e [$Y^{102}A$] cetuximab.

An antibody comprising a $D^{103}N$ substitution in CDR3 of the heavy chain, wherein the CDRs are otherwise the wild type versions specified above; or wherein the heavy chain is otherwise the wild type version as set out in SEQ ID No. 8, or wherein the antibody is otherwise cetuximab, i.e., [$D^{103}N$]cetuximab.

An antibody comprising an $E^{105}Q$ substitution in CDR3 of the heavy chain, wherein the CDRs are otherwise the wild type versions specified above; or wherein the heavy chain is otherwise the wild type version as set out in SEQ ID No. 8, or wherein the antibody is otherwise cetuximab, i.e., [$E^{105}Q$]cetuximab.

In other embodiments, the antibody or binding fragment thereof comprises at least two such substitutions, either in the light chain variable region, in the heavy chain variable region, or at least one substitution in each of the light and heavy chain variable regions. In specific embodiments, antibodies including at least two such substitutions include:

An antibody comprising both a $E^{53}K$ substitution in CDR2 of the light chain and a $Y^{101}A$ substitution in CDR3 of the heavy chain, wherein the CDRs are otherwise the wild type versions specified above; or wherein the heavy chain is otherwise the wild type version as set out in SEQ ID No. 8, or wherein the antibody is otherwise cetuximab, i.e., [E$^{53}$K, Y$^{101}$A] cetuximab.

An antibody comprising both a E53K substitution in CDR2 of the light chain and a Y102A substitution in CDR3 of the heavy chain, wherein the CDRs are otherwise the wild type versions specified above; or wherein the heavy chain is otherwise the wild type version as set out in SEQ ID No. 8, or wherein the antibody is otherwise cetuximab, i.e., [E53K, Y102A] cetuximab An antibody comprising both a D$^{58}$N substitution in CDR2 of the heavy chain, and a D$^{103}$N substitution in CDR3 of the heavy chain, wherein the CDRs are otherwise the wild type versions specified above; or wherein the heavy chain is otherwise the wild type version as set out in SEQ ID No. 8, or wherein the antibody is otherwise cetuximab, i.e., [D$^{58}$N, D$^{103}$N] cetuximab.

An antibody comprising at least three substitutions, including a D$^{58}$N substitution in CDR2 of the heavy chain, a D$^{103}$N substitution in CDR3 of the heavy chain, and an E$^{105}$Q substitution in CDR3 of the heavy chain, wherein the CDRs are otherwise the wild type versions specified above; or wherein the heavy chain is otherwise the wild type version as set out in SEQ ID No. 8, or wherein the antibody is otherwise cetuximab, i.e., [D$^{58}$N, D$^{103}$N, E$^{105}$Q]cetuximab.

In preferred embodiments, the antibody is one of [E53K, Y102A]cetuximab, [D58N, D103N]cetuximab, or [D58N, D103N, E105Q]cetuximab.

In addition to the recited three CDRs present in each of the light and heavy chain variable regions, the heavy and light chains of the intact antibody comprise four intervening framework regions that present the CDRs in a conformation suitable for EGFR binding, and constant regions that confer antibody effector function. The CDRs can be integrated into any suitable acceptor antibody, by grafting the present CDRs into the acceptor antibody, in accordance with practices and techniques well established for the production of chimeric, humanized and human antibodies.

Particularly suitable acceptor antibodies are antibodies already known to have EGFR binding affinity. Such donor antibodies are most desirably of human origin, but they can also derive from acceptor antibodies of non-human origin, including mouse, rat, rabbit, goat, sheep, primate and the like. It will be appreciated that human antibody acceptor sequences different from those exemplified herein can be identified and used to accommodate the presently desired CDRs. This is achieved by modeling the structure of a preferred antibody using for instance the Swiss-Model (swissmodel.expasy.org/repository) or similar software and selecting, from among the numerous human antibody sequences available in public databases, a human acceptor antibody sequence that, with CDR sequences altered as herein preferred, approximates the same structural conformation as the preferred antibodies. In embodiments, the acceptor antibodies, and the resulting present antibodies, are of the IgG1 isotype, but they may also be IgG2 or IgG4. Moreover, the isotype of the antibody, as dictated by the constant region, can be manipulated to alter or eliminate the effector function of the resulting antibody. That is, the constant region of the present antibodies is either wild type human antibody constant region, or a variant thereof that incorporates amino acid modifications, i.e., amino acid additions, substitutions or deletions that alter the effector function of the constant region, such as to enhance serum half-life, reduce complement fixation, reduce antigen-dependent cellular cytotoxicity and improve antibody stability. The number of amino acid modifications in the constant region is usually not more than 20, such as 1-10 e.g., 1-5 modifications, including conservative amino acid substitutions.

In embodiments, the half life of the antibody is improved by incorporating one more amino acid modification, usually in the form of amino acid substitutions, for instance at residue 252, e.g., to introduce Thr, at residue 254, e.g., to introduce Ser, and/or at residue 256 e.g., to introduce Phe. Still other modifications can be made to improve half-life, such as by altering the CH1 or CL region to introduce a salvage receptor motif, such as that found in the two loops of a CH2 domain of an Fc region of an IgG. Such alterations are described for instance in U.S. Pat. Nos. 5,869,046 and 6,121,022.

Altered C1q binding, or reduced complement dependent cytotoxicity, can be introduced by altering constant region amino acids at locations 329, 331 and 322, as described in U.S. Pat. No. 6,194,551. The ability of the antibody to fix complement can further be altered by introducing substitutions at positions 231 and 239 of the constant region, as described in WO94/029351.

The framework regions of the light and heavy chains of the present antibodies and fragments also desirably have the sequence of a human antibody variable region, but incorporating the CDRs herein specified. In embodiments, the heavy chain variable region is human IgG4 in origin. In specific embodiments, the heavy chain variable region is that of human IgG, such as the human IgG1 antibody variant having the sequence designated Genbank gi 2414502. Alternatively, and preferably, the heavy chain variable region is that of human IgG4 antibody species designated Genbank gi 2414502.

The framework regions of the heavy and light chains of the present antibodies may also incorporate amino acid modifications, i.e., amino acid deletions, additions or substitutions, which further improve upon the properties of the antibody or fragment, in accordance with techniques established for antibody humanization. Such framework modifications can be modeled on the framework regions of antibody sequences provided in public databases, and on framework regions of antibodies known to bind EGFR, such as those antibodies referenced in the background section hereof Preferred framework substitutions are those which yield antibodies having a greater preference for binding EGFR at the higher density associated with disease cells, relative to normal cells.

Framework modifications can also be made to reduce immunogenicity of the antibody or to reduce or remove T cell epitopes that reside therein, as described for instance by Carr et al in US2003/0153043.

In accordance with embodiments of the present invention, the heavy and light chain variable regions are modeled on the antibody cetuximab, and comprise a heavy chain variable region of SEQ ID No. 8, and/or a light chain variable region having SEQ ID No. 7, as follows:

```
Light chain variable region (VL):
                              [SEQ ID No. 7]
DILLTQSPVILSVSPGERVSFSCRASQSIGTNIHWYQQRTNGSPRL

LIKYASE⁵³SISGIPSRFSGSGSGTDFTLSINSVESEDIADYYCQQ

NNNW⁹⁴PTTFGAGTKLELK;
wherein E⁵³ or W⁹⁴ are as defined hereinabove;
```

```
-continued
Heavy chain variable region (VH):
                                            [SEQ ID No. 8]
QVQLKQSGPGLVQPSQSLSITCTVSGFSLTNYGVHWVRQSPGKGLE

WLGVIWSGGNTD⁵⁸YNTPFTSRLSINKDNSKSQVFFKMNSLQSNDT

AIYYCARALTY¹⁰¹Y¹⁰²D¹⁰³YE¹⁰⁵FAYWGQGTLVTVSA;
wherein D⁵⁸, Y¹⁰¹, Y¹⁰², D¹⁰³, or E¹⁰⁵ are as
defined hereinabove.
```

In more specific and preferred embodiments, the entire light and heavy chains of the intact antibody are set out below as SEQ ID Nos. 9 and 10, respectively:

```
Entire Light chain:
                                            [SEQ ID No. 9]
DILLTQSPVILSVSPGERVSFSCRASQSIGTNIHWYQQRTNGSPRL

LIKYASE⁵³SISGIPSRFSGSGSGTDFTLSINSVESEDIADYYCQQ

NNNW⁹⁴PTTFGAGTKLELKRTVAAPSVFIFPPSDEQLKSGTASVVC

LLNNFYPREAKVQWKVDNALQSGNSQESVTEQDSKDSTYSLSSTLT

LSKADYEKHKVYACEVTHQGLSSPVTKSFNRGE;
wherein E⁵³ and W⁹⁴ are as defined hereinabove;

Entire Heavy chain.
                                           [SEQ ID No. 10]
QVQLKQSGPGLVQPSQSLSITCTVSGESLTNYGVHWVRQSPGKGLE

WLGVIWSGGNTD58YNTPFTSRLSINKDNSKSQVFFKMNSLQSNDT

AIYYCARALTY¹⁰¹Y¹⁰²D¹⁰³YE¹⁰⁵FAYWGQGTLVTVSAASTKG

PSVFPLAPSSKSTSGGTAALGCLVKDYFPEPVTVSWNSGALTSGVH

TFPAVLQSSGLYSLSSVVTVPSSSLGTQTYICNVNHKPSNTKVDKR

VEPKSCDKTHTCPPCPAPELLGGPSVFLFPPKPKDTLMISRTPEVT

CVVVDVSHEDPEVKFNWYVDGVEVHNAKTKPREEQYNSTYRVVSVL

TVLHQDWLNGKEYKCKVSNKALPAPIEKTISKAKGQPREPQVYTLP

PSRDELTKNQVSLTCLVKGFYPSDIAVEWESNGQPENNYKTTPPVL

DSDGSFFLYSKLTVDKSRWQQGNVFSCSVMHEALHNHYTQKSLSLS

PGK;
wherein D⁵⁸, Y¹⁰¹, Y¹⁰², D¹⁰³, or E¹⁰⁵ are as
defined hereinabove.
```

As noted, final selection of an antibody or binding fragment is made based on the binding preference displayed by the desired antibody or bivalent fragment for cells that present EGFR at a density greater than normal. The target cells are thus disease cells presenting greater than normal EGFR density, as a hallmark. Screening can be performed in vitro, as exemplified herein, using as reference cells a first disease cell known from analysis to present EGFR at a density greater than normal, such as the U87wtEGFR or related lines that incorporate an altered EGFR such as U87EGFRvIII or the line A431, and a second, normal cell known from analysis to present EGFR at a normal density, such as primary human epidermal keratinocytes (~20,000 EGFR/cell). The choice of epidermal keratinocytes as the reference, normal cell is prudent, given that marketed EGFR antibodies, such as cetuximab, are known to elicit severe skin rash side effects through their interaction with these cells. Any other human cell line that presents EGFR at normal density can be used, in the alternative.

The cell-based assay can use flow cytometry with appropriate EGFR antibody and labeled secondary antibody to report and measure binding affinity and avidity, as exemplified herein. In the alterative, selection of the desired antibody can be performed based on absolute binding affinities obtained for instance using surface plasmon resonance, also as exemplified herein.

For purposes of identifying disease cells that can be targeted by the present EGFR antibodies and bivalent fragments, the commercial test EGFRpharmDX (DAKO) can conveniently be used. This is a semi-quantitative immunohistochemical assay for determination of her-1 protein overexpression in colorectal tissues. Positive or negative results aid in the classification of abnormal cells/tissues and provide a basis for treatment with EGFR antibody.

The antibodies and binding fragments thus are useful both for diagnostic purposes, including sample testing and in vivo imaging, and for therapeutic purposes to treat diseases in which EGFR density is increased on disease cells.

For either purpose, the antibody or binding fragment can be conjugated to an appropriate agent, to form an immunoconjugate. Agents appropriate for treating disease include cytotoxic agents include chemotherapeutics and radiotherapeutics. For diagnostic purposes, appropriate agents are detectable labels that include radioisotopes, for whole body imaging, and radioisotopes, enzymes, fluorescent labels and the like for sample testing.

For therapy, the cytotoxin may be conjugated with the antibody or bivalent binding fragment through non-covalent interaction, but more desirably, arc coupled by covalent linkage either directly or, more preferably, through a suitable linker. In a preferred embodiment, the conjugate comprises a cytotoxin and an antibody. Immunoconjugates of the antibody and cytotoxin are made using a variety of bifunctional protein coupling agents such as N-succinimidyl-3-(2-pyridyldithiol) propionate, iminothiolane, biflinctional derivatives of imidoesters such as dimethyl adipimidate HCL, active esters such as disuccinimidyl suberate, aldehydes such as glutaraldehyde, bis-azido compounds such as bis-(p-diazoniumbenzoyl)-ethylenediamine), diisocyanates such as toluene 2,6-diisocyanate, and bis-active fluorine compounds (such as 1,5-difluoro-2,4-dinitrobenzene). Carbon-14-labeled 1-isothiocyanobenzyl-3-methyldiethylene triaminepentaacetic acid (MX-DTPA) is a chelating agent suitable for conjugation of radio nucleotide to the antibody.

The cytotoxin component of the immunoconjugate can be a chemotherapeutic agent, a toxin such as an enzymatically active toxin of bacterial, fungal, plant or animal origin, or fragments thereof, or a small molecule toxin, or a radioactive isotope such as $^{212}$Bi, $^{131}$I $^{131}$In $^{111}$In, $^{90}$Y and $^{186}$Re, or any other agent that acts to inhibit the growth or proliferation of a cancer cell.

Chemotherapeutic agents useful in the generation of such immunoconjugates include adriamycin, doxombicin, epirubicin, 5-fluoroouracil, cytosine arabinoside ("Ara-C"), cyclophosphamide, thiotepa, busulfan, cytoxin, taxoids, e.g. paclitaxel, and docetaxel, taxotere, methotrexate, cisplatin, melphalan, vinblastine, bleomycin, etoposide, ifosgamide, mitomycin C, mitoxantrone, vincristine, vinorelbine, carboplatin, teniposide, daunomycin, carminomycin, aminopterin, dactinomycin, mitomycins, esperamicins, 5-FU, 6-thioguanine, 6-mercaptopurine, actinomycin D, VP-16, chlorambucil, melphalan, and other related nitrogen mustards. Also included arc hormonal agents that act to regulate or inhibit hormone action on tumors such as tamoxifen and onapristone. Toxins and fragments thereof which can be used include diphtheria A chain, nonbonding active fragments of diphtheria toxin, cholera toxin, botulinus toxin, exotoxin A chain (from *Pseudomonas aeruginosa*), ricin A chain, abrin A chain, modeccin A chain, alpha-sarcin, *Aleurites fordii* proteins, dianthin proteins, phytolaca Americana proteins (PAPI, PAPII, and PAP-S), *Momordica charantia* inhibitor, curcin, crotin, sapaonaria, officinalis inhibitor, gclonin, saporin, mitogcllin, restrictocin, phenomycin, cnomycin, and the tricothcenes. Small molecule toxins include, for example, calicheamicins, maytansinoids, palytoxin and CC1065.

Therapeutic formulations of the antibody, bivalent fragment or the conjugate are prepared for storage by mixing the antibody or conjugate having the desired degree of purity with optional pharmaceutically acceptable carriers, excipients or stabilizers (Remington's Pharmaceutical Sciences, $16^{th}$ edition, Osol, A. Ed. [1980]), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl, or benzyl alcohol; alkyl parabens such as methyl or propyl paraben; catechol; resorcinol; cyclohexanol; 3-pentanol; and m-cresol); low molecular weight (less than about 10 residues) polypeptides; proteins such as serum, albumin, gelatin, or immunoglobulins; hydrophilic polymers such as polyvinylpyrrolidone; amino acids such as glycine, glutamine, asparagines, histidine, arginine or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN, PLURONICS or polyethylene glycol (PEG).

The active ingredients to be used for in vivo administration must be sterile. This is readily accomplished by filtration through sterile filtration membranes.

Sustained-release preparations may be prepared. Suitable examples of sustained-release include semipermeable matrices of solid hydrophobic polymers containing the antibody, which matrices are in the form of shapes articles, e.g., films or microcapsules. Examples of sustained-release matrices include polyesters, hydrogels (for example, poly (2-hydroxyethyl-methacrylate), polylactides (U.S. Pat. No. 3,773, 919), copolymers of L-glutamic acid and ethyl-L-glutamate, non-degradable ethylene-vinyl acetate, degradable lactic acid-glycolic acid copolymers such as injectable microspheres composed of lactic acid-glycolic acid copolymer and leuprolide acetate, and poly-D-(–)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Administration "in combination with" one or more further therapeutic agents includes simultaneous (concurrent) and consecutive administration in any order. Other therapeutic regimens may be combined with the administration of the anti-cancer agents, e.g., antibodies or conjugates, of the instant invention. For example, the patient to be treated with such anti-cancer agents may also receive radiation therapy, such as external beam radiation. Alternatively, or in addition, a chemotherapeutic agent may be administered to the patient. Preparation and dosing schedules for such chemotherapeutic agents may be used according to manufacturers' instructions or as determined empirically by the skilled practitioner. Preparation and dosing schedules for such chemotherapy are also described in Chemotherapy Service Ed., M. C. Perry, Williams & Wilkins, Baltimore, Md. (1992). The chemotherapeutic agent may precede, or follow administration or the anti-tumor agent, e.g., antibody, or may be given simultaneously therewith. The antibody may be combined with any of the toxins described above with reference to the conjugates, or any other suitable drug particularly include irinotecan (CPT-11), cisplatin, cyclophosphamide, melphalan, dacarbazine, doxorubicin, daunorubicin, and topotecan, as well as tyrosine kinase inhibitors.

It may be desirable to also administer antibodies or conjugates against other tumor associated antigens or their ligands, such as antibodies which bind to the ErbB2, ErbB3, ErbB4, or vascular endothelial factor (VEGF), and/or antibodies that bind to EGF or TGFα. Alternatively, or in addition, two or more antibodies binding that same or two or more different antigens disclosed herein may be co-administered to the patient. Sometimes it may be beneficial to also administer one or more cytokines to the patient. In a preferred embodiment, the antibodies herein are co-administered with a growth inhibitory agent. For example, the growth inhibitory agent may be administered first, followed by an antibody of the present invention. However, simultaneous administration or administration of the antibody of the present invention first is also contemplated. Suitable dosages for the growth inhibitory agent arc those presently used and may be lowered due to combined action (synergy) of the growth inhibitory agent and the antibody herein.

In another embodiment of the invention, an article of manufacture containing materials useful for the diagnosis or treatment of the disorders described herein is provided. The article of manufacture comprises a container and a label. Suitable containers include, for example, bottles, vials, syringes, and test tubes. The containers may be formed from a variety of materials such as glass or plastic. The container holds a composition which is effective for treating the condition and may have a sterile access port (for example the container may be an intravenous solution bag or vial having a stopper pierce able by a hypodermic injection needle). The label on, or associated with, the container indicates that the composition is used for treating a cancer condition. The article of manufacture may further compromise a second container compromising a pharmaceutically-acceptable buffer, such as phosphate-buffered saline, Ringer's solution and dextrose solution. It may further include other matters desirable from a commercial and use standpoint, including other buffers, diluents, filters, needles, syringes, and package inserts with instructions for use.

An anti-cancer therapeutic according to the invention may be administered with a pharmaceutically-acceptable diluent, carrier, or excipient, in unit dosage form. Any appropriate route of administration can be employed, for example, parenteral, intravenous, subcutaneous, intramuscular, intracranial, intraorbital, ophthalmic, intraventricular, intracapsular, intraspinal, intracisternal, intraperitoneal, intranasal, aerosol, or oral administration.

For the treatment of subjects presenting with cancer cells presenting EGFR at greater density than normal cells, the appropriate dosage of an anti-tumor agent, e.g., an antibody, fragment or conjugate, will depend on the type of disease to be treated, as defined above, the severity and course of the disease, whether the agent is administered for preventative or therapeutic purposes, previous therapy, the patients clinical history and response to the agent, and the discretion of the attending physician. The agent is suitably administered to the patient at one time or over a series of treatments. For example, depending on the type and severity of the disease, about 1 µg/kg to 15 mg/kg (e.g., 0.1-20 mg/kg) of antibody or conjugate is a candidate dosage for administration to the patient, whether, for example, by one or more separate administrations, or by continuous infusion. A typical daily dosage might range from about 1 µg/kg to 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays.

It will thus be appreciated that an effective amount of the antibody, fragment or immunoconjugate is an amount effective alone or as part of a treatment regimen that retards or inhibits the growth or proliferation of disease cells presenting with higher than normal EGFR density.

In embodiments, the present antibodies are administered by intravenous infusion, such as at an initial dose of 4 mg/kg over 90 minutes, then 2 mg/kg over 30 minutes, once weekly for 52 weeks, with follow up as required.

The antibody and bivalent fragments are useful in the treatment of a variety of cancers, to inhibit the growth or proliferation of cancer cells and tumours comprising them, including hematopoietic cell cancers and solid tumours. Conditions or disorders to be treated include benign or malignant tumors (e.g., renal, liver, kidney, bladder, breast, gastric, ovarian, colorectal, prostate, pancreatic, lung, vulva, and thyroid); hepatic carcinomas; sarcomas; glioblastomas; and various head and neck tumors; leukemias and lymphoid malignancies. In particular embodiments, the antibody or bivalent fragment are used in the treatment of such cancer cells that express high density EGFR, as determined by the screening assays herein described. In particular embodiments, the cancer cells are EGFR-presenting cancer cells that include head and neck cancers and especially squamous cell carcinoma of the head and neck, colorectal cancers, gastrointestinal cancers, brain tumours including glioblastomas, and tumours of the lung including non-small-cell lung carcinoma, and of the breast, pancreas, esophagus, kidney, ovary, cervix and prostate.

It will be appreciated that subjects who could benefit from the present method include mammals including humans as well as livestock, and pets.

Antibodies and bivalent fragments thereof that bind selectively to the target antigen, e.g. EGFR, are used, in accordance with an aspect of the invention, to screen cancer cells to detect those which present the EGFR antigen at high density. In a preferred embodiment, screening is applied to a sample of cancer cells taken from a subject that is a candidate for EGFR antibody therapy. Subjects testing positive for cancer cells that present the EGFR antigen at high density can then be scheduled for therapy with the present antibody or fragment, or an immunoconjugate thereof. Standard techniques, combined with the antibodies or other binding agents herein described, can be used to screen cancer cells. Desirably, the antibodies incorporate a detectable label. The label may be detectable by itself (e.g., radio-isotope labels or fluorescent labels) or, in the case of an enzymatic label, may catalyze chemical alteration of a substrate compound or composition which is detectable. Radionuclides that can serve as detectable labels include, for example, I-131, I-123, I-125, Y-90, Re-188, Re-186, At-211, Cu-67, Bi-212, and Pd-109.

In situ detection of the binding to cancer cells bearing high density EGFR can be performed, using the present antibody or fragment, by immunofluorescence or immunoelectron microscopy. For this purpose, a histological specimen is removed from the patient, and a labeled form of the present antibody is applied to it, preferably by overlaying the antibody on a biological sample. This procedure also allows for distribution of the EGFR antigen to be examined within biopsied tumour tissue, to reveal only those sites at which the antigen is presented at a density higher than normal. It will be apparent for those skilled in the art that a wide variety of histological methods are readily available for in situ detection.

More particularly, EGFR antibodies or binding fragments of the present invention may be used to monitor the presence or absence of antibody reactivity in a biological sample (e.g., a tissue biopsy, a cell, or fluid) using standard detection assays. Immunological assays may involve direct detection, and are particularly suited for screening large amounts of samples for the presence of cancer cells that overexpress EGFR. For example, antibodies may be used in any standard immunoassay format (e.g., ELISA, Western blot, immunoprecipitation, flow cytometry or RIA assay) to measure complex formation. Any appropriate label which may be directly or indirectly visualized may be utilized in these detection assays including, without limitation, any radioactive, fluorescent, chromogenic (e.g., alkaline phosphatase or horseradish peroxidase), or chemiluminescent label, or hapten (for example, digoxigenin or biotin) which may be visualized using a labeled, hapten-specific antibody or other binding partner (e.g., avidin). Exemplary immunoassays are described, e.g., in Ausubel et al., supra, Harlow and Lane, Antibodies: A Laboratory Approach, Cold Spring Harbor Laboratory, New York (1988), and Moynagh and Schimmel, Nature 400:105, 1999. For example, using the antibodies described herein, high density EGFR is readily detected at the cell surface using standard flow cytometry methods. Samples found to contain labeled complex compared to appropriate control samples are taken as indicating the presence of high density EGFR, and are thus indicative of a cancer or other disease amenable to treatment with the present antibodies.

The present antibody is produced suitably by recombinant DNA means, as exemplified herein. For production, there is provided a DNA molecule that encodes the heavy chain of the present antibody, and a DNA molecule that encodes the light chain thereof. The DNA further encodes any suitable signal peptide suitable for expression of a secretable chain precursor that enables proper externalization with folding and disulfide formation to elaborate the desired antibody as a secreted, dimerized and processed protein. To this end, the present invention provides, in one embodiment, a polynucleotide comprising a sequence that encodes the variable region of the light chain of a presently preferred EGFR antibody, as set out in SEQ ID No. 9 appearing at the end of the disclosure. Also provided, in another embodiment, is a polynucleotide comprising a sequence that encodes the variable region of the heavy chain of a presently preferred EGFR antibody, as set out in SEQ ID No. 10 also appearing at the end of the disclosure.

In more specific embodiments, the present invention provides a polynucleotide that encodes the entire light chain (SEQ ID No. 11) and the entire heavy chain (SEQ ID No. 14) of a preferred EGFR antibody of the present invention. These sequences also are provided at the end of this disclosure.

It will be appreciated that polynucleotide equivalents also can be used, in which synonymous codons are replaced within the sequences provided, to produce the present antibodies.

In embodiments, there are also provided vectors that comprise polynucleotides that encode the heavy chain or the variable region thereof and that encode the light chain or the variable region thereof. To express the antibodies, the polynucleotides are incorporated operably within expression vectors, i.e., operatively linked to transcriptional and translational control sequences. Expression vectors include plasmids, retroviruses, cosmids, and the like. The expression vector and expression control sequences are chosen to be compatible with the expression host cell used. The antibody light chain gene and the antibody heavy chain gene can be inserted into separate vectors. In a preferred embodiment, both genes are inserted into the same expression vector. The antibody genes are inserted into the expression vector by standard methods (e.g., ligation of complementary restriction sites on the antibody gene fragment and vector, or blunt end ligation if no restriction sites are present).

A convenient vector is one that encodes a functionally complete human CH or CL immunoglobulin sequence, with appropriate restriction sites engineered so that any VH or VL sequence can be easily inserted and expressed, as described above. In such vectors, splicing usually occurs between the splice donor site in the inserted J region, and the splice acceptor site preceding the human C region, and also at the splice regions that occur within the human CH exons. Polyadenylation and transcription termination occur at native chromosomal sites downstream of the coding regions. The recombinant expression vector can also encode a signal peptide that facilitates secretion of the antibody chain from a host cell. The antibody chain gene may be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

Polynucleotides encoding the heavy chain and/or the light chain, and vectors comprising these can be used for transformation of a suitable mammalian host cell. Methods for introduction of heterologous polynucleotides into mammalian calls include dextran-mediated transfection, calcium phosphate precipitation, polybrene-mediated transfection, protoplast fusion, electroporation, encapsulation of the polynucleotide(s) in liposomes, biolistic injection and direct microinjection of the DNA into nuclei. In addition, polynucleotides may be introduced into mammalian cells by viral vectors. Mammalian cell lines useful as hosts for expression of the antibody-encoding polynucleotides include many immortalized cell lines available from the American Type Culture Collection (ATCC). These include, inter alia, Chine hamster ovary (CHO) cells, NSO, SP2 cells, HeLa cells, baby hamster kidney (BHK) cells, monkey kidney cells (COS, human hepatocellular carcinoma cells (e.g., Hep G2), A549 cells, 3T3 cells, and a number of other cell lines. Mammalian host cells include human, mouse, rat, dog, monkey, pig, goat, bovine, horse, and hamster cells. Cell lines of particular preference are selected through determining which cell lines have high expression levels. Other cell lines that may be used are insect cell lines, such as S19 cells, amphibian cells, bacterial cells, plant cells and fungal cells. When recombinant expression vectors encoding the heavy chain or antigen-binding portion thereof are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods. It is likely that antibodies expressed by different cell lines or in transgenic animals will have different glycosylation from each other. However, all antibodies encoded by the polynucleotides provided herein, or comprising the amino acid sequences provided herein are part of the instant invention.

Embodiments are now described in the following examples.

EXAMPLES

The structure of cetuximab bound to EGFR [1] was used as starting point for mutant design. Mutations were introduced only in the CDR regions of the light and heavy chain. First, single-point mutations were generated and evaluated computationally. Virtual mutagenesis was carried out with optional conformational relaxation upon mutation by means of conformational sampling algorithms, such as Monte Carlo minimization [2]. Prediction of antigen-antibody relative binding affinities between parent and mutant antibodies was carried out with binding affinity scoring functions, such as the solvated interaction energy (SIE) function [3]. Prediction of relative antigen-antibody association rates ($k_{on}$) between parent and mutant antibodies was carried out with methods that evaluate long-range electrostatic interactions, such as HyPARE [4]. Candidate single-point mutants were the assembled into multiple-point mutants and re-scored for relative binding affinity.

Multiple-point mutants were generated by combining single-point mutants between light and heavy chains to achieve the targeted change in affinity. A requirement was to use as few single-point mutants as possible and to maximize the number of generated assembled antibodies. Another desirable feature was to generate a pool of mutants with reduced affinities due to either increased dissociation rates ($k_{-off}$) or to decreased association rates ($k_{-on}$). Among suitable candidate single-point mutations, those targeting distinct locations within the antibody-antigen interface, preferably at its periphery, were given higher priority.

Preparation of Plasmids

All the cDNAs encoding the heavy and light chains of the antibodies were ordered from GeneArt (Regensburg Germany). The cDNAs were removed from the plasmid provided by GeneArt by digestion with HindIII and cloned into the HindIII site of plasmid pKCR5 previously dephosphorylated with calf intestinal phosphatase (NEB) to prevent recircularization. In pKCR5, transcription of the cDNA is under the control of the strong CR5 promoter, part of the cumate gene switch. The plasmid pKCR5 is available from the Biotechnology Research Institute, Montreal, Canada and is described by Mullick et al [6]. This 3.9 kb plasmid incorporates a HindIII in proper context with the CR5 promoter and a rabbit b-globin polyA, together with a B-lactamase gene for selection, and colE1 and f1 origins of replication. For transfection of CHO cells, all plasmids were isolated from large culture of *E. coli* using the Plasmid Maxi kit (Qiagen Inc, Mississauga, ON) according to the manufacturer's recommendation. Briefly, 200 ml of LB medium containing 100 µg/ml ampicillin were inoculated with a single fresh colony of *E. coli* and incubated overnight at 37° C. with vigorous shaking (250 rpm). The bacteria were pelleted by centrifugation at 6000×g, for 15 min, at 4° C. and the plasmid was isolated using the protocols, buffers and columns provided by the kit. The pure plasmids was resuspended in sterile 50 mM TRIS, pH 8 and quantified by measuring the optical density at 260 nm.

Cell Line (CHO-cTA; Clone 5F1) and Growth Conditions

The CHO-cTA cell line (Gaillet et al [5]; Mullick et al. [6]) used for transient transfection is a Chinese Hamster Ovary cell line (CHO) adapted to grow in suspension and in protein-free medium. The cell line stably expresses the cumate transactivator (cTA) which activates transcription by binding to the CR5 promoter. The CHO-cTA are maintained in CD-CHO medium (Invitrogen, CDCHO 10743), supplemented with 4 mM glutamine, 50 µg/mL and dextran sulfate (Amersham Pharmacia Biotech) at 37° C. under an atmosphere of 5% $CO_2$. When the cells reach a concentration of $1.0×10^6$ cells/ml (on average three times a week) they are passaged by diluting them to a concentration of $5.0×10^4$ cells/ml using fresh medium.

Transient Transfection of CHO-cTA

Before transfection, the cells were washed with PBS and resuspended at a concentration of $2.5×10^6$ cell/ml in growth medium without dextran sulfate for 3 hrs in suspension culture. 50 ml of cells were transfected by adding slowly 2.5 ml of a CDCHO medium supplemented with 1 µg/ml of plasmid and 5 µg·ml. polyethylenimine (PEI Max; Polysciences). After 2 hrs, the cells were transferred at 30° C. The next days, 50 µg/mL of dextran sulfate was added to the cells and they were incubated at 30° C. for a total of 4 days. The supernatant was clarified by centrifugation and filtered through a 0.22 µM filter and transferred at −80° C. until further analysis.

Polyacrylamide Gel Electrophoresis (SDS-PAGE)

Known amounts of supernatant were resuspended into an equal volume of Laemmli 2× and heated at 95° C. for 5 min and chilled on ice. The samples were then separated on a polyacrylamide Novex 10% Tris-Glycine gel (Invitrogen Canada Inc., Burlington, ON). A standard curve was made by adding known amount of purified human IgG. The gel was then stained using a solution of Coomassie Fluor™-Orange (Molecular Probes, Eugene OR) according to the manufacturer's recommendations. The signal was visualized and quantified using the Typhoon Scanner.

Western Blot Analysis

Known amounts of supernatant were separated on a SDS-PAGE as described above and then transferred onto a Hybond-N nitrocellulose membrane (Amersham Bioscience Corp., Baie d'Urfée, QC) for 1 h at 275 mA. The membrane was blocked for 1 h in 0.15% Tween 20, 5% skimmed milk in PBS and incubated for 1 h with an anti-human IgG conjugated to Cy5 (Jackson, Cat #109-176-099). The signal was revealed by scanning with the Typhoon Trio+ (Amersham Biosciences, GE Healthcare).

ELISA 96 wells/plates were coated with 50 µl of affiniPure Goat Anti-Human IgG, (H+L) (Jackson Immuno Research) and incubated overnight at 4° C. The wells were washed with PBS and incubated for 30 min at 37° C. with 100 µl of 1% BSA in PBS at 37° C. 25 µl of samples diluted with 1% BSA in PBS were added to the wells, which were incubated for 2 hrs at 37° C. The wells were washed with 0.05% Tween 20 in PBS and incubated with an alkaline Phosphatase-conjugated AffiniPure Goat Anti-Human IgG (1-1+L) (Jackson Immuno Research) for 1 hr at 37° C. The wells were washed with 0.05% Tween 20 in PBS, followed by PBS. The signal was revealed by incubation with PNPP for 30 min at 37° C. The signal intensity was measure at 405 nm. A standard curve was made using known amount of purified antibody (IgG1, kappa from myeloma plasma (Athens Research Technology).

Purification of Antibody

The supernatant was concentrated with an Amicon Ultra (Ultracel-50K) at 1500 rpm to a volume of 500 µl. The wild type and mutants, antibodies were purified using the ProPur protein A mini spin columns (Nunc) according to the manufacture's recommendations. The purified antibodies were then desalted and resuspended in PBS using the desalting column PD-10 (GE Healthcare). The antibodies were then concentrated by centrifugation on an Amica Ultra 100,000 MWCO membrane. The purified antibodies were quantified by reading the optical density at 280 nm using the Nanodrop spectrophotometer. The purified antibodies were kept frozen at −20° C. in 50% glycerol.

In Vitro Binding by Surface Plasmon Resonance

Kinetic and affinity analysis was carried out using a BioRad Proteon surface plasmon resonance instrument. The running buffer for all steps was 10 mM HEPES, 150 mM NaCl, 3.5 mM EDTA and 0.05% Tween20 at pH 7.4. An antibody capture sensorchip was prepared by injecting 6.5 µg/mL of anti-human Fc (Jackson Immunochemicals Inc.) in 10 mM sodium acetate pH 4.5 at flow rate 25 µL/min over a GLM sensorchip (BioRad Inc.) that had previously been activated with a 1/10 dilution of sNHS/EDC (BioRad Inc.) until the surface was saturated (approximately 5000 RUs). This procedure was carried out in the analyte direction to ensure all of the interspots for referencing have immobilized anti-mouse Fc. Wild-type cetuximab and variants were captured in the ligand direction by injecting 100 µl, of 4% culture supernatants or purified samples in running buffer at flow rate of 25 µL/min until 400 to 800 resonance units have been captured. This was immediately followed by two pulses of running buffer in the analyte direction, 50 uL each at flow rate 100 µL/min to stabilize the baseline. Next, the simultaneous injection of 100 tit of five EGFR ectodomain (EGFRed) concentrations (3-fold dilutions of 20 nM to 1000 nM EGFR depending on the affinity of the cetuximab variant) and buffer blank at a flow rate of 50 µL/min with a 600 s dissociation was carried out to analyse the EGFRed-antibody interaction. Kinetic rate constants (on- and off-rates) and affinity constants were generated from the aligned and double referenced sensorgrams with the Langmuir binding model using BioRad Proteon Manager software v3.1. Mutants with fast on- and off-rates had their affinity constants determined using the equilibrium fit model which uses plateau values from the sensorgrams to generate a binding isotherms for KD constant determination.

Cell Culture

The U87MG glioblastoma cell line was obtained from ATCC (HTB-14). A stably transfected full length wt EGFR or a deleted version of EGFR (variant 3 overexpressing cell line variants were gifts from W. Cavanee, Ludwig Institute for Cancer Research, University of California at San Diego). The human epidermoid A431 cell line was obtained from ATCC (CRL-1555). Cell lines were maintained in DMEM (Gibco) containing 10% fetal bovine serum (Gibco). Primary adult human epithelial keratinocytes were obtained from ScienCell (Catalog #2110) and cultured using manufacturer's recommended Keratinocyte Medium (KM, Cat. No. 2101). Generally cells were passaged once or twice a week and used within 4-6 weeks for all experiments.

Detection of Antibody Binding to Surface EGFR Level by Flow Cytometry

Prior to analysis, cells were plated such that they were not more than 80% confluent on the day of analysis. Tumor (U87 MG derivatives, A431) or normal (human epidermal keratinocytes) cell were washed in PBS and harvested by the addition of cell dissociation buffer (Sigma.). A cell suspension containing $2.5 \times 10^5$ cells (in 500 µl corresponding cell culture media) was incubated with various concentrations (0.01-100 ug/ml) of anti-EGFR antibodies for 2 h at 4° C. (to prevent internalization). Following 1 wash with cell culture media, primary antibody was incubated with 2 ug Dylight 488 conjugated AffiniPure goat anti-human IgG Alexa 488 secondary antibody (Jackson Immuno Research 109-487-003) in 100 ul of media for 1 h at 4° C. Cells were then pelleted and stored on ice until ready to be analyzed by flow cytometry. Prior to analysis, cell pellets were resuspended in 300-500 ul media and filtered through a 50 um nylon mesh filter to remove cell aggregates. Flow cytometry analyses were performed on 10,000 viable cells gated on forward scattering, side scattering parameters and propidium iodide dye exclusion using a BD LSRII flow Cytometer (Becton-Dickinson Biosciences, CA, USA) and a standard filter set using BD FACSDiva™ acquisition software, according to manufacturer's instructions.

Specific antibody binding was calculated as the mean fluorescent intensity of binding to each antibody after background level subtraction of the mean fluorescent intensity of binding in the absence of primary antibody (but containing secondary detection antibody). An alternative approach was used to calculate specific antibody binding on cells, i.e. it was calculated as fold-binding over background by dividing the mean fluorescent intensity in the presence of primary antibody by the mean fluorescent intensity obtained in the absence of primary antibody (but containing secondary antibody). To examine the binding selectivity of the antibodies, the value of antibody binding to tumor (overexpressing EGFR) was divided by the binding observed with cells not overexpressing EGFR. This parameter, named the ratio of binding, was calculated and compared to that seen with wild type antibody. A commercial source of Cetuximab (Merck kGA) was used as a benchmark for comparison purposes.

Evaluation of Antibody-Mediated Cytotoxicity as Antibody-Drug Conjugates

In this set of experiments, primary antibodies (typically 1 nM in concentration) were incubated with 2 nM anti-human secondary antibody that was chemically conjugated with saporin toxin (from Advanced Targeting Systems, San Diego, CA), a ribosome inactivating enzyme that needs to be internalized to cause cell death. The antibody complex was then added to the cell types indicated (plated in triplicate) and their effects on cell viability measured after 72 hr incubation at 37° C. EGFR directed cytotoxicity can be quantitated following evaluation with controls for non-specific cytotoxicity (no primary antibody or an irrelevant primary antibody (control human IgG) were used to assess non-specific cytotoxicity). Cell viability can be measured using standard techniques, including the use of sulforhodamine B.

Results:

1. Production and Purification of EGFR Antibodies

Nine cDNAs corresponding to the coding sequence of the EGFR antibodies were synthesized (GeneArt). All the cDNAs were cloned into the HindIII site of pKCR5, an expression vector regulated by the cumate-switch (pKCR5 vector (see map). For each antibody, 50 ml of CHOcTA (expressing the cumate transactivator, cTA) were transfected with various combinations of heavy and light chain Four days after transfection the supernatant was analyzed by SDS-PAGE, Western Blot and ELISA.

Table 3 below summarizes quantification of the antibodies produced by transient transfection in CHOcTA cells, done by ELISA and by western blot using a purified human IgG1 as standard.

TABLE 3

| Mutants | | Quantification by Western blot (mg/L) | Quantification by E.L.I.S.A (mg/L) |
| --- | --- | --- | --- |
| HC_LC | wt_HC + wt_LC | 13.72 | 10.09 |
| HC_1 | wt_HC + LC_E53K | 6.02 | 3.44 |
| HC_2 | wt_HC + LC_W94A | 5.34 | 5.97 |
| 3_LC | HC_Y101A + wt_LC | 10.73 | 6.57 |
| 3_1 | HC_Y101A + LC_E53K | 1.72 | 3.62 |
| 3_2 | HC_Y101A + LC_W94A | 6.24 | 5.13 |
| 4_LC | HC_Y102A + wt_LC | 6.77 | 6.64 |
| 4_1 | HC_Y102A + LC_E53K | 6.59 | 6.19 |
| 4_2 | HC_Y102A + LC_W94A | 9.17 | 7.16 |
| 5L_C | HC_D103N + wt_LC | 18.46 | 9.58 |
| 5_1 | HC_D103N + LC_E53K | 2.52 | 6.59 |
| 5_2 | HC_D103N + LC_W94A | 21.05 | 13.59 |
| 6_LC | HC_D58N_D103N + wt_LC | 18.55 | 15.71 |
| 6_1 | HC_D58N_D103N + LC_E53K | 6.47 | 7.03 |
| 6_2 | HC_D58N_D103N + LC_W94A | 29.13 | 20.03 |
| 7_LC | HC_D58N_D103N_E105Q + wt_LC | 16.36 | 11.04 |
| 7_1 | HC_D58N_D103N_E1 05Q + EC_E53K | 9.86 | 5.82 |
| 7_2 | HC_D58N_D103N_E105Q + LC_W94A | 17.38 | 12.41 |

The 2 wild type chains and 7 mutant chains were purified by chromatography using protein A. The purified proteins were quantified by $OD_{280}$ (NanoDrop). The purified antibodies were analyzed by non-denaturing and denaturing SDS-PAGE.

2. Binding Affinity Determination of EGFR Antibodies by SPR

The SPR results are provided in Table 4 and Table 4-1 below:

TABLE 4

| Antibody | $k_a$ (1/Ms) | $k_d$ (1/S) | $K_D$ (nM) $k_d/k_a$ | $K_D$ (nM) steady state |
|---|---|---|---|---|
| Cetuximab (purchased) | 4.09E+6 | 1.15E−3 | 0.28 | nd |
|  | 4.82E+6 | 1.42E−3 | 0.30 | nd |
| HC/LC = wt_HC + wt_LC | 4.47E+6 | 1.55E−3 | 0.35 | nd |
| HC/1 = wt_HC + LC_E53K | 2.48E+6 | 3.29E−3 | 1.33 | nd |
|  | 2.31E+6 | 3.71E−3 | 1.61 | nd |
|  | 2.36E+6 | 2.86E−3 | 1.21 | nd |
| 3/LC = HC_Y101A + wt_LC | 2.32E+6 | 0.06 | 27.3 | 15.4 |
| 4/LC = HC_Y102A + wt_LC | 1.36E+6 | 0.13 | 98.9 | 50.3 |
|  | 2.17E+6 | 0.09 | 43.3 | 44.5 |
| 5/LC = HC_D103N + wt_LC | 1.29E+6 | 0.1 | 80.3 | 44.8 |
| 3/1 = HC_Y101A + LC_E53K | 1.8E+6 | 0.1 | 57.3 | 62.9 |
| HC/2 = wt_HC + LC_W94A | 2.36E+6 | 0.18 | 75.1 | 72.3 |
| 7/LC = HC_D58N/D103N/E105Q + wt_LC | 1.08E+6 | 0.07 | 67.3 | 67.0 |
|  | 1.27E+6 | 0.08 | 61.9 | 89.0 |
| 6/LC = HC_D58N/D103N + wt_LC | nd | nd |  | 74.4 |

TABLE 4-1

| Antibody name | Description | N | KD ± SD (nM) |
|---|---|---|---|
| Cetuximab | commercial mAb | 4 | 0.3 ± 0.2 |
| HC_LC | wt_HC + wt_LC | 3 | 0.3 ± 0.2 |
| HC_1 | wt_HC + LC_E53K | 4 | 1.2 ± 0.5 |
| HC_2 | wt_HC + LC W94A | 2 | 71 ± 3 |
| 3_LC | HC_Y101A + wt_LC | 2 | 1.2 ± 0.5 |
| 4_LC | HC_Y102A + wt_LC | 3 | 46 ± 4 |
| 5_LC | HC_D103N + wt_LC | 2 | 41 ± 5 |
| 6_LC | HC_D58ND103N + wt_LC | 1 | 250 |
| 7_LC | HC_ D58N D103N E105Q + wt_LC | 3 | 60 ± 8 |
| 3_1 | HC_Y101A ± LC_E53K | 2 | 66 ± 4 |
| 4_1 | HC_Y102A + LCE53K | 2 | 200 ± 100 |
| 5_1 | HC_D103N + LC_E53K | 1 | 840 |
| 6_1 | HC_D58N D103N + LC E53K | 1 | >>100 |
| 7_1 | HC_D58N_D103N E105Q + LC E53K | 1 | 1400 |
| 3_2 | HC_Y101A + LC W94A | 1 | Too weak to be detected |
| 4_2 | HC_Y102A + LC_W94A | 1 | Too weak to be detected |
| 5_2 | HC_D103N + LC W94A | 1 | Too weak to be detected |
| 6_2 | HC_D58N D103N + LC W94A | 1 | >>1000 |
| 7_2 | HC_D58N D103N E105Q + LC_W94A | 1 | >>1000 |

Table 4-1 provides SPR-based affinity determinations that have either been refined or are additional to those provided in Table 4.

The results indicated that approximately 5000 of the cetuximab variants did not have any detectable activity at the 100 nM EGFR tested (data not shown). Of those that showed binding activity (Table 4), only the wild-type (HC/LC) and mutant HC/1 had a moderately-slow off rate. All of the other variants with activity (3/LC, 4/LC, 4/1, 5/LC, 6/LC, 7/LC, 3/1 and HC/2) had both a fast association and dissociation from the flowing EGFRed. Affinity constants (KDs) were determined from the ratio of the kinetic rates (kd s-1/ka s-1M-1) using a 1:1 langmuir binding model where amenable, otherwise affinity constants were determined from an equilibrium fit using plateau binding values only. Mutants 6_2 and 7_2 showed very weak binding at 1000 nM EGFR but were not quantifiable.

3. Binding of EGFR Antibodies to Various Cell Lines as Determined by Indirect Flow Cytometry FIG. 1 depicts graphs showing binding of antibodies to cell surface EGFR present on the surface of (A) parental U87MG cells, (B) U87 cells overexpressing wt EGFR, (C) U87 cells overexpressing EGFR vIII and (D) primary human epidermal keratinocytes (HEK), at 1 and 10 μg/mlmAb (A-C) or 0.1 and 1 μg/ml mAb (D). These were compared to wt mAb (HC/LC, set arbitrarily to 100%). In FIG. 1-1 (A and B), the same plus additional results are presented differently, i.e. all binding is divided by background binding (that is, is expressed is as a fold change over background binding) rather than background binding being subtracted from all binding values (as in FIG. 1). This data analysis approach de-emphasizes variations caused by small changes in background binding. As expected, these results demonstrate less binding of anti-EGFR mAbs to parental U87 cells or HEK cells compared to tumor cells which overexpress EGFR. Importantly, these results demonstrate a greater reduction in binding of some anti-EGFR mAb variants to cells expressing lower EGFR levels (parental U87 or HEK cells) as compared to U87 cells overexpressing EGFR.

4. Evaluation of Antibody Binding to Tumor and Normal Cell Lines

FIG. 2 is a graph representing binding selectivity of antibodies. The ratio of antibody binding (with background subtracted) to EGFR overexpressing cells [U87MGwtEGFR or A431 cells (which naturally overexpress wt EGFR)] relative to antibody binding to normal HEK cells was calculated and compared to that seen with wild type antibody (ratio set arbitrarily to 1 for wt antibody). This result clearly shows that some of the EGFR mAbs exhibit a better ratio of binding to tumor relative to normal HEK cells (e.g. mutant HC-2 exhibits a 20-fold better ratio, and mutant 3-1 exhibits a 40-50-fold better ratio of binding to tumor versus normal cells). In FIG. 2-1, the same results as in FIG. 2 are shown using a different data presentation approach, i.e. all binding is divided by background. These results also clearly show that some of the EGFR mAbs exhibit a better ratio of binding to tumor cells that overexpress EGFR relative to normal HEK cells (e.g. mutant HC-2 exhibits 80-100 fold differential binding, and mutant 3-1 exhibits 120-140 fold differential binding to tumour cells versus normal cells, whereas wt antibody (HC-LC) exhibits 12-15 fold differential binding to tumour cells versus normal cells. In other words, HC-2 exhibits an 46-fold better ratio of binding, and mutant 3-1 exhibits an ~9-fold better ratio of binding to tumor than normal cells. The pattern of binding specificity was similar amongst the tumor cell lines analyzed (U87MGwt EGFR and A431) suggesting that the selectivity of binding is universally high for tumor cells overexpressing EGFR (~2 million receptors per cell or more).

It will further be appreciated from the results shown in FIG. 3 that there is a greater reduction in binding of some anti-EGFR mAb variants to cells expressing (A) lower EGFR levels (parental U87) as compared to (B) U87 cells overexpressing EGFR.

Also, as shown in FIG. 4, it is clear that the ratio of antibody binding to EGFR overexpressing cells (U87MGwtEGFR) relative to antibody binding to parental U87MG cells was improved in most cases by 2-4 fold. That is, a ratio of 11 for wild type antibody binding to U87MGwtEGFR cells versus parental cells, and ratios up to 35 for certain mutated antibodies, e.g. mutant 7-LC and 4-LC, were observed. Antibody 6-2 and 7-2 exhibited no detectable binding to EGFR on either cell type at the concentrations used (1 ug/ml).

Finally, in FIGS. 5A and 5B it is shown and confirmed that some mutant antibodies can bind to EGFR and deliver a protein toxin, in this case saporin. Mutant antibodies 6-2 and 7-2 exhibited cytotoxicity similar to that seen with the non-specific controls, which is not unexpected since they do not detectably bind EGFR on the surface of these cells (FIG. 3). Notably, in comparison to the cytotoxicity profile seen for the wt EGFR MAb (HC/LC), antibodies 6-LC, 7-LC and 4-1 exhibited decreased cytotoxicity on cells with low levels of EGFR (human epidermal keratinocytes (HEK) and parental U87 cells) with little decrease in cytotoxicity on U87 cells overexpressing wild type EGFR.

In summary, this data indicates that mutant antibodies can be generated that bind highly selectively to cells that present EGFR at abnormally high density, and that these antibodies may be useful in oncology and other diseases as antibody-drug conjugates with broad therapeutic windows, and/or as diagnostic agents for the detection of EGFR overexpressing cells.

All references cited herein, including all database references and the sequence information referenced therein, are hereby incorporated herein in their entirety.

REFERENCES

1. Li S, Schmitz K R, Jeffrey P D, Wiltzius J J, Kussie P, Ferguson K M (2005) *Cancer Cell* 7:301-311.
2. Li Z, Scheraga H A (1987) *Proc. Natl. Acad. Sci. U.S.A.* 84:6611-6615.
3. Naim M, Bhat S, Rankin K N, Dennis S, Chowdhury S F, Siddiqi I, Drabik P, Sulea T, Bayly C I, Jakalian A, Purisima E O (2007) *J Chem. Inf. Model.* 47:122-133.
4. Selzer T, Albeck S, Schreiber G (2000) *Nat. Struct. Biol.* 7:537-541.
5. Gaillet, B., R. Gilbert, R. Amziani, C. Guilbault, C. Gadoury, A. W. Caron, A. Mullick, A. Garnier, and B. Massie. 2007. High-Level Recombinant Protein Production in CHO Cells Using an Adenoviral Vector and the Cumate Gene-Switch. *Biotechnol. Prog.* 23:200-209.
6. Mullick, A., Y. Xu, R. Warren, M. Koutroumanis, C. Guilbault, S. Broussau, F. Malenfant, L. Bourget, L. Lamoureux, R. Lo, A. W. Caron, A. Pilotte, and B. Massie. 2006. The cumate gene-switch: a system for regulated expression in mammalian cells. *BMC Biotechnol.*

Polynucleotides encoding the various mutant antibody chains are provided below. Substituted codons are shaded, and HindIII sites are highlighted:

```
Light chain wild-type (shown here with the signal peptide) [SEQ ID No. 11]:
GTTTAAACGAATTCGCCCTTGAGGTACCAAGCTTGCCACCATGGTGCTGCAGACCCAGGT

GTTCATCTCCCTGCTGCTGTGGATCTCTGGCGCCTACGGCGACATCCTGCTGACCCAGTC

CCCCGTGATCCTGTCCGTGTCCCTGGCGAGCGGGTGTCCTTCTCTTGCCGGGCCTCCCA

GTCCATCGGCACCAACATCCACTGGTATCAGCAGCGGACCAACGGCTCCCCTCGGCTGCT

GATCAAGTACGCCTCCGAGTCTATCTCCGGCATCCCTTCCCGGTTCTCCGGCTCTGGCTC

CGGCACCGACTTCACCCTGTCCATCAACTCCGTGGAGTCCGAGGATATCGCCGACTACTA

CTGCCAGCAGAACAACAACTGGCCTACCACCTTCGGCGCTGGCACCAAGCTGGAACTGAA

GCGACCGTGGCCGCTCCTTCCGTGTTCATCTTCCCACCTTCCGACGAGCAGCTGAAGTC

CGGCACCGCCTCTGTGGTGTGCCTGCTGAACAACTTCTACCCTCGGGAGGCCAAGGTGCA
```

-continued
GTGGAAGGTGGACAACGCCCTGCAGTCCGGCAACTCCCAGGAATCCGTCACCGAGCAGGA

CTCCAAGGACTCTACCTACTCCCTGTCCTCCACCCTGACCCTGTCCAAGGCCGACTACGA

GAAGCACAAGGTGTACGCCTGCGAAGTGACCCACCAGGGCCTGTCCAGCCCTGTGACCAA

GTCCTTCAACCGGGGCGAGTGCTGAAAGCTTGAGCTCAGTAAGGGCGAATTCGCGGCCGC

Light chain E58K mutant (shown here with the signal peptide) [SEQ ID No. 12]:
CGGAAGGCCCATGAGGCCAGTTAATTAAGAGGTACCAAGCTTGCCACCATGGTGCTGCAG

ACCCAGGTGTTCATCTCCCTGCTGCTGTGGATCTCTGGCGCCTACGGCGACATCCTGCTG

ACCCAGTCCCCCGTGATCCTGTCCGTGTCCCCTGGCGAGCGGGTGTCCTTCTCTTGCCGG

GCCTCCCAGTCCATCGGCACCAACATCCACTGGTATCAGCAGCGGACCAACGGCTCCCCT

CGGCTGCTGATCAAGTACGCCTCC███TCTATCTCCGGCATCCCTTCCCGGTTCTCCGGC

TCTGGCTCCGGCACCGACTTCACCCTGTCCATCAACTCCGTGGAGTCCGAGGATATCGCC

GACTACTACTGCCAGCAGAACAACAACTGGCCTACCACCTTCGGCGCTGGCACCAAGCTG

GAACTGAAGCGGACCGTGGCCGCTCCTTCCGTGTTCATCTTCCCACCTTCCGACGAGCAG

CTGAAGTCCGGCACCGCCTCTGTGGTGTGCCTGCTGAACAACTTCTACCCTCGGGAGGCC

AAGGTGCAGTGGAAGGTGGACAACGCCCTGCAGTCCGGCAACTCCCAGGAATCCGTCACC

GAGCAGGACTCCAAGGACTCTACCTACTCCCTGTCCTCCACCCTGACCCTGTCCAAGGCC

GACTACGAGAAGCACAAGGTGTACGCCTGCGAAGTGACCCACCAGGGCCTGTCCAGCCCT

GTGACCAAGTCCTTCAACCGGGGCGAGTGCTGAAAGCTTGAGCTCATGGCGCGCCTAGGC

CTTGACGGCCTTCCG

Light chain W94K mutant (shown here with the signal peptide):[SEQ ID No.13]:
CGGAAGGCCCATGAGGCCAGTTAATTAAGAGGTACCAAGCTTGCCACCATGGTGCTGCAG

ACCCAGGTGTTCATCTCCCTGCTGCTGTGGATCTCTGGCGCCTACGGCGACATCCTGCTG

ACCCAGTCCCCCGTGATCCTGTCCGTGTCCCCTGGCGAGCGGGTGTCCTTCTCTTGCCGG

GCCTCCCAGTCCATCGGCACCAACATCCACTGGTATCAGCAGCGGACCAACGGCTCCCCT

CGGCTGCTGATCAAGTACGCCTCCGAGTCTATCTCCGGCATCCCTTCCCGGTTCTCCGGC

TCTGGCTCCGGCACCGACTTCACCCTGTCCATCAACTCCGTGGAGTCCGAGGATATCGCC

GACTACTACTGCCAGCAGAACAACAAC███CCTACCACCTTCGGCGCTGGCACCAAGCTG

GAACTGAAGCGGACCGTGGCCGCTCCTTCCGTGTTCATCTTCCCACCTTCCGACGAGCAG

CTGAAGTCCGGCACCGCCTCTGTGGTGTGCCTGCTGAACAACTTCTACCCTCGGGAGGCC

AAGGTGCAGTGGAAGGTGGACAACGCCCTGCAGTCCGGCAACTCCCAGGAATCCGTCACC

GAGCAGGACTCCAAGGACTCTACCTACTCCCTGTCCTCCACCCTGACCCTGTCCAAGGCC

GACTACGAGAAGCACAAGGTGTACGCCTGCGAAGTGACCCACCAGGGCCTGTCCAGCCCT

GTGACCAAGTCCTTCAACCGGGGCGAGTGCTGAAAGCTTGAGCTCATGGCGCGCCTAGGC

CTTGACGGCCTTCCG

Heavy chain wild-type (shown here with the signal peptide) [SEQ ID No. 14]:
CGAATTGAAGGAAGGCCGTCAAGGCCGCATGGTACCAAGCTTGCCACCATGGACTGGACC

TGGCGGATCCTGTTTCTGGTGGCCGCTGCTACCGGCACACACGCCCAGGTGCAGCTGAAG

CAGTCTGGCCCTGGCCTGGTGCAGCCTTCCCAGTCCCTGTCCATCACCTGTACCGTGTCC

GGCTTCTCCCTGACCAACTACGGCGTGCACTGGGTGCGCCAGTCTCCAGGCAAGGGCCTG

GAATGGCTGGGAGTGATTTGGTCCGGCGGCAACACCGACTACAACACCCCTTTCACCTCC

CGGCTGTCCATCAACAAGGACAACTCCAAGTCCCAGGTGTTCTTCAAGATGAACTCCCTG

CAGTCCAACGACACCGCCATCTACTACTGCGCCAGGGCTCTGACCTACTACGACTACGAG

```
TTCGCCTACTGGGGCCAGGGCACCCTGGTGACCGTGTCCGCCGCTTCCACCAAGGGCCCT

AGCGTGTTCCCTCTGGCCCCTTCCAGCAAGTCTACCTCTGGCGGCACCGCTGCTCTGGGC

TGCCTGGTGAAGGACTACTTCCCTGAGCCTGTGACAGTGTCCTGGAACTCTGGCGCCCTG

ACCTCCGGAGTGCACACCTTCCCTGCTGTGCTGCAGTCCTCCGGCCTGTACTCCCTGTCC

TCCGTGGTGACAGTGCCTTCCTCCAGCCTGGGCACACAGACCTACATCTGCAACGTGAAC

CACAAGCCTTCCAACACCAAGGTGGACAAGCGGGTGGAGCCTAAGTCCTGCGACAAGACC

CACACCTGTCCTCCATGCCCTGCCCCTGAGCTGCTGGGCGGACCCTCCGTGTTCCTGTTC

CCTCCAAAGCCTAAGGACACCCTGATGATCTCCCGGACCCCTGAAGTGACCTGCGTGGTG

GTGGACGTGTCCCACGAGGATCCTGAAGTGAAGTTCAATTGGTACGTGGACGGCGTGGAG

GTGCACAACGCCAAGACCAAGCCTCGGGAGGAACAGTACAACTCCACCTACCGGGTGGTG

TCCGTGCTGACCGTGCTGCACCAGGACTGGCTGAACGGCAAAGAGTACAAGTGCAAGGTC

TCCAACAAGGCCCTGCCTGCCCCTATCGAAAAGACCATCTCCAAGGCCAAGGGCCAGCCT

CGGGAACCTCAGGTGTACACACTGCCTCCCAGCAGGGACGAGCTGACCAAGAACCAGGTG

TCCCTGACCTGTCTGGTGAAGGGCTTCTACCCTTCCGATATCGCCGTGGAGTGGGAGTCT

AACGGCCAGCCTGAGAACAACTACAAGACCACCCCTCCTGTGCTGGACTCCGACGGCTCC

TTCTTCCTGTACTCCAAACTGACCGTGGACAAGTCCCGGTGGCAGCAGGGCAACGTGTTC

TCCTGCTCCGTGATGCACGAGGCCCTGCACAACCACTACACCCAGAAGTCCCTGTCTCTG

TCCCCTGGCAAGTGAAAGCTTGAGCTCCTGGGCCTCATGGGCCTTCCTTTCACTGCC

Heavy chain Y101A mutant(shown here with the signal peptide) [SEQ ID No.15]:
CGGAAGGCCCATGAGGCCAGTTAATTAAGAGGTACCAAGCTTGCCACCATGGACTGGACC

TGGCGGATCCTGTTTCTGGTGGCCGCTGCTACCGGCACACACGCCCAGGTGCAGCTGAAG

CAGTCTGGCCCTGGCCTGGTGCAGCCTTCCCAGTCCCTGTCCATCACCTGTACCGTGTCC

GGCTTCTCCCTGACCAACTACGGCGTGCACTGGGTGCGCCAGTCTCCAGGCAAGGGCCTG

GAATGGCTGGGAGTGATTTGGTCCGGCGGCAACACCGACTACAACACCCCTTTCACCTCC

CGGCTGTCCATCAACAAGGACAACTCCAAGTCCCAGGTGTTCTTCAAGATGAACTCCCTG

CAGTCCAACGACACCGCCATCTACTACTGCGCCAGGGCTCTGACC███TACGACTACGAG

TTCGCCTACTGGGGCCAGGGCACCCTGGTGACCGTGTCCGCCGCTTCCACCAAGGGCCCT

AGCGTGTTCCCTCTGGCCCCTTCCAGCAAGTCTACCTCTGGCGGCACCGCTGCTCTGGGC

TGCCTGGTGAAGGACTACTTCCCTGAGCCTGTGACAGTGTCCTGGAACTCTGGCGCCCTG

ACCTCCGGAGTGCACACCTTCCCTGCTGTGCTGCAGTCCTCCGGCCTGTACTCCCTGTCC

TCCGTGGTGACAGTGCCTTCCTCCAGCCTGGGCACACAGACCTACATCTGCAACGTGAAC

CACAAGCCTTCCAACACCAAGGTGGACAAGCGGGTGGAGCCTAAGTCCTGCGACAAGACC

CACACCTGTCCTCCATGCCCTGCCCCTGAGCTGCTGGGCGGACCCTCCGTGTTCCTGTTC

CCTCCAAAGCCTAAGGACACCCTGATGATCTCCCGGACCCCTGAAGTGACCTGCGTGGTG

GTGGACGTGTCCCACGAGGATCCTGAAGTGAAGTTCAATTGGTACGTGGACGGCGTGGAG

GTGCACAACGCCAAGACCAAGCCTCGGGAGGAACAGTACAACTCCACCTACCGGGTGGTG

TCCGTGCTGACCGTGCTGCACCAGGACTGGCTGAACGGCAAAGAGTACAAGTGCAAGGTC

TCCAACAAGGCCCTGCCTGCCCCTATCGAAAAGACCATCTCCAAGGCCAAGGGCCAGCCT

CGGGAACCTCAGGTGTACACACTGCCTCCCAGCAGGGACGAGCTGACCAAGAACCAGGTG

TCCCTGACCTGTCTGGTGAAGGGCTTCTACCCTTCCGATATCGCCGTGGAGTGGGAGTCT
```

-continued
AACGGCCAGCCTGAGAACAACTACAAGACCACCCCTCCTGTGCTGGACTCCGACGGCTCC

TTCTTCCTGTACTCCAAACTGACCGTGGACAAGTCCCGGTGGCAGCAGGGCAACGTGTTC

TCCTGCTCCGTGATGCACGAGGCCCTGCACAACCACTACACCCAGAAGTCCCTGTCTCTG

TCCCCTGGCAAGTGAAAGCTTGAGCTCATGGCGCGCCTAGGCCTTGACGGCCTTCCG

Heavy chain Y102A mutant (shown here with the signal peptide) [SEQ ID No.16]:
CGGAAGGCCCATGAGGCCAGTTAATTAAGAGGTACCAAGCTTGCCACCATGGACTGGACC

TGGCGGATCCTGTTTCTGGTGGCCGCTGCTACCGGCACACACGCCCAGGTGCAGCTGAAG

CAGTCTGGCCCTGGCCTGGTGCAGCCTTCCCAGTCCCTGTCCATCACCTGTACCGTGTCC

GGCTTCTCCCTGACCAACTACGGCGTGCACTGGGTGCGCCAGTCTCCAGGCAAGGGCCTG

GAATGGCTGGGAGTGATTTGGTCCGGCGGCAACACCGACTACAACACCCCTTTCACCTCC

CGGCTGTCCATCAACAAGGACAACTCCAAGTCCCAGGTGTTCTTCAAGATGAACTCCCTG

CAGTCCAACGACACCGCCATCTACTACTGCGCCAGGGCTCTGACCTAC███GACTACGAG

TTCGCCTACTGGGGCCAGGGCACCCTGGTGACCGTGTCCGCCGCTTCCACCAAGGGCCCT

AGCGTGTTCCCTCTGGCCCCTTCCAGCAAGTCTACCTCTGGCGGCACCGCTGCTCTGGGC

TGCCTGGTGAAGGACTACTTCCCTGAGCCTGTGACAGTGTCCTGGAACTCTGGCGCCCTG

ACCTCCGGAGTGCACACCTTCCCTGCTGTGCTGCAGTCCTCCGGCCTGTACTCCCTGTCC

TCCGTGGTGACAGTGCCTTCCTCCAGCCTGGGCACACAGACCTACATCTGCAACGTGAAC

CACAAGCCTTCCAACACCAAGGTGGACAAGCGGGTGGAGCCTAAGTCCTGCGACAAGACC

CACACCTGTCCTCCATGCCCTGCCCCTGAGCTGCTGGGCGGACCCTCCGTGTTCCTGTTC

CCTCCAAAGCCTAAGGACACCCTGATGATCTCCCGGACCCCTGAAGTGACCTGCGTGGTG

GTGGACGTGTCCCACGAGGATCCTGAAGTGAAGTTCAATTGGTACGTGGACGGCGTGGAG

GTGCACAACGCCAAGACCAAGCCTCGGGAGGAACAGTACAACTCCACCTACCGGGTGGTG

TCCGTGCTGACCGTGCTGCACCAGGACTGGCTGAACGGCAAAGAGTACAAGTGCAAGGTC

TCCAACAAGGCCCTGCCTGCCCCTATCGAAAAGACCATCTCCAAGGCCAAGGGCCAGCCT

CGGGAACCTCAGGTGTACACACTGCCTCCCAGCAGGGACGAGCTGACCAAGAACCAGGTG

TCCCTGACCTGTCTGGTGAAGGGCTTCTACCCTTCCGATATCGCCGTGGAGTGGGAGTCT

AACGGCCAGCCTGAGAACAACTACAAGACCACCCCTCCTGTGCTGGACTCCGACGGCTCC

TTCTTCCTGTACTCCAAACTGACCGTGGACAAGTCCCGGTGGCAGCAGGGCAACGTGTTC

TCCTGCTCCGTGATGCACGAGGCCCTGCACAACCACTACACCCAGAAGTCCCTGTCTCTG

TCCCCTGGCAAGTGAAAGCTTGAGCTCATGGCGCGCCTAGGCCTTGACGGCCTTCCG

Heavy chain D103N mutant (shown here with the signal peptide) [SEQ ID No.17]:
CGGAAGGCCCATGAGGCCAGTTAATTAAGAGGTACCAAGCTTGCCACCATGGACTGGACC

TGGCGGATCCTGTTTCTGGTGGCCGCTGCTACCGGCACACACGCCCAGGTGCAGCTGAAG

CAGTCTGGCCCTGGCCTGGTGCAGCCTTCCCAGTCCCTGTCCATCACCTGTACCGTGTCC

GGCTTCTCCCTGACCAACTACGGCGTGCACTGGGTGCGCCAGTCTCCAGGCAAGGGCCTG

GAATGGCTGGGAGTGATTTGGTCCGGCGGCAACACCGACTACAACACCCCTTTCACCTCC

CGGCTGTCCATCAACAAGGACAACTCCAAGTCCCAGGTGTTCTTCAAGATGAACTCCCTG

CAGTCCAACGACACCGCCATCTACTACTGCGCCAGGGCTCTGACCTACTAC███TACGAG

TTCGCCTACTGGGGCCAGGGCACCCTGGTGACCGTGTCCGCCGCTTCCACCAAGGGCCCT

AGCGTGTTCCCTCTGGCCCCTTCCAGCAAGTCTACCTCTGGCGGCACCGCTGCTCTGGGC

TGCCTGGTGAAGGACTACTTCCCTGAGCCTGTGACAGTGTCCTGGAACTCTGGCGCCCTG

-continued
ACCTCCGGAGTGCACACCTTCCCTGCTGTGCTGCAGTCCTCCGGCCTGTACTCCCTGTCC

TCCGTGGTGACAGTGCCTTCCTCCAGCCTGGGCACACAGACCTACATCTGCAACGTGAAC

CACAAGCCTTCCAACACCAAGGTGGACAAGCGGGTGGAGCCTAAGTCCTGCGACAAGACC

CACACCTGTCCTCCATGCCCTGCCCCTGAGCTGCTGGGCGGACCCTCCGTGTTCCTGTTC

CCTCCAAAGCCTAAGGACACCCTGATGATCTCCCGGACCCCTGAAGTGACCTGCGTGGTG

GTGGACGTGTCCCACGAGGATCCTGAAGTGAAGTTCAATTGGTACGTGGACGGCGTGGAG

GTGCACAACGCCAAGACCAAGCCTCGGGAGGAACAGTACAACTCCACCTACCGGGTGGTG

TCCGTGCTGACCGTGCTGCACCAGGACTGGCTGAACGGCAAAGAGTACAAGTGCAAGGTC

TCCAACAAGGCCCTGCCTGCCCCTATCGAAAAGACCATCTCCAAGGCCAAGGGCCAGCCT

CGGGAACCTCAGGTGTACACACTGCCTCCCAGCAGGGACGAGCTGACCAAGAACCAGGTG

TCCCTGACCTGTCTGGTGAAGGGCTTCTACCCTTCCGATATCGCCGTGGAGTGGGAGTCT

AACGGCCAGCCTGAGAACAACTACAAGACCACCCCTCCTGTGCTGGACTCCGACGGCTCC

TTCTTCCTGTACTCCAAACTGACCGTGGACAAGTCCCGGTGGCAGCAGGGCAACGTGTTC

TCCTGCTCCGTGATGCACGAGGCCCTGCACAACCACTACACCCAGAAGTCCCTGTCTCTG

TCCCCTGGCAAGTGAAAGCTTGAGCTCATGGCGCGCCTAGGCCTTGACGGCCTTCCG

Heavy chain D58N/D103N mutant (shown here with the signal peptide) [SEQ ID No.18]:
CGGAAGGCCCATGAGGCCAGTTAATTAAGAGGTACCAAGCTTGCCACCATGGACTGGACC

TGGCGGATCCTGTTTCTGGTGGCCGCTGCTACCGGCACACACGCCCAGGTGCAGCTGAAG

CAGTCTGGCCCTGGCCTGGTGCAGCCTTCCCAGTCCCTGTCCATCACCTGTACCGTGTCC

GGCTTCTCCCTGACCAACTACGGCGTGCACTGGGTGCGCCAGTCTCCAGGCAAGGGCCTG

GAATGGCTGGGAGTGATTTGGTCCGGCGGCAACACC■TACAACACCCCTTTCACCTCC

CGGCTGTCCATCAACAAGGACAACTCCAAGTCCCAGGTGTTCTTCAAGATGAACTCCCTG

CAGTCCAACGACACCGCCATCTACTACTGCGCCAGGGCTCTGACCTACTAC■TACGAG

TTCGCCTACTGGGGCCAGGGCACCCTGGTGACCGTGTCCGCCGCTTCCACCAAGGGCCCT

AGCGTGTTCCCTCTGGCCCCTTCCAGCAAGTCTACCTCTGGCGGCACCGCTGCTCTGGGC

TGCCTGGTGAAGGACTACTTCCCTGAGCCTGTGACAGTGTCCTGGAACTCTGGCGCCCTG

ACCTCCGGAGTGCACACCTTCCCTGCTGTGCTGCAGTCCTCCGGCCTGTACTCCCTGTCC

TCCGTGGTGACAGTGCCTTCCTCCAGCCTGGGCACACAGACCTACATCTGCAACGTGAAC

CACAAGCCTTCCAACACCAAGGTGGACAAGCGGGTGGAGCCTAAGTCCTGCGACAAGACC

CACACCTGTCCTCCATGCCCTGCCCCTGAGCTGCTGGGCGGACCCTCCGTGTTCCTGTTC

CCTCCAAAGCCTAAGGACACCCTGATGATCTCCCGGACCCCTGAAGTGACCTGCGTGGTG

GTGGACGTGTCCCACGAGGATCCTGAAGTGAAGTTCAATTGGTACGTGGACGGCGTGGAG

GTGCACAACGCCAAGACCAAGCCTCGGGAGGAACAGTACAACTCCACCTACCGGGTGGTG

TCCGTGCTGACCGTGCTGCACCAGGACTGGCTGAACGGCAAAGAGTACAAGTGCAAGGTC

TCCAACAAGGCCCTGCCTGCCCCTATCGAAAAGACCATCTCCAAGGCCAAGGGCCAGCCT

CGGGAACCTCAGGTGTACACACTGCCTCCCAGCAGGGACGAGCTGACCAAGAACCAGGTG

TCCCTGACCTGTCTGGTGAAGGGCTTCTACCCTTCCGATATCGCCGTGGAGTGGGAGTCT

AACGGCCAGCCTGAGAACAACTACAAGACCACCCCTCCTGTGCTGGACTCCGACGGCTCC

TTCTTCCTGTACTCCAAACTGACCGTGGACAAGTCCCGGTGGCAGCAGGGCAACGTGTTC

TCCTGCTCCGTGATGCACGAGGCCCTGCACAACCACTACACCCAGAAGTCCCTGTCTCTG

```
                                                  -continued
TCCCCTGGCAAGTGAAAGCTTGAGCTCATGGCGCGCCTAGGCCTTGACGGCCTTCCG Heavy chain D58N/D103N/E105Q mutant (shown here with the signal peptide)
[SEQ ID No. 19]:
CGGAAGGCCCATGAGGCCAGTTAATTAAGAGGTACCAAGCTTGCCACCATGGACTGGACC

TGGCGGATCCTGTTTCTGGTGGCCGCTGCTACCGGCACACACGCCCAGGTGCAGCTGAAG

CAGTCTGGCCCTGGCCTGGTGCAGCCTTCCCAGTCCCTGTCCATCACCTGTACCGTGTCC

GGCTTCTCCCTGACCAACTACGGCGTGCACTGGGTGCGCCAGTCTCCAGGCAAGGGCCTG

GAATGGCTGGGAGTGATTTGGTCCGGCGGCAACACC■■TACAACACCCCTTTCACCTCC

CGGCTGTCCATCAACAAGGACAACTCCAAGTCCCAGGTGTTCTTCAAGATGAACTCCCTG

CAGTCCAACGACACCGCCATCTACTACTGCGCCAGGGCTCTGACCTACTAC■■TAC■

TTCGCCTACTGGGGCCAGGGCACCCTGGTGACCGTGTCCGCCGCTTCCACCAAGGGCCCT

AGCGTGTTCCCTCTGGCCCCTTCCAGCAAGTCTACCTCTGGCGGCACCGCTGCTCTGGGC

TGCCTGGTGAAGGACTACTTCCCTGAGCCTGTGACAGTGTCCTGGAACTCTGGCGCCCTG

ACCTCCGGAGTGCACACCTTCCCTGCTGTGCTGCAGTCCTCCGGCCTGTACTCCCTGTCC

TCCGTGGTGACAGTGCCTTCCTCCAGCCTGGGCACACAGACCTACATCTGCAACGTGAAC

CACAAGCCTTCCAACACCAAGGTGGACAAGCGGGTGGAGCCTAAGTCCTGCGACAAGACC

CACACCTGTCCTCCATGCCCTGCCCCTGAGCTGCTGGGCGGACCCTCCGTGTTCCTGTTC

CCTCCAAAGCCTAAGGACACCCTGATGATCTCCCGGACCCCTGAAGTGACCTGCGTGGTG

GTGGACGTGTCCCACGAGGATCCTGAAGTGAAGTTCAATTGGTACGTGGACGGCGTGGAG

GTGCACAACGCCAAGACCAAGCCTCGGGAGGAACAGTACAACTCCACCTACCGGGTGGTG

TCCGTGCTGACCGTGCTGCACCAGGACTGGCTGAACGGCAAAGAGTACAAGTGCAAGGTC

TCCAACAAGGCCCTGCCTGCCCCTATCGAAAAGACCATCTCCAAGGCCAAGGGCCAGCCT

CGGGAACCTCAGGTGTACACACTGCCTCCCAGCAGGGACGAGCTGACCAAGAACCAGGTG

TCCCTGACCTGTCTGGTGAAGGGCTTCTACCCTTCCGATATCGCCGTGGAGTGGGAGTCT

AACGGCCAGCCTGAGAACAACTACAAGACCACCCCTCCTGTGCTGGACTCCGACGGCTCC

TTCTTCCTGTACTCCAAACTGACCGTGGACAAGTCCCGGTGGCAGCAGGGCAACGTGTTC

TCCTGCTCCGTGATGCACGAGGCCCTGCACAACCACTACACCCAGAAGTCCCTGTCTCTG

TCCCCTGGCAAGTGAAAGCTTGAGCTCATGGCGCGCCTAGGCCTTGACGGCCTTCCG
```

Amino acid sequences constituting the antibody wild type and mutant chains are provided below. The signal peptide is indicated using lower case letters, and is not included in the residue numbering. Mutated positions are bolded in mutant sequences.

```
Light chain wild-type [SEQ ID No. 20]:
mvlqtqvfislllwisgaygDILLTQSPVILSVSPGERVSFSCRAS

QSIGTNIHWYQQRTNGSPRLLIKYASESISGIPSRFSGSGSGTDFT

LSINSVESEDIADYYCQQNNNWPTTFGAGTKLELKRTVAAPSVFIF

PPSDEQLKSGTASVVCLLNNFYPREAKVQWKVDNALQSGNSQESVT

EQDSKDSTYSLSSTLTLSKADYEKHKVYACEVTHQGLSSPVTKSFN

RGEC

Light chain E58K mutant [SEQ ID No. 21]:
mvlqtqvfislllwisgaygDILLTQSPVILSVSPGERVSFSCRAS

QSIGTNIHWYQQRTNGSPRLLIKYASKSISGIPSRFSGSGSGTDFT

LSINSVESEDIADYYCQQNNNWPTTFGAGTKLELKRTVAAPSVFIF

PPSDEQLKSGTASVVCLENNEYPREAKVQWKVDNALQSGNSQESVT

EQDSKDSTYSLSSTLTLSKADYEKHKVYACEVTHQGLSSPVTKSFN

RGEC

Light chain W94A mutant [SEQ ID No. 22]:
mvlqtqvfislllwisgaygDILLTQSPVILSVSPGERVSFSCRAS

QSIGTNIHWYQQRTNGSPRLLIKYASESISGIPSRFSGSGSGTDFT

LSINSVESEDIADYYCQQNNNAPTTFGAGTKLELKRTVAAPSVFIF

PPSDEQLKSGTASVVCLLNNFYPREAKVQWKVDNALQSGNSQESVT

EQDSKDSTYSLSSTLTLSKADYEKHKVYACEVTHQGLSSPVTKSFN

RGEC
```

Heavy chain wild-type [SEQ ID No. 23]:
mdwtwrilflvaaatgthaQVQLKQSGPGLVQPSQSLSITCTVSGF
SLTNYGVHWVRQSPGKGLEWLGVIWSGGNTDYNTPFTSRLSINKDN
SKSQVFFENESLQSNDTAIYYCARALTYYDYEFAYWGQGTLVTVSA
ASTKGPSVFPLAPSSKSTSGGTAALGCLVKDYFPEPVTVSWNSGAL
TSGVHTFPAVLQSSGLYSLSSVVTVPSSSLGTQTYICNVNHKPSNT
KVDKRVEPKSCDKTHTCPPCPAPELLGGPSVFLFPPKPKDTLMISR
TPEVTCVVVDVSHEDPEVKFNWYVDGVEVHNAKTKPREEQYNSTYR
VVSVLTVLHQDWLNGKEYKCKVSNKALPAPIEKTISKAKGQPREPQ
VYTLPPSRDELTKNQVSLTCLVKGFYPSDIAVEWESNGQPENNYKT
TPPVLDSDGSFFLYSKLTVDKSRWQQGNVFSCSVMHEALHNHYTQK
SLSLSPGK Heavy chain Y101 mutant [SEQ ID No. 24]:
mdwtwrilflvaaatgthaQVQLKQSGPGLVQPSQSLSITCTVSGF
SLTNYGVHWVRQSPGKGLEWLGVIWSGGNTDYNTPFTSRLSINKDN
SKSQVFFKMNSLQSNDTAIYYCARALTAYDYEFAYWGQGTLVTVSA
ASTKGPSVFPLAPSSKSTSGGTAALGCLVKDYFPEPVTVSWNSGAL
TSGVHTFPAVLQSSGLYSLSSVVTVPSSSLGTQTYICNVNHKPSNT
KVDKRVEPKSCDKTHTCPPCPAPELLGGPSVFLFPPKPKDTLMISR
TPEVTCVVVDVSHEDPEVKFNWYVDGVEVHNAKTKPREEQYNSTYR
VVSVLTVLHQDWLNGKEYKCKVSNKALPAPIEKTISKAKGQPREPQ
VYTLPPSRDELTKNQVSLTCLVKGFYPSDIAVEWESNGQPENNYKT
TPPVLDSDGSFFLYSKLTVDKSRWQQGNVFSCSVMHEALHNHYTQK
SLSLSPGK Heavy chain Y102 mutant [SEQ ID No. 25]:
mdwtwrilflvaaatgthaQVQLKQSGPGLVQPSQSLSITCTVSGF
SLTNYGVHWVRQSPGKGLEWLGVIWSGGNTDYNTPFTSRLSINKDN
SKSQVFFKMNSLQSNDTAIYYCARALTYADYEFAYWGQGTLVTVSA
ASTKGPSVFPLAPSSKSTSGGTAALGCLVKDYFPEPVTVSWNSGAL
TSGVHTFPAVLQSSGLYSLSSVVTVPSSSLGTQTYICNVNHKPSNT
KVDKRVEPKSCDKTHTCPPCPAPELLGGPSVFLFPPKPKDTLMISR
TPEVTCVVVDVSHEDPEVKFNWYVDGVEVHNAKTKPREEQYNSTYR
VVSVLTVLHQDWLNGKEYKCKVSNKALPAPIEKTISKAKGQPREPQ
VYTLPPSRDELTKNQVSLTCLVKGFYPSDIAVEWESNGQPENNYKT
TPPVLDSDGSFFLYSKITVDKSRWQQGNVFSCSVMHEALHNHYTQK
SLSLSPGK Heavy chain D103N mutant [SEQ ID No. 26]:
mdwtwrilflvaaatgthaQVQLKQSGPGLVQPSQSLSITCTVSGF
SLTNYGVHWVRQSPGKGLEWLGVIWSGGNTDYNTPFTSRLSINKDN
SKSQVFFKMNSLQSNDTAIYYCARALTYYNYEFAYWGQGTLVTVSA
ASTKGPSVFPLAPSSKSTSGGTAALGCLVKDYFPEPVTVSWNSGAL
TSGVHTFPAVLQSSGLYSLSSVVTVPSSSLGTQTYICNVNHKPSNT
KVDKRVEPKSCDKTHTCPPCPAPELLGGPSVFLFPPKPKDTLMISR
TPEVTCVVVDVSHEDPEVKFNWYVDGVEVHNAKTKPREEQYNSTYR
VVSVLTVLHQDWLNGKEYKCKVSNKALPAPIEKTISKAKGQPREPQ
VYTLPPSRDELTKNQVSLTCLVKGFYPSDIAVEWESNGQPENNYKT
TPPVLDSDGSFFLYSKLTVDKSRWQQGNVFSCSVMHEALHNHYTQK
SLSLSPGK Heavy chain D58N/D103N mutant [SEQ ID No. 27]:
mdwtwrmlflvaaatgthaQVQLKQSGPGLVQPSQSLSITCTVSGF
SLTNYGVHWVRQSPGKGLEWLGVIWSGGNTNYNTPFTSRLSINKDN
SKSQVFFKMNSLQSNDTAIYYCARALTYYNYEFAYWGQGTLVTVSA
ASTKGPSVFPLAPSSKSTSGGTAALGCLVKDYFPEPVTVSWNSGAL
TSGVHTFPAVLQSSGLYSLSSVVTVPSSSLGTQTYICNVNHKPSNT
KVDKRVEPKSCDKTHTCPPCPAPELLGGPSVFLFPPKPKDTLMISR
TPEVTCVVVDVSHEDPEVKFNWYVDGVEVHNAKTKPREEQYNSTYR
VVSVLTVLHQDWLNGKEYKCKVSNKALPAPIEKTISKAKGQPREPQ
VYTLPPSRDELTKNQVSLTCLVKGFYPSDIAVEWESNGQPENNYKT
TPPVLDSDGSFFLYSKLTVDKSRWQQGNVFSCSVMHEALHNHYTQK
SLSLSPGK Heavy chain D58N/D103N/E105Q mutant [SEQ ID No. 28]:
mdwtwrilflvaaatgthaQVQLKQSGPGLVQPSQSLSITCTVSGF
SLTNYGVHWVRQSPGKGLEWLGVIWSGGNTNYNTPFTSRLSINKDN
SKSQVFFKMNSLQSNDTAIYYCARALTYYNYQFAYWGQGTLVTVSA
ASTKGPSVFPLAPSSKSTSGGTAALGCLVKDYFPEPVTVSWNSGAL
TSGVHTFPAVLQSSGLYSLSSVVTVPSSSLGTQTYICNVNHKPSNT
KVDKRVEPKSCDKTHTCPPCPAPELLGGPSVFLFPPKPKDTLMISR
TPEVTCVVVDVSHEDPEVKFNWYVDGVEVHNAKTKPREEQYNSTYR
VVSVLTVLHQDWLNGKEYKCKVSNKALPAPIEKTISKAKGQPREPQ
VYTLPPSRDELTKNQVSLTCLVKGFYPSDIAVEWESNGQPENNYKT
TPPVLDSDGSFFLYSKLTVDKSRWQQGNVFSCSVMHEALHNHYTQK
SLSLSPGK

SEQUENCE LISTING

<160> NUMBER OF SEQ ID NOS: 30

<210> SEQ ID NO 1
<211> LENGTH: 5
<212> TYPE: PRT

```
<213> ORGANISM: Homo sapiens

<400> SEQUENCE: 1

Asn Tyr Gly Val His
1               5

<210> SEQ ID NO 2
<211> LENGTH: 16
<212> TYPE: PRT
<213> ORGANISM: Homo sapiens
<220> FEATURE:
<221> NAME/KEY: MISC_FEATURE
<222> LOCATION: (9)..(9)
<223> OTHER INFORMATION: X is D or an amino acid having a side chain
      that is nonpolar and/or is charge neutral or positive and/or is
      not small.

<400> SEQUENCE: 2

Val Ile Trp Ser Gly Gly Asn Thr Xaa Tyr Asn Thr Pro Phe Thr Ser
1               5                   10                  15

<210> SEQ ID NO 3
<211> LENGTH: 11
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: X is Y or an amino acid having a side chain
      that is nonpolar and/or a side chain that is non-neutral and/or a
      side chain that is not large.
<220> FEATURE:
<221> NAME/KEY: MISC_FEATURE
<222> LOCATION: (5)..(5)
<223> OTHER INFORMATION: X is Y or an amino acid having a side chain
      that is nonpolar and/or a side chain that is non-neutral and/or a
      side chain that is not large.
<220> FEATURE:
<221> NAME/KEY: MISC_FEATURE
<222> LOCATION: (6)..(6)
<223> OTHER INFORMATION: X is D or an amino acid having a side chain
      that is nonpolar and/or is charge neutral or positive and/or is
      not small.
<220> FEATURE:
<221> NAME/KEY: MISC_FEATURE
<222> LOCATION: (8)..(8)
<223> OTHER INFORMATION: X is E or an amino acid having a side chain
      that is nonpolar and/or is charge neutral or positive and/or is
      not small.

<400> SEQUENCE: 3

Ala Leu Thr Xaa Xaa Xaa Tyr Xaa Phe Ala Tyr
1               5                   10

<210> SEQ ID NO 4
<211> LENGTH: 11
<212> TYPE: PRT
<213> ORGANISM: Homo sapiens

<400> SEQUENCE: 4

Arg Ala Ser Gln Ser Ile Gly Thr Asn Ile His
1               5                   10

<210> SEQ ID NO 5
<211> LENGTH: 6
<212> TYPE: PRT
<213> ORGANISM: Homo sapiens
<220> FEATURE:
<221> NAME/KEY: MISC_FEATURE
<222> LOCATION: (3)..(3)
```

```
<223> OTHER INFORMATION: X is E or an amino acid having a side chain
      that is either nonpolar and/or is neutral or positive in charge
      and/or may not be small.

<400> SEQUENCE: 5

Ala Ser Xaa Ser Ile Ser
1               5

<210> SEQ ID NO 6
<211> LENGTH: 9
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: X is W or an amino acid having a side chain
      that is either polar and/or is charge positive or negative and/or
      is not bulky.

<400> SEQUENCE: 6

Gln Gln Asn Asn Asn Xaa Pro Thr Thr
1               5

<210> SEQ ID NO 7
<211> LENGTH: 107
<212> TYPE: PRT
<213> ORGANISM: Homo sapiens
<220> FEATURE:
<221> NAME/KEY: MISC_FEATURE
<222> LOCATION: (53)..(53)
<223> OTHER INFORMATION: X is E or an amino acid having a side chain
      that is either nonpolar and/or is neutral or positive in charge
      and/or may not be small.
<220> FEATURE:
<221> NAME/KEY: MISC_FEATURE
<222> LOCATION: (94)..(94)
<223> OTHER INFORMATION: X is W or an amino acid having a side chain
      that is either polar and/or is charge positive or negative and/or
      is not bulky.

<400> SEQUENCE: 7

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
                20                  25                  30

Ile His Trp Tyr Gln Gln Arg Thr Asn Gly Ser Pro Arg Leu Leu Ile
            35                  40                  45

Lys Tyr Ala Ser Xaa Ser Ile Ser Gly Ile Pro Ser Arg Phe Ser Gly
50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Xaa Pro Thr
                85                  90                  95

Thr Phe Gly Ala Gly Thr Lys Leu Glu Leu Lys
                100                 105

<210> SEQ ID NO 8
<211> LENGTH: 119
<212> TYPE: PRT
<213> ORGANISM: Homo sapiens
<220> FEATURE:
<221> NAME/KEY: MISC_FEATURE
<222> LOCATION: (58)..(58)
<223> OTHER INFORMATION: X is D or an amino acid having a side chain
      that is nonpolar and/or is charge neutral or positive and/or is
      not small.
<220> FEATURE:
```

```
<221> NAME/KEY: MISC_FEATURE
<222> LOCATION: (101)..(101)
<223> OTHER INFORMATION: X is Y or an amino acid having a side chain
      that is nonpolar and/or a side chain that is non-neutral and/or a
      side chain that is not large.
<220> FEATURE:
<221> NAME/KEY: MISC_FEATURE
<222> LOCATION: (102)..(102)
<223> OTHER INFORMATION: X is Y or an amino acid having a side chain
      that is nonpolar and/or a side chain that is non-neutral and/or a
      side chain that is not large.
<220> FEATURE:
<221> NAME/KEY: MISC_FEATURE
<222> LOCATION: (103)..(103)
<223> OTHER INFORMATION: X is D or an amino acid having a side chain
      that is nonpolar and/or is charge neutral or positive and/or is
      not small.
<220> FEATURE:
<221> NAME/KEY: MISC_FEATURE
<222> LOCATION: (105)..(105)
<223> OTHER INFORMATION: X is E or an amino acid having a side chain
      that is nonpolar and/or is charge neutral or positive and/or is
      not small.

<400> SEQUENCE: 8

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Xaa Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Xaa Xaa Xaa Tyr Xaa Phe Ala Tyr Trp Gly Gln Gly
            100                 105                 110

Thr Leu Val Thr Val Ser Ala
        115

<210> SEQ ID NO 9
<211> LENGTH: 213
<212> TYPE: PRT
<213> ORGANISM: Homo sapiens
<220> FEATURE:
<221> NAME/KEY: MISC_FEATURE
<222> LOCATION: (53)..(53)
<223> OTHER INFORMATION: X is E or an amino acid having a side chain
      that is either nonpolar and/or is neutral or positive in charge
      and/or may not be small.
<220> FEATURE:
<221> NAME/KEY: MISC_FEATURE
<222> LOCATION: (94)..(94)
<223> OTHER INFORMATION: X is W or an amino acid having a side chain
      that is either polar and/or is charge positive or negative and/or
      is not bulky.

<400> SEQUENCE: 9

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45
```

```
Lys Tyr Ala Ser Xaa Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Xaa Pro Thr
                85                  90                  95

Thr Phe Gly Ala Gly Thr Lys Leu Glu Leu Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu
    210
```

<210> SEQ ID NO 10
<211> LENGTH: 449
<212> TYPE: PRT
<213> ORGANISM: Homo sapiens
<220> FEATURE:
<221> NAME/KEY: MISC_FEATURE
<222> LOCATION: (58)..(58)
<223> OTHER INFORMATION: X is D or an amino acid having a side chain
      that is nonpolar and/or is charge neutral or positive and/or is
      not small.
<220> FEATURE:
<221> NAME/KEY: MISC_FEATURE
<222> LOCATION: (101)..(101)
<223> OTHER INFORMATION: X is Y or an amino acid having a side chain
      that is nonpolar and/or a side chain that is non-neutral and/or a
      side chain that is not large.
<220> FEATURE:
<221> NAME/KEY: MISC_FEATURE
<222> LOCATION: (102)..(102)
<223> OTHER INFORMATION: X is Y or an amino acid having a side chain
      that is nonpolar and/or a side chain that is non-neutral and/or a
      side chain that is not large.
<220> FEATURE:
<221> NAME/KEY: MISC_FEATURE
<222> LOCATION: (103)..(103)
<223> OTHER INFORMATION: X is D or an amino acid having a side chain
      that is nonpolar and/or is charge neutral or positive and/or is
      not small.
<220> FEATURE:
<221> NAME/KEY: MISC_FEATURE
<222> LOCATION: (105)..(105)
<223> OTHER INFORMATION: X is E or an amino acid having a side chain
      that is nonpolar and/or is charge neutral or positive and/or is
      not small.

<400> SEQUENCE: 10

```
Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
                20                  25                  30

Gly Val His Trp Val Arg Gln Ser Pro Gly Lys Gly Leu Glu Trp Leu
            35                  40                  45
```

```
Gly Val Ile Trp Ser Gly Gly Asn Thr Xaa Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Xaa Xaa Xaa Tyr Xaa Phe Ala Tyr Trp Gly Gln Gly
                100                 105                 110

Thr Leu Val Thr Val Ser Ala Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Arg Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys
```

<210> SEQ ID NO 11
<211> LENGTH: 780
<212> TYPE: DNA
<213> ORGANISM: Homo sapiens

<400> SEQUENCE: 11

| gtttaaacga attcgccctt gaggtaccaa gcttgccacc atggtgctgc agacccaggt | 60 |
| gttcatctcc ctgctgctgt ggatctctgg cgcctacggc gacatcctgc tgacccagtc | 120 |
| ccccgtgatc ctgtccgtgt ccctggcga gcgggtgtcc ttctcttgcc gggcctccca | 180 |
| gtccatcggc accaacatcc actggtatca gcagcggacc aacggctccc ctcggctgct | 240 |
| gatcaagtac gcctccgagt ctatctccgg catcccttcc cggttctccg gctctggctc | 300 |
| cggcaccgac ttcaccctgt ccatcaactc cgtggagtcc gaggatatcg ccgactacta | 360 |
| ctgccagcag aacaacaact ggcctaccac cttcggcgct ggcaccaagc tggaactgaa | 420 |
| gcggaccgtg gccgctcctt ccgtgttcat cttcccacct tccgacgagc agctgaagtc | 480 |
| cggcaccgcc tctgtggtgt gcctgctgaa caacttctac cctcgggagg ccaaggtgca | 540 |
| gtggaaggtg gacaacgccc tgcagtccgg caactcccag gaatccgtca ccgagcagga | 600 |
| ctccaaggac tctacctact ccctgtcctc caccctgacc ctgtccaagg ccgactacga | 660 |
| gaagcacaag gtgtacgcct gcgaagtgac ccaccagggc ctgtccagcc ctgtgaccaa | 720 |
| gtccttcaac cggggcgagt gctgaaagct tgagctcagt aagggcgaat cgcggccgc | 780 |

<210> SEQ ID NO 12
<211> LENGTH: 795
<212> TYPE: DNA
<213> ORGANISM: Homo sapiens

<400> SEQUENCE: 12

| cggaaggccc atgaggccag ttaattaaga ggtaccaagc ttgccaccat ggtgctgcag | 60 |
| acccaggtgt tcatctccct gctgctgtgg atctctggcg cctacggcga catcctgctg | 120 |
| acccagtccc ccgtgatcct gtccgtgtcc ctggcgagc gggtgtcctt ctcttgccgg | 180 |
| gcctcccagt ccatcggcac caacatccac tggtatcagc agcggaccaa cggctcccct | 240 |
| cggctgctga tcaagtacgc ctccgagtct atctccggca tcccttcccg gttctccggc | 300 |
| tctggctccg gcaccgactt caccctgtcc atcaactccg tggagtccga ggatatcgcc | 360 |
| gactactact gccagcagaa caacaactgg cctaccacct tcggcgctgg caccaagctg | 420 |
| gaactgaagc ggaccgtggc cgctccttcc gtgttcatct tcccaccttc cgacgagcag | 480 |
| ctgaagtccg gcaccgcctc tgtggtgtgc ctgctgaaca acttctaccc tcgggaggcc | 540 |
| aaggtgcagt ggaaggtgga caacgccctg cagtccggca actcccagga atccgtcacc | 600 |
| gagcaggact ccaaggactc tacctactcc ctgtcctcca ccctgaccct gtccaaggcc | 660 |
| gactacgaga agcacaaggt gtacgcctgc gaagtgaccc accagggcct gtccagccct | 720 |
| gtgaccaagt ccttcaaccg gggcgagtgc tgaaagcttg agctcatggc gcgcctaggc | 780 |
| cttgacggcc ttccg | 795 |

<210> SEQ ID NO 13
<211> LENGTH: 795
<212> TYPE: DNA
<213> ORGANISM: Homo sapiens

<400> SEQUENCE: 13

```
cggaaggccc atgaggccag ttaattaaga ggtaccaagc ttgccaccat ggtgctgcag      60
acccaggtgt tcatctccct gctgctgtgg atctctggcg cctacggcga catcctgctg     120
acccagtccc ccgtgatcct gtccgtgtcc cctggcgagc gggtgtcctt ctcttgccgg     180
gcctcccagt ccatcggcac caacatccac tggtatcagc agcggaccaa cggctcccct     240
cggctgctga tcaagtacgc ctccgagtct atctccggca tcccttcccg gttctccggc     300
tctggctccg gcaccgactt caccctgtcc atcaactccg tggagtccga ggatatcgcc     360
gactactact gccagcagaa caacaacgcc cctaccacct cggcgctgg caccaagctg      420
gaactgaagc ggaccgtggc cgctccttcc gtgttcatct cccaccttc cgacgagcag      480
ctgaagtccg gcaccgcctc tgtggtgtgc ctgctgaaca acttctaccc tcgggaggcc     540
aaggtgcagt ggaaggtgga caacgccctg cagtccggca actcccagga atccgtcacc     600
gagcaggact ccaaggactc tacctactcc ctgtcctcca ccctgaccct gtccaaggcc     660
gactacgaga agcacaaggt gtacgcctgc gaagtgaccc accagggcct gtccagccct     720
gtgaccaagt ccttcaaccg gggcgagtgc tgaaagcttg agctcatggc gcgcctaggc     780
cttgacggcc ttccg                                                      795
```

<210> SEQ ID NO 14
<211> LENGTH: 1497
<212> TYPE: DNA
<213> ORGANISM: Homo sapiens

<400> SEQUENCE: 14

```
cgaattgaag gaaggccgtc aaggccgcat ggtaccaagc ttgccaccat ggactggacc      60
tggcggatcc tgtttctggt ggccgctgct accggcacac acgcccaggt gcagctgaag     120
cagtctggcc ctggcctggt gcagccttcc cagtccctgt ccatcacctg taccgtgtcc     180
ggcttctccc tgaccaacta cggcgtgcac tgggtgcgcc agtctccagg caagggcctg     240
gaatggctgg gagtgatttg gtccggcggc aacaccgact acaacacccc tttcacctcc     300
cggctgtcca tcaacaagga caactccaag tcccaggtgt tcttcaagat gaactccctg     360
cagtccaacg acaccgccat ctactactgc gccagggctc tgacctacta cgactacgag     420
ttcgcctact ggggccaggg caccctggtg accgtgtccg ccgcttccac caagggccct     480
agcgtgttcc ctctggcccc ttccagcaag tctacctctg gcggcaccgc tgctctgggc     540
tgcctggtga aggactactt ccctgagcct gtgacagtgt cctggaactc tggcgccctg     600
acctccggag tgcacacctt ccctgctgtg ctgcagtcct ccggcctgta ctccctgtcc     660
tccgtggtga cagtgccttc ctccagcctg ggcacacaga cctacatctg caacgtgaac     720
cacaagccct tccacaccaa ggtggacaag cgggtggagc ctaagtcctg cgacaagacc     780
cacacctgtc ctccatgccc tgccctgag ctgctgggcg accctccgt gttcctgttc      840
cctccaaagc ctaaggacac cctgatgatc tcccggaccc ctgaagtgac ctgcgtggtg     900
gtggacgtgt cccacgagga tcctgaagtg aagttcaatt ggtacgtgga cggcgtggag     960
gtgcacaacg ccaagaccaa gcctcgggag gaacagtaca actccaccta ccgggtggtg    1020
tccgtgctga ccgtgctgca ccaggactgg ctgaacggca agagtacaa gtgcaaggtc     1080
tccaacaagg ccctgcctgc ccctatcgaa aagaccatct ccaaggccaa gggcagcct     1140
cgggaacctc aggtgtacac actgcctccc agcagggacg agctgaccaa gaaccaggtg    1200
```

| | |
|---|---|
| tccctgacct gtctggtgaa gggcttctac ccttccgata tcgccgtgga gtgggagtct | 1260 |
| aacggccagc ctgagaacaa ctacaagacc acccctcctg tgctggactc cgacggctcc | 1320 |
| ttcttcctgt actccaaact gaccgtggac aagtcccggt ggcagcaggg caacgtgttc | 1380 |
| tcctgctccg tgatgcacga ggccctgcac aaccactaca cccagaagtc cctgtctctg | 1440 |
| tcccctggca agtgaaagct tgagctcctg ggcctcatgg gccttccttt cactgcc | 1497 |

<210> SEQ ID NO 15
<211> LENGTH: 1497
<212> TYPE: DNA
<213> ORGANISM: Homo sapiens

<400> SEQUENCE: 15

| | |
|---|---|
| cggaaggccc atgaggccag ttaattaaga ggtaccaagc ttgccaccat ggactggacc | 60 |
| tggcggatcc tgtttctggt ggccgctgct accggcacac acgcccaggt gcagctgaag | 120 |
| cagtctggcc ctggcctggt gcagccttcc cagtccctgt ccatcacctg taccgtgtcc | 180 |
| ggcttctccc tgaccaacta cggcgtgcac tgggtgcgcc agtctccagg caagggcctg | 240 |
| gaatggctgg gagtgatttg gtccggcggc aacaccgact acaacacccc tttcacctcc | 300 |
| cggctgtcca tcaacaagga caactccaag tcccaggtgt tcttcaagat gaactccctg | 360 |
| cagtccaacg acaccgccat ctactactgc gccagggctc tgaccgccta cgactacgag | 420 |
| ttcgcctact ggggccaggg caccctggtg accgtgtccg ccgcttccac caagggccct | 480 |
| agcgtgttcc ctctggcccc ttccagcaag tctacctctg gcggcaccgc tgctctgggc | 540 |
| tgcctggtga aggactactt ccctgagcct gtgacagtgt cctggaactc tggcgccctg | 600 |
| acctccggag tgcacacctt ccctgctgtg ctgcagtcct ccggcctgta ctccctgtcc | 660 |
| tccgtggtga cagtgccttc ctccagcctg ggcacacaga cctacatctg caacgtgaac | 720 |
| cacaagcctt ccaacaccaa ggtggacaag cgggtggagc ctaagtcctg cgacaagacc | 780 |
| cacacctgtc ctccatgccc tgcccctgag ctgctgggcg gacccccgt gttcctgttc | 840 |
| cctccaaagc ctaaggacac cctgatgatc tcccggaccc ctgaagtgac ctgcgtggtg | 900 |
| gtggacgtgt cccacgagga tcctgaagtg aagttcaatt ggtacgtgga cggcgtggag | 960 |
| gtgcacaacg ccaagaccaa gcctcgggag gaacagtaca actccaccta ccgggtggtg | 1020 |
| tccgtgctga ccgtgctgca ccaggactgg ctgaacggca agagtacaa gtgcaaggtc | 1080 |
| tccaacaagg ccctgcctgc ccctatcgaa aagaccatct ccaaggccaa gggccagcct | 1140 |
| cgggaacctc aggtgtacac actgcctccc agcagggacg agctgaccaa gaaccaggtg | 1200 |
| tccctgacct gtctggtgaa gggcttctac ccttccgata tcgccgtgga gtgggagtct | 1260 |
| aacggccagc ctgagaacaa ctacaagacc acccctcctg tgctggactc cgacggctcc | 1320 |
| ttcttcctgt actccaaact gaccgtggac aagtcccggt ggcagcaggg caacgtgttc | 1380 |
| tcctgctccg tgatgcacga ggccctgcac aaccactaca cccagaagtc cctgtctctg | 1440 |
| tcccctggca agtgaaagct tgagctcatg gcgcgcctag ccttgacgg ccttccg | 1497 |

<210> SEQ ID NO 16
<211> LENGTH: 1497
<212> TYPE: DNA
<213> ORGANISM: Homo sapiens

<400> SEQUENCE: 16

| | |
|---|---|
| cggaaggccc atgaggccag ttaattaaga ggtaccaagc ttgccaccat ggactggacc | 60 |
| tggcggatcc tgtttctggt ggccgctgct accggcacac acgcccaggt gcagctgaag | 120 |

-continued

```
cagtctggcc ctggcctggt gcagccttcc cagtccctgt ccatcacctg taccgtgtcc      180
ggcttctccc tgaccaacta cggcgtgcac tgggtgcgcc agtctccagg caagggcctg      240
gaatggctgg gagtgatttg gtccggcggc aacaccgact acaacacccc tttcacctcc      300
cggctgtcca tcaacaagga caactccaag tcccaggtgt tcttcaagat gaactccctg      360
cagtccaacg acaccgccat ctactactgc gccagggctc tgacctacgc cgactacgag      420
ttcgcctact ggggccaggg caccctggtg accgtgtccg ccgcttccac caagggccct      480
agcgtgttcc ctctggcccc ttccagcaag tctacctctg gcggcaccgc tgctctgggc      540
tgcctggtga aggactactt ccctgagcct gtgacagtgt cctggaactc tggcgccctg      600
acctccggag tgcacacctt ccctgctgtg ctgcagtcct ccggcctgta ctccctgtcc      660
tccgtggtga cagtgccttc ctccagcctg ggcacacaga cctacatctg caacgtgaac      720
cacaagcctt ccaacaccaa ggtggacaag cgggtggagc taagtcctgc gacaagacc       780
cacacctgtc ctccatgccc tgccctgag ctgctgggcg gaccctccgt gttcctgttc        840
cctccaaagc ctaaggacac cctgatgatc tcccggaccc ctgaagtgac ctgcgtggtg      900
gtggacgtgt cccacgagga tcctgaagtg aagttcaatt ggtacgtgga cggcgtggag      960
gtgcacaacg ccaagaccaa gcctcgggag gaacagtaca actccaccta ccgggtggtg     1020
tccgtgctga ccgtgctgca ccaggactgg ctgaacggca agagtacaa gtgcaaggtc      1080
tccaacaagg ccctgcctgc ccctatcgaa aagaccatct ccaaggccaa gggccagcct     1140
cgggaacctc aggtgtacac actgcctccc agcagggacg agctgaccaa gaaccaggtg     1200
tccctgacct gtctggtgaa gggcttctac ccttccgata tcgccgtgga gtgggagtct     1260
aacggccagc ctgagaacaa ctacaagacc ccctcctg tgctggactc cgacggctcc       1320
ttcttcctgt actccaaact gaccgtggac aagtcccggt ggcagcaggg caacgtgttc     1380
tcctgctccg tgatgcacga ggccctgcac aaccactaca cccagaagtc cctgtctctg     1440
tccctggca agtgaaagct tgagctcatg gcgcgcctag gccttgacgg ccttccg         1497
```

<210> SEQ ID NO 17
<211> LENGTH: 1497
<212> TYPE: DNA
<213> ORGANISM: Homo sapiens

<400> SEQUENCE: 17

```
cggaaggccc atgaggccag ttaattaaga ggtaccaagc ttgccaccat ggactggacc       60
tggcggatcc tgtttctggt ggccgctgct accggcacac acgcccaggt gcagctgaag      120
cagtctggcc ctggcctggt gcagccttcc cagtccctgt ccatcacctg taccgtgtcc      180
ggcttctccc tgaccaacta cggcgtgcac tgggtgcgcc agtctccagg caagggcctg      240
gaatggctgg gagtgatttg gtccggcggc aacaccgact acaacacccc tttcacctcc      300
cggctgtcca tcaacaagga caactccaag tcccaggtgt tcttcaagat gaactccctg      360
cagtccaacg acaccgccat ctactactgc gccagggctc tgacctacta caactacgag      420
ttcgcctact ggggccaggg caccctggtg accgtgtccg ccgcttccac caagggccct      480
agcgtgttcc ctctggcccc ttccagcaag tctacctctg gcggcaccgc tgctctgggc      540
tgcctggtga aggactactt ccctgagcct gtgacagtgt cctggaactc tggcgccctg      600
acctccggag tgcacacctt ccctgctgtg ctgcagtcct ccggcctgta ctccctgtcc      660
tccgtggtga cagtgccttc ctccagcctg ggcacacaga cctacatctg caacgtgaac      720
```

```
                                                               -continued
cacaagccttt ccaacaccaa ggtggacaag cgggtggagc ctaagtcctg cgacaagacc    780
cacacctgtc ctccatgccc tgcccctgag ctgctgggcg acccctccgt gttcctgttc    840
cctccaaagc ctaaggacac cctgatgatc tcccggaccc ctgaagtgac ctgcgtggtg    900
gtggacgtgt cccacgagga tcctgaagtg aagttcaatt ggtacgtgga cggcgtggag    960
gtgcacaacg ccaagaccaa gcctcgggag gaacagtaca actccaccta ccgggtggtg   1020
tccgtgctga ccgtgctgca ccaggactgg ctgaacggca agagtacaa gtgcaaggtc    1080 tccaacaagg ccctgcctgc ccctatcgaa aagaccatct ccaaggccaa gggccagcct   1140
cgggaacctc aggtgtacac actgcctccc agcagggacg agctgaccaa gaaccaggtg   1200
tccctgacct gtctggtgaa gggcttctac ccttccgata tcgccgtgga gtgggagtct   1260
aacggccagc ctgagaacaa ctacaagacc acccctcctg tgctggactc cgacggctcc   1320
ttcttcctgt actccaaact gaccgtggac aagtcccggt ggcagcaggg caacgtgttc   1380
tcctgctccg tgatgcacga ggccctgcac aaccactaca cccagaagtc cctgtctctg   1440
tcccctggca agtgaaagct tgagctcatg gcgcgcctag gccttgacgg ccttccg      1497

<210> SEQ ID NO 18
<211> LENGTH: 1497
<212> TYPE: DNA
<213> ORGANISM: Homo sapiens

<400> SEQUENCE: 18
cggaaggccc atgaggccag ttaattaaga ggtaccaagc ttgccaccat ggactggacc     60
tggcggatcc tgtttctggt ggccgctgct accggcacac acgcccaggt gcagctgaag    120
cagtctggcc ctggcctggt gcagccttcc cagtccctgt ccatcacctg taccgtgtcc    180
ggcttctccc tgaccaacta cggcgtgcac tgggtgcgcc agtctccagg caagggcctg    240
gaatggctgg gagtgatttg gtccggcggc aacaccaact acaacacccc tttcacctcc    300
cggctgtcca tcaacaagga caactccaag tcccaggtgt tcttcaagat gaactccctg    360
cagtccaacg acaccgccat ctactactgc gccagggctc tgacctacta caactacgag    420
ttcgcctact ggggccaggg caccctggtg accgtgtccg ccgcttccac caagggccct    480
agcgtgttcc ctctggcccc ttccagcaag tctacctctg gcggcaccgc tgctctgggc    540
tgcctggtga aggactactt ccctgagcct gtgacagtgt cctggaactc tggcgccctg    600
acctccggag tgcacacctt ccctgctgtg ctgcagtcct ccggcctgta ctccctgtcc    660
tccgtggtga cagtgccttc ctccagcctg ggcacacaga cctacatctg caacgtgaac    720
cacaagcctt ccaacaccaa ggtggacaag cgggtggagc ctaagtcctg cgacaagacc    780
cacacctgtc ctccatgccc tgcccctgag ctgctgggcg acccctccgt gttcctgttc    840
cctccaaagc ctaaggacac cctgatgatc tcccggaccc ctgaagtgac ctgcgtggtg    900
gtggacgtgt cccacgagga tcctgaagtg aagttcaatt ggtacgtgga cggcgtggag    960
gtgcacaacg ccaagaccaa gcctcgggag gaacagtaca actccaccta ccgggtggtg   1020
tccgtgctga ccgtgctgca ccaggactgg ctgaacggca agagtacaa gtgcaaggtc    1080 tccaacaagg ccctgcctgc ccctatcgaa aagaccatct ccaaggccaa gggccagcct   1140
cgggaacctc aggtgtacac actgcctccc agcagggacg agctgaccaa gaaccaggtg   1200
tccctgacct gtctggtgaa gggcttctac ccttccgata tcgccgtgga gtgggagtct   1260
aacggccagc ctgagaacaa ctacaagacc acccctcctg tgctggactc cgacggctcc   1320
ttcttcctgt actccaaact gaccgtggac aagtcccggt ggcagcaggg caacgtgttc   1380
```

```
tcctgctccg tgatgcacga ggccctgcac aaccactaca cccagaagtc cctgtctctg   1440 tccoctggca agtgaaagct tgagctcatg gcgcgcctag gccttgacgg ccttccg      1497

<210> SEQ ID NO 19
<211> LENGTH: 1497
<212> TYPE: DNA
<213> ORGANISM: Homo sapiens

<400> SEQUENCE: 19
cggaaggccc atgaggccag ttaattaaga ggtaccaagc ttgccaccat ggactggacc     60
tggcggatcc tgtttctggt ggccgctgct accggcacac acgcccaggt gcagctgaag    120
cagtctggcc ctggcctggt gcagccttcc cagtccctgt ccatcacctg taccgtgtcc    180
ggcttctccc tgaccaacta cggcgtgcac tgggtgcgcc agtctccagg caagggcctg    240
gaatggctgg gagtgatttg gtccggcggc aacaccaact acaacacccc tttcacctcc    300
cggctgtcca tcaacaagga caactccaag tcccaggtgt tcttcaagat gaactccctg    360
cagtccaacg acaccgccat ctactactgc gccagggctc tgacctacta caactaccag    420
ttcgcctact ggggccaggg caccctggtg accgtgtccg ccgcttccac caagggccct    480
agcgtgttcc ctctggcccc ttccagcaag tctacctctg gcggcaccgc tgctctgggc    540
tgcctggtga aggactactt ccctgagcct gtgacagtgt cctggaactc tggcgccctg    600
acctccggag tgcacacctt ccctgctgtg ctgcagtcct ccggcctgta ctccctgtcc    660
tccgtggtga cagtgccttc ctccagcctg ggcacacaga cctacatctg caacgtgaac    720
cacaagcctt ccaacaccaa ggtggacaag cgggtggagc taagtcctg cgacaagacc    780 cacacctgtc ctccatgccc tgcccctgag ctgctgggcg gaccctccgt gttcctgttc    840
cctccaaagc ctaaggacac cctgatgatc tcccggaccc ctgaagtgac ctgcgtggtg    900
gtggacgtgt cccacgagga tcctgaagtg aagttcaatt ggtacgtgga cggcgtggag    960
gtgcacaacg ccaagaccaa gcctcgggag gaacagtaca actccaccta ccgggtggtg   1020
tccgtgctga ccgtgctgca ccaggactgg ctgaacggca agagtacaa gtgcaaggtc   1080 tccaacaagg ccctgcctgc ccctatcgaa aagaccatct ccaaggccaa gggccagcct   1140
cgggaacctc aggtgtacac actgcctccc agcagggacg agctgaccaa gaaccaggtg   1200
tccctgacct gtctggtgaa gggcttctac ccttccgata tcgccgtgga gtgggagtct   1260
aacggccagc ctgagaacaa ctacaagacc acccctcctg tgctggactc cgacggctcc   1320
ttcttcctgt actccaaact gaccgtggac aagtcccggt ggcagcaggg caacgtgttc   1380
tcctgctccg tgatgcacga ggccctgcac aaccactaca cccagaagtc cctgtctctg   1440 tccoctggca agtgaaagct tgagctcatg gcgcgcctag gccttgacgg ccttccg      1497

<210> SEQ ID NO 20
<211> LENGTH: 234
<212> TYPE: PRT
<213> ORGANISM: Homo sapiens

<400> SEQUENCE: 20

Met Val Leu Gln Thr Gln Val Phe Ile Ser Leu Leu Leu Trp Ile Ser
1               5                   10                  15

Gly Ala Tyr Gly Asp Ile Leu Leu Thr Gln Ser Pro Val Ile Leu Ser
            20                  25                  30

Val Ser Pro Gly Glu Arg Val Ser Phe Ser Cys Arg Ala Ser Gln Ser
        35                  40                  45
```

```
Ile Gly Thr Asn Ile His Trp Tyr Gln Gln Arg Thr Asn Gly Ser Pro
 50                  55                  60

Arg Leu Leu Ile Lys Tyr Ala Ser Glu Ser Ile Ser Gly Ile Pro Ser
 65                  70                  75                  80

Arg Phe Ser Gly Ser Gly Ser Gly Thr Asp Phe Thr Leu Ser Ile Asn
                 85                  90                  95

Ser Val Glu Ser Glu Asp Ile Ala Asp Tyr Tyr Cys Gln Gln Asn Asn
                100                 105                 110

Asn Trp Pro Thr Thr Phe Gly Ala Gly Thr Lys Leu Glu Leu Lys Arg
            115                 120                 125

Thr Val Ala Ala Pro Ser Val Phe Ile Phe Pro Pro Ser Asp Glu Gln
        130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 21
<211> LENGTH: 234
<212> TYPE: PRT
<213> ORGANISM: Homo sapiens

<400> SEQUENCE: 21

Met Val Leu Gln Thr Gln Val Phe Ile Ser Leu Leu Leu Trp Ile Ser
 1                5                  10                  15

Gly Ala Tyr Gly Asp Ile Leu Leu Thr Gln Ser Pro Val Ile Leu Ser
             20                  25                  30

Val Ser Pro Gly Glu Arg Val Ser Phe Ser Cys Arg Ala Ser Gln Ser
         35                  40                  45

Ile Gly Thr Asn Ile His Trp Tyr Gln Gln Arg Thr Asn Gly Ser Pro
 50                  55                  60

Arg Leu Leu Ile Lys Tyr Ala Ser Lys Ser Ile Ser Gly Ile Pro Ser
 65                  70                  75                  80

Arg Phe Ser Gly Ser Gly Ser Gly Thr Asp Phe Thr Leu Ser Ile Asn
                 85                  90                  95

Ser Val Glu Ser Glu Asp Ile Ala Asp Tyr Tyr Cys Gln Gln Asn Asn
                100                 105                 110

Asn Trp Pro Thr Thr Phe Gly Ala Gly Thr Lys Leu Glu Leu Lys Arg
            115                 120                 125

Thr Val Ala Ala Pro Ser Val Phe Ile Phe Pro Pro Ser Asp Glu Gln
        130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175
```

```
Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
            195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 22
<211> LENGTH: 234
<212> TYPE: PRT
<213> ORGANISM: Homo sapiens

<400> SEQUENCE: 22

Met Val Leu Gln Thr Gln Val Phe Ile Ser Leu Leu Leu Trp Ile Ser
1               5                   10                  15

Gly Ala Tyr Gly Asp Ile Leu Leu Thr Gln Ser Pro Val Ile Leu Ser
            20                  25                  30

Val Ser Pro Gly Glu Arg Val Ser Phe Ser Cys Arg Ala Ser Gln Ser
        35                  40                  45

Ile Gly Thr Asn Ile His Trp Tyr Gln Gln Arg Thr Asn Gly Ser Pro
    50                  55                  60

Arg Leu Leu Ile Lys Tyr Ala Ser Glu Ser Ile Ser Gly Ile Pro Ser
65                  70                  75                  80

Arg Phe Ser Gly Ser Gly Ser Gly Thr Asp Phe Thr Leu Ser Ile Asn
                85                  90                  95

Ser Val Glu Ser Glu Asp Ile Ala Asp Tyr Tyr Cys Gln Gln Asn Asn
            100                 105                 110

Asn Ala Pro Thr Thr Phe Gly Ala Gly Thr Lys Leu Glu Leu Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 23
<211> LENGTH: 468
<212> TYPE: PRT
<213> ORGANISM: Homo sapiens

<400> SEQUENCE: 23

Met Asp Trp Thr Trp Arg Ile Leu Phe Leu Val Ala Ala Ala Thr Gly
1               5                   10                  15

Thr His Ala Gln Val Gln Leu Lys Gln Ser Gly Pro Gly Leu Val Gln
            20                  25                  30
```

```
Pro Ser Gln Ser Leu Ser Ile Thr Cys Thr Val Ser Gly Phe Ser Leu
        35                  40                  45

Thr Asn Tyr Gly Val His Trp Val Arg Gln Ser Pro Gly Lys Gly Leu
 50                  55                  60

Glu Trp Leu Gly Val Ile Trp Ser Gly Gly Asn Thr Asp Tyr Asn Thr
 65                  70                  75                  80

Pro Phe Thr Ser Arg Leu Ser Ile Asn Lys Asp Asn Ser Lys Ser Gln
                 85                  90                  95

Val Phe Phe Lys Met Asn Ser Leu Gln Ser Asn Asp Thr Ala Ile Tyr
                100                 105                 110

Tyr Cys Ala Arg Ala Leu Thr Tyr Tyr Asp Tyr Glu Phe Ala Tyr Trp
                115                 120                 125

Gly Gln Gly Thr Leu Val Thr Val Ser Ala Ala Ser Thr Lys Gly Pro
        130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
                180                 185                 190

Ala Val Leu Gln Ser Ser Gly Leu Tyr Ser Leu Ser Ser Val Val Thr
                195                 200                 205

Val Pro Ser Ser Ser Leu Gly Thr Gln Thr Tyr Ile Cys Asn Val Asn
        210                 215                 220

His Lys Pro Ser Asn Thr Lys Val Asp Lys Arg Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
                260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
        290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
                340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Asp Glu Leu Thr Lys Asn Gln Val
        370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
                420                 425                 430

Val Asp Lys Ser Arg Trp Gln Gln Gly Asn Val Phe Ser Cys Ser Val
        435                 440                 445
```

Met His Glu Ala Leu His Asn His Tyr Thr Gln Lys Ser Leu Ser Leu
450 455 460

Ser Pro Gly Lys
465

<210> SEQ ID NO 24
<211> LENGTH: 468
<212> TYPE: PRT
<213> ORGANISM: Homo sapiens

<400> SEQUENCE: 24

Met Asp Trp Thr Trp Arg Ile Leu Phe Leu Val Ala Ala Ala Thr Gly
1 5 10 15

Thr His Ala Gln Val Gln Leu Lys Gln Ser Gly Pro Gly Leu Val Gln
20 25 30

Pro Ser Gln Ser Leu Ser Ile Thr Cys Thr Val Ser Gly Phe Ser Leu
35 40 45

Thr Asn Tyr Gly Val His Trp Val Arg Gln Ser Pro Gly Lys Gly Leu
50 55 60

Glu Trp Leu Gly Val Ile Trp Ser Gly Gly Asn Thr Asp Tyr Asn Thr
65 70 75 80

Pro Phe Thr Ser Arg Leu Ser Ile Asn Lys Asp Asn Ser Lys Ser Gln
85 90 95

Val Phe Phe Lys Met Asn Ser Leu Gln Ser Asn Asp Thr Ala Ile Tyr
100 105 110

Tyr Cys Ala Arg Ala Leu Thr Ala Tyr Asp Tyr Glu Phe Ala Tyr Trp
115 120 125

Gly Gln Gly Thr Leu Val Thr Val Ser Ala Ala Ser Thr Lys Gly Pro
130 135 140

Ser Val Phe Pro Leu Ala Pro Ser Ser Lys Ser Thr Ser Gly Gly Thr
145 150 155 160

Ala Ala Leu Gly Cys Leu Val Lys Asp Tyr Phe Pro Glu Pro Val Thr
165 170 175

Val Ser Trp Asn Ser Gly Ala Leu Thr Ser Gly Val His Thr Phe Pro
180 185 190

Ala Val Leu Gln Ser Ser Gly Leu Tyr Ser Leu Ser Ser Val Val Thr
195 200 205

Val Pro Ser Ser Ser Leu Gly Thr Gln Thr Tyr Ile Cys Asn Val Asn
210 215 220

His Lys Pro Ser Asn Thr Lys Val Asp Lys Arg Val Glu Pro Lys Ser
225 230 235 240

Cys Asp Lys Thr His Thr Cys Pro Pro Cys Pro Ala Pro Glu Leu Leu
245 250 255

Gly Gly Pro Ser Val Phe Leu Phe Pro Pro Lys Pro Lys Asp Thr Leu
260 265 270

Met Ile Ser Arg Thr Pro Glu Val Thr Cys Val Val Val Asp Val Ser
275 280 285

His Glu Asp Pro Glu Val Lys Phe Asn Trp Tyr Val Asp Gly Val Glu
290 295 300

Val His Asn Ala Lys Thr Lys Pro Arg Glu Glu Gln Tyr Asn Ser Thr
305 310 315 320

Tyr Arg Val Val Ser Val Leu Thr Val Leu His Gln Asp Trp Leu Asn
325 330 335

Gly Lys Glu Tyr Lys Cys Lys Val Ser Asn Lys Ala Leu Pro Ala Pro
340 345 350

```
Ile Glu Lys Thr Ile Ser Lys Ala Lys Gly Gln Pro Arg Glu Pro Gln
            355                 360                 365

Val Tyr Thr Leu Pro Pro Ser Arg Asp Glu Leu Thr Lys Asn Gln Val
        370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
450                 455                 460

Ser Pro Gly Lys
465

<210> SEQ ID NO 25
<211> LENGTH: 468
<212> TYPE: PRT
<213> ORGANISM: Homo sapiens

<400> SEQUENCE: 25

Met Asp Trp Thr Trp Arg Ile Leu Phe Leu Val Ala Ala Thr Gly
1               5                   10                  15

Thr His Ala Gln Val Gln Leu Lys Gln Ser Gly Pro Gly Leu Val Gln
            20                  25                  30

Pro Ser Gln Ser Leu Ser Ile Thr Cys Thr Val Ser Gly Phe Ser Leu
        35                  40                  45

Thr Asn Tyr Gly Val His Trp Val Arg Gln Ser Pro Gly Lys Gly Leu
    50                  55                  60

Glu Trp Leu Gly Val Ile Trp Ser Gly Gly Asn Thr Asp Tyr Asn Thr
65                  70                  75                  80

Pro Phe Thr Ser Arg Leu Ser Ile Asn Lys Asp Asn Ser Lys Ser Gln
                85                  90                  95

Val Phe Phe Lys Met Asn Ser Leu Gln Ser Asn Asp Thr Ala Ile Tyr
            100                 105                 110

Tyr Cys Ala Arg Ala Leu Thr Tyr Ala Asp Tyr Glu Phe Ala Tyr Trp
        115                 120                 125

Gly Gln Gly Thr Leu Val Thr Val Ser Ala Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Arg Val Glu Pro Lys Ser
225                 230                 235                 240
```

```
Cys Asp Lys Thr His Thr Cys Pro Pro Cys Pro Ala Pro Glu Leu Leu
            245                 250                 255
Gly Gly Pro Ser Val Phe Leu Phe Pro Pro Lys Pro Lys Asp Thr Leu
        260                 265                 270
Met Ile Ser Arg Thr Pro Glu Val Thr Cys Val Val Val Asp Val Ser
            275                 280                 285
His Glu Asp Pro Glu Val Lys Phe Asn Trp Tyr Val Asp Gly Val Glu
        290                 295                 300
Val His Asn Ala Lys Thr Lys Pro Arg Glu Glu Gln Tyr Asn Ser Thr
305                 310                 315                 320
Tyr Arg Val Val Ser Val Leu Thr Val Leu His Gln Asp Trp Leu Asn
                325                 330                 335
Gly Lys Glu Tyr Lys Cys Lys Val Ser Asn Lys Ala Leu Pro Ala Pro
            340                 345                 350
Ile Glu Lys Thr Ile Ser Lys Ala Lys Gly Gln Pro Arg Glu Pro Gln
        355                 360                 365
Val Tyr Thr Leu Pro Pro Ser Arg Asp Glu Leu Thr Lys Asn Gln Val
    370                 375                 380
Ser Leu Thr Cys Leu Val Lys Gly Phe Tyr Pro Ser Asp Ile Ala Val
385                 390                 395                 400
Glu Trp Glu Ser Asn Gly Gln Pro Glu Asn Asn Tyr Lys Thr Thr Pro
                405                 410                 415
Pro Val Leu Asp Ser Asp Gly Ser Phe Phe Leu Tyr Ser Lys Leu Thr
            420                 425                 430
Val Asp Lys Ser Arg Trp Gln Gln Gly Asn Val Phe Ser Cys Ser Val
        435                 440                 445
Met His Glu Ala Leu His Asn His Tyr Thr Gln Lys Ser Leu Ser Leu
    450                 455                 460
Ser Pro Gly Lys
465

<210> SEQ ID NO 26
<211> LENGTH: 468
<212> TYPE: PRT
<213> ORGANISM: Homo sapiens

<400> SEQUENCE: 26

Met Asp Trp Thr Trp Arg Ile Leu Phe Leu Val Ala Ala Thr Gly
1               5                   10                  15
Thr His Ala Gln Val Gln Leu Lys Gln Ser Gly Pro Gly Leu Val Gln
            20                  25                  30
Pro Ser Gln Ser Leu Ser Ile Thr Cys Thr Val Ser Gly Phe Ser Leu
        35                  40                  45
Thr Asn Tyr Gly Val His Trp Val Arg Gln Ser Pro Gly Lys Gly Leu
    50                  55                  60
Glu Trp Leu Gly Val Ile Trp Ser Gly Gly Asn Thr Asp Tyr Asn Thr
65                  70                  75                  80
Pro Phe Thr Ser Arg Leu Ser Ile Asn Lys Asp Asn Ser Lys Ser Gln
                85                  90                  95
Val Phe Phe Lys Met Asn Ser Leu Gln Ser Asn Asp Thr Ala Ile Tyr
            100                 105                 110
Tyr Cys Ala Arg Ala Leu Thr Tyr Tyr Asn Tyr Glu Phe Ala Tyr Trp
        115                 120                 125
```

Gly Gln Gly Thr Leu Val Thr Val Ser Ala Ala Ser Thr Lys Gly Pro
            130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
210                 215                 220

His Lys Pro Ser Asn Thr Lys Val Asp Lys Arg Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Asp Glu Leu Thr Lys Asn Gln Val
370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
450                 455                 460

Ser Pro Gly Lys
465

<210> SEQ ID NO 27
<211> LENGTH: 468
<212> TYPE: PRT
<213> ORGANISM: Homo sapiens

<400> SEQUENCE: 27

Met Asp Trp Thr Trp Arg Ile Leu Phe Leu Val Ala Ala Ala Thr Gly
1               5                   10                  15

Thr His Ala Gln Val Gln Leu Lys Gln Ser Gly Pro Gly Leu Val Gln
            20                  25                  30

Pro Ser Gln Ser Leu Ser Ile Thr Cys Thr Val Ser Gly Phe Ser Leu
            35                  40                  45

Thr Asn Tyr Gly Val His Trp Val Arg Gln Ser Pro Gly Lys Gly Leu
50                  55                  60

Glu Trp Leu Gly Val Ile Trp Ser Gly Gly Asn Thr Asn Tyr Asn Thr
65                  70                  75                  80

Pro Phe Thr Ser Arg Leu Ser Ile Asn Lys Asp Asn Ser Lys Ser Gln
            85                  90                  95

Val Phe Phe Lys Met Asn Ser Leu Gln Ser Asn Asp Thr Ala Ile Tyr
            100                 105                 110

Tyr Cys Ala Arg Ala Leu Thr Tyr Tyr Asn Tyr Glu Phe Ala Tyr Trp
            115                 120                 125

Gly Gln Gly Thr Leu Val Thr Val Ser Ala Ala Ser Thr Lys Gly Pro
            130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
            165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
            195                 200                 205

Val Pro Ser Ser Ser Leu Gly Thr Gln Thr Tyr Ile Cys Asn Val Asn
            210                 215                 220

His Lys Pro Ser Asn Thr Lys Val Asp Lys Arg Val Glu Pro Lys Ser
225                 230                 235                 240

Cys Asp Lys Thr His Thr Cys Pro Pro Cys Pro Ala Pro Glu Leu Leu
            245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
            275                 280                 285

His Glu Asp Pro Glu Val Lys Phe Asn Trp Tyr Val Asp Gly Val Glu
290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
            325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
            355                 360                 365

Val Tyr Thr Leu Pro Pro Ser Arg Asp Glu Leu Thr Lys Asn Gln Val
            370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
            405                 410                 415

Pro Val Leu Asp Ser Asp Gly Ser Phe Phe Leu Tyr Ser Lys Leu Thr
            420                 425                 430

-continued

Val Asp Lys Ser Arg Trp Gln Gln Gly Asn Val Phe Ser Cys Ser Val
            435                 440                 445

Met His Glu Ala Leu His Asn His Tyr Thr Gln Lys Ser Leu Ser Leu
    450                 455                 460

Ser Pro Gly Lys
465

<210> SEQ ID NO 28
<211> LENGTH: 468
<212> TYPE: PRT
<213> ORGANISM: Homo sapiens

<400> SEQUENCE: 28

Met Asp Trp Thr Trp Arg Ile Leu Phe Leu Val Ala Ala Ala Thr Gly
1               5                   10                  15

Thr His Ala Gln Val Gln Leu Lys Gln Ser Gly Pro Gly Leu Val Gln
            20                  25                  30

Pro Ser Gln Ser Leu Ser Ile Thr Cys Thr Val Ser Gly Phe Ser Leu
        35                  40                  45

Thr Asn Tyr Gly Val His Trp Val Arg Gln Ser Pro Gly Lys Gly Leu
    50                  55                  60

Glu Trp Leu Gly Val Ile Trp Ser Gly Gly Asn Thr Asn Tyr Asn Thr
65                  70                  75                  80

Pro Phe Thr Ser Arg Leu Ser Ile Asn Lys Asp Asn Ser Lys Ser Gln
                85                  90                  95

Val Phe Phe Lys Met Asn Ser Leu Gln Ser Asn Asp Thr Ala Ile Tyr
            100                 105                 110

Tyr Cys Ala Arg Ala Leu Thr Tyr Tyr Asn Tyr Gln Phe Ala Tyr Trp
        115                 120                 125

Gly Gln Gly Thr Leu Val Thr Val Ser Ala Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Arg Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

```
Gly Lys Glu Tyr Lys Cys Lys Val Ser Asn Lys Ala Leu Pro Ala Pro
            340             345             350

Ile Glu Lys Thr Ile Ser Lys Ala Lys Gly Gln Pro Arg Glu Pro Gln
            355             360             365

Val Tyr Thr Leu Pro Pro Ser Arg Asp Glu Leu Thr Lys Asn Gln Val
    370             375             380

Ser Leu Thr Cys Leu Val Lys Gly Phe Tyr Pro Ser Asp Ile Ala Val
385             390             395             400

Glu Trp Glu Ser Asn Gly Gln Pro Glu Asn Asn Tyr Lys Thr Thr Pro
                405             410             415

Pro Val Leu Asp Ser Asp Gly Ser Phe Phe Leu Tyr Ser Lys Leu Thr
            420             425             430

Val Asp Lys Ser Arg Trp Gln Gln Gly Asn Val Phe Ser Cys Ser Val
            435             440             445

Met His Glu Ala Leu His Asn His Tyr Thr Gln Lys Ser Leu Ser Leu
    450             455             460

Ser Pro Gly Lys
465

<210> SEQ ID NO 29
<211> LENGTH: 5
<212> TYPE: PRT
<213> ORGANISM: Artificial Sequence
<220> FEATURE:
<223> OTHER INFORMATION: Synthetic Construct

<400> SEQUENCE: 29

Ser Gly Gly Gly Gly
1               5

<210> SEQ ID NO 30
<211> LENGTH: 4
<212> TYPE: PRT
<213> ORGANISM: Artificial Sequence
<220> FEATURE:
<223> OTHER INFORMATION: Synthetic Construct

<400> SEQUENCE: 30

Ser Gly Gly Gly
1
```

We claim:

1. An epidermal growth factor receptor (EGFR) antibody that binds preferentially to disease cells having an EGFR density greater than a normal EGFR density as compared to cells comprising the normal EGFR density, wherein the normal EGFR density is less than 10,000 EGFR molecules per cell, the EGFR antibody comprising a heavy chain and a light chain, each chain having a constant region and a variable region, each variable region comprising framework regions and complementarity determining regions (CDRs), wherein the CDRs have an amino acid sequence set forth below:

For the heavy chain:
CDR1
    (SEQ ID No. 1)
NYGVH

CDR2
    (SEQ ID No. 2)
VIWSGGNTD$^{58}$YNTPFTS

CDR3
    (SEQ ID No. 3)
ALTY$^{101}$Y$^{102}$D$^{103}$YE$^{105}$FAY

For the light chain:
CDR1
    (SEQ ID No. 4)
RASQSIGTNIH

CDR2
    (SEQ ID No. 5)
ASE$^{53}$SIS

CDR3
    (SEQ ID No. 6)
QQNNNW$^{94}$PTT wherein $Y^{101}$, $Y^{102}$ or $D^{103}$ is/are substituted with at least one of $A^{101}$, $A^{102}$ or $N^{103}$, and $D^{58}$, $Y^{101}$, $Y^{102}$, $D^{103}$, or $E^{105}$ is/are substituted with up to three of $N^{58}$, $A^{101}$, $A^{102}$, $N^{103}$ and/or $Q^{105}$, and/or wherein $E^{53}$ or $W^{94}$ is/are wild type or substituted with at least one of $K^{53}$ or $A^{94}$, wherein the substituted amino acid(s) confer(s) on said antibody a reduced EGFR binding affinity (Kd) that is 1.0 nM or weaker.

2. The antibody according to claim 1, wherein $Y^{101}$ is substituted by $A^{101}$.

3. The antibody according to claim 1, wherein $Y^{102}$ is substituted by $A^{102}$.

4. The antibody according to claim 1, wherein $D^{103}$ is replaced by $N^{103}$.

5. The antibody according to claim 1, wherein at least one of said substitutions is in the heavy chain and at least one of said substitutions is in the light chain.

6. The antibody according to claim 5, wherein $E^{53}$ and $Y^{102}$ are both substituted.

7. The antibody according to claim 6, wherein $E^{53}$ is substituted by $K^{53}$ and $Y^{102}$ is substituted by $A^{102}$.

8. The antibody according to claim 1, wherein $D^{58}$ and $D^{103}$ are both substituted.

9. The antibody according to claim 8, wherein $D^{58}$ is substituted by $N^{58}$ and $D^{103}$ is substituted by $N^{103}$.

10. The antibody according to claim 8, further wherein $E^{105}$ is substituted.

11. The antibody according to claim 10, wherein $E^{105}$ is substituted by $Q^{105}$.

12. The antibody according to claim 1, wherein $E^{53}$ is substituted by $K^{53}$.

13. The antibody according to claim 1, wherein $W^{94}$ is substituted by $A^{94}$.

14. An antibody according to claim 1, the antibody having the framework region sequences of cetuximab and/or the constant region sequence of cetuximab.

15. A bivalent fragment of an antibody according to claim 1.

16. A conjugate comprising a cytotoxin or a detectable label and, conjugated thereto, an antibody according to claim 1.

17. A pharmaceutical composition comprising a pharmaceutically acceptable carrier and the EGFR antibody of claim 1 in an amount useful to control the growth of cells presenting EGFR at a density greater than the normal EGFR density, wherein the EGFR antibody has an affinity (Kd) for EGFR that is within the range from about 1.0 nM to about 1 uM, said antibody having insignificant binding affinity for a cell presenting EGFR at a normal EGFR density, wherein the normal EGFR density is less than 10,000 EGFR molecules per cell.

18. A pharmaceutical composition comprising the antibody according to claim 1.

19. An epidermal growth factor receptor (EGFR) antibody comprising a heavy chain and a light chain, each chain having a variable region, wherein the heavy chain variable region comprises the sequence of SEQ ID No. 7 and $Y^{101}$, $Y^{102}$ or $D^{103}$ is/are substituted by at least one of $A^{101}$, $A^{102}$ or $N^{103}$ or a conservative amino acid thereof, and $D^{58}$, $Y^{101}$, $Y^{102}$, $D^{103}$, or $E^{105}$ is/are substituted with up to three of $N^{58}$, $A^{101}$, $A^{102}$, $N^{103}$ or $Q^{105}$ or a conservative amino acid thereof, and/or wherein the light chain variable region comprises the sequence of SEQ ID No. 8 and $E^{53}$ or $W^{94}$ is/are wild type or substituted by at least one of $K^{53}$ or $A^{94}$ or a conservative amino acid thereof.

20. A bivalent fragment of an antibody according to claim 19.

21. The antibody according to claim 15, wherein the fragment is a single chain Fv (scFv), a diabody, a $F(ab')_2$ fragment.

22. The antibody according to claim 19, wherein the fragment is a single chain Fv (scFv), a diabody, a $F(ab')_2$ fragment.

23. The conjugate according to claim 16, wherein the cytotoxin is a radioactive isotope, diphtheria toxin, cholera toxin, botulinus toxin, exotoxin A chain from *Pseudomonas aeruginosa*, ricin A chain, abrin A chain, modeccin A chain, alpha-sarcin, *Aleurites fordii* proteins, dianthin proteins, phytolaca Americana proteins PAPI, PAPII, or PAP-S, *Momordica charantia* inhibitor, curcin, crotin, *Sapaonaria, officinalis* inhibitor, gclonin, saporin, restrictocin, phenomycin, or a tricothecene.

24. A conjugate comprising a cytotoxin or a detectable label and, conjugated thereto, an antibody according to claim 19.

25. The conjugate according to claim 24, wherein the cytotoxin is a radioactive isotope, diphtheria toxin, cholera toxin, botulinus toxin, exotoxin A chain from *Pseudomonas aeruginosa*, ricin A chain, abrin A chain, modeccin A chain, alpha-sarcin, *Aleurites fordii* proteins, dianthin proteins, phytolaca Americana proteins PAPI, PAPII, or PAP-S, *Momordica charantia* inhibitor, curcin, crotin, *Sapaonaria, officinalis* inhibitor, gclonin, saporin, restrictocin, phenomycin, or a tricothecene.

* * * * *